US010309964B2

(12) United States Patent
Ge et al.

(10) Patent No.: US 10,309,964 B2
(45) Date of Patent: Jun. 4, 2019

(54) METHOD FOR ASSESSING RISK OF HUMAN CYTOMEGALOVIRUS ACTIVE INFECTION IN BODY AND RELATED KIT

(71) Applicant: XIAMEN UNIVERSITY, Xiamen, Fujian Province (CN)

(72) Inventors: Shengxiang Ge, Fujian (CN); Jinjie Li, Fujian (CN); Xi Huang, Fujian (CN); Tingdong Li, Fujian (CN); Jun Zhang, Fujian (CN); Ningshao Xia, Fujian (CN)

(73) Assignee: Xiamen University, Xiamen, Fujian Province (CN)

( * ) Notice: Subject to any disclaimer, the term of this patent is extended or adjusted under 35 U.S.C. 154(b) by 0 days.

(21) Appl. No.: 15/549,443

(22) PCT Filed: Jan. 26, 2016

(86) PCT No.: PCT/CN2016/072094
§ 371 (c)(1),
(2) Date: Aug. 8, 2017

(87) PCT Pub. No.: WO2016/127785
PCT Pub. Date: Aug. 18, 2016

(65) Prior Publication Data
US 2018/0031556 A1    Feb. 1, 2018

(30) Foreign Application Priority Data

Feb. 9, 2015 (CN) .......................... 2015 1 0067190

(51) Int. Cl.
| | | |
|---|---|---|
| *A61K 39/42* | (2006.01) | |
| *G01N 33/53* | (2006.01) | |
| *G01N 33/543* | (2006.01) | |
| *G01N 33/569* | (2006.01) | |

(52) U.S. Cl.
CPC ....... *G01N 33/56983* (2013.01); *G01N 33/53* (2013.01); *G01N 33/543* (2013.01); *G01N 33/569* (2013.01); *G01N 33/56994* (2013.01); *A61K 39/42* (2013.01); *G01N 2333/045* (2013.01); *G01N 2469/20* (2013.01); *G01N 2800/50* (2013.01); *G01N 2800/52* (2013.01)

(58) Field of Classification Search
CPC .................. A61K 39/12; A61K 39/245; A61K 2039/575; A61K 49/0058; A61K 2039/6056; A61K 39/395; A61K 2039/525; A61K 39/42; C12N 7/00; C12N 2710/16122; C07K 14/005; C07K 16/088; C07K 14/03; G01N 33/56983; G01N 33/56994; G01N 33/53; G01N 33/569; G01N 33/543; G01N 2800/52; G01N 2800/50; G01N 2469/20; G01N 2333/045
See application file for complete search history.

(56) References Cited

U.S. PATENT DOCUMENTS

| 6,074,817 A | 6/2000 | Landini et al. |
|---|---|---|
| 2013/0109010 A1* | 5/2013 | Fujii .................... C07K 14/005 435/5 |

FOREIGN PATENT DOCUMENTS

| CN | 102353777 A | 2/2012 |
|---|---|---|
| CN | 103003694 A | 3/2013 |
| CN | 103760347 A | 4/2014 |
| EP | 1304574 A2 | 4/2003 |
| WO | 99/15899 A1 | 4/1999 |

OTHER PUBLICATIONS

Essa S, Pacsa A, Said T, Nampoory MR, Raghupathy R, Johny KV, Al-Nakib W, Al-Mosawy M. Is combined pretransplantation seropositivity of kidney transplant recipients for cytomegalovirus antigens (pp. 150 and pp. 28) a predictor for protection against infection? Med Princ Pract. 2008;17(1):66-70.*
pp. 150. UniProtKB/Swiss-Prot: P08318.1, Dep. Apr. 24, 1993.*
pp. 28. Cytoplasmic envelopment protein 3. UniProtKB/Swiss-Prot: P13200.3, Dep. Apr. 24, 1993.*
Gaskell R, et. al. Vet Res. Mar.-Apr. 2007;38(2):337-54. Epub Feb. 13, 2007.*
Small JC, et. al. Curr Opin Virol. Oct. 2011;1(4):241-5.*
Greijer, A. E., et al., "Molecular fine-specificity analysis of antibody responses to human cytomegalovirus and design of novel synthetic-peptide-based serodiagnostic assays", Journal of clinical microbiology, Jan. 31, 1999 (Jan. 31, 1999), No. 1, vol. 37, pp. 179-188.
Vornhagen, R., et al, "Early serodiagnosis of acute human cytomegalovirus infection by enzyme-linked immunosorbent assay using recombinant antigens", Journal of clinical microbiology, Apr. 30, 1994 (Apr. 30, 1994), No. 4, vol. 32, pp. 981-986.
Yiqiu, Q., et al., "Establishment and evaluation of an indirect enzyme-linked immunosorbent assay based on synthetic peptides for the detection of specific antibodies to Human cytomegalovirus", Laboratory Medicine, Nov. 30, 2008 (Nov. 30, 2008), No. 6, vol. 23, pp. 604-607.
Zhang, Meng et al., "Establishment and application of novel method for detecting specific cytomegalovirus IgG antibody", Chinese Journal of Reproductive Health, Dec. 31, 2009 (Dec. 31, 2009), No. 3, vol. 20, pp. 154-157.

(Continued)

*Primary Examiner* — Rachel B Gill
(74) *Attorney, Agent, or Firm* — Honigman LLP; Thomas A. Wootton, Esq.; Jonathan P. O'Brien

(57) ABSTRACT

The invention belongs to the fields of medicine and immunology, particularly, the field of immunological diagnosis. In particular, the invention discloses a method for assessing whether a subject is at risk of developing human cytomegalovirus (HCMV) active infection and a kit therefore. The method comprises the steps of: (1) determining the level of an antibody against a HCMV protein in a body fluid sample from the subject; and (2) comparing the level with a predetermined reference value, wherein if the level is below the predetermined reference value, the subject is determined to be at risk of developing HCMV active infection. In addition, the invention also discloses a method for screening a candidate drug which is capable of improving the ability of a subject to resist human cytomegalovirus (HCMV) active infection, and a kit therefore.

15 Claims, 8 Drawing Sheets

Specification includes a Sequence Listing.

(56) References Cited

OTHER PUBLICATIONS

Dollard SC, Grosse SD, Ross DS; New estimates of the prevalence of neurological and sensory sequelae and mortality associated with congenital cytomegalovirus infection. Rev Med Virol. 2007, 17:355-363.
Wood LJ, Baxter MK, Plafker SM, Gibson W. Human cytomegalovirus capsid assembly protein precursor (pUL80.5) interacts with itself and with the major capsid protein (pUL86) through two different domains. J Virology. 1997, 71:179-190.
Fowler KB, Stagno S, Pass RF, et al; The outcome of congenital cytomegalovirus infection in relation to maternal antibody status. N Engl J Med. 1992, 326:663-667.2.
Kenneson A, Cannon MJ.; Review and meta-analysis of the epidemiology of congenital cytomegalovirus infection. Rev Med Virol. 2007,17:253-276.
Manicklal S, Emery VC, Lazzarotto T, Boppana SB, Gupta RK. The "silent" global burden of congenital cytomegalovirus. Clin Microbiol Rev. 2013, 26:86-102.
Mussi-Pinhata MM, Yamamoto AY, MouraBrito RM, de Lima Isaac M, de Carvalho e Oliveira PF, Boppana S, Britt WJ. Birth prevalence and natural history of congenital cytomegalovirus infection in a highly seroimmune population. Clin Infect Dis. 2009, 49:522-528.
Yamamoto AY, Mussi-Pinhata MM, Isaac Mde L, Amaral FR, Carvalheiro CG, Aragon DC, Manfredi AK, Boppana SB, Britt WJ. Congenital cytomegalovirus infection as a cause of sensorineural hearing loss in a highly immune population. Pediatr Infect Dis J. 2011, 30:1043-1046.
Boppana SB, Rivera LB, Fowler KB, Mach M, Britt WJ. Intrauterine transmission of cytomegalovirus to infants of women with preconceptional immunity. N Engl J Med. 2001, 344:1366-1371.
Ross SA, Arora N, Novak Z, Fowler KB, Britt WJ, Boppana SB. Cytomegalovirus reinfections in healthy seroimmune women. J Infect Dis. 2010, 201:386-389.
Torres L, Tang Q. Immediate-early (IE) gene regulation of cytomegalovirus: 1E1- and pp71-mediated viral strategies against cellular defenses. Virologica Sinica. 2014, 29:343-352.
Ross SA, Novak Z, Pati S, Boppana SB. Overview of the diagnosis of cytomegalovirus infection. Infect Disord Drug Targets. 2011, 11:466-474.
Weber B, Berger A, Rabenau H. Human cytomegalovirus infection: diagnostic potential of recombinant antigens for cytomegalovirus antibody detection. Journal of Virological Methods. 2001, 96:157-170.
Jahn G, Scholl BC, Traupe B, Fleckenstein B. The two major structural phosphoproteins (pp65 and pp150) of human cytomegalovirus and their antigenic properties. J Gen Virol. 1987, 68:1327-1337.
Plachter B, Wieczorek L, Scholl BC, Ziegelmaier R, Jahn G. Detection of cytomegalovirus antibodies by an enzyme-linked immunosorbent assay using recombinant polypeptides of the large phosphorylated tegument protein pp150. J Clin Microbiol. 1992, 30:201-206.
Tang A, Li F, Freed DC, Finnefrock AC, Casimiro DR, Wang D, Fu TM. A novel high-throughput neutralization assay for supporting clinical evaluations of human cytomegalovirus vaccines. Vaccine. 2011, 29:8350-8356.
Baldick CJ Jr., Shenk T. Proteins associated with purified human cytomegalovirus particles. J Virology. 1996, 70:6097-6105.
Gambarino S, Callea S, Rizzo G, Montanan P, Loiacono E, Bergallo M. Evaluation of UL99 transcript as a target for antiviral treatment efficacy. J of Virological Methods. 2014, 207:104-109.
Loveland AN, Nguyen NL, Brignole EJ, Gibson W. The amino-conserved domain of human cytomegalovirus UL80a proteins is required for key interactions during early stages of capsid formation and virus production. J of Virology. 2007, 81:620-628.
McVoy MA. Cytomegalovirus vaccines. Clinical Infectious Diseases. 2013, 57:196-199.
Sinigalia E, Alvisi G, Segre CV, Mercorelli B, Muratore G, Winkler M, Hsiao HH, Urlaub H, Ripalti A, Chiocca S, Palu G, Loregian A. The human cytomegalovirus DNA polymerase processivity factor UL44 is modified by SUMO in a DNA-dependent manner. PLOS ONE. 2012, 7:1-18.
Strang BL, Boulant S, Chang L, Knipe DM, Kirchhausen T, Coen DM. Human Cytomegatovirus UL44 concentrates at the periphery of replication compartments, the site of viral DNA synthesis. J Virology. 2011, 86:2089-2095.
Tomtishen JP, III. Human cytomegalovirus tegument proteins. Virology Journal. 2012, 9:1-8.
Essa, S., et al, Is Combined Pretransplantation Seropositivity of Kidney Transplant Recipients for Cytomegalovirus Antigents (pp150 and pp28) a Predictor for Protection Against Infection?, Medical Principles and Practice, 2008, vol. 17, pp. 66-70.
He, Xiao-zhou, et al., The Progres of Congenital Cytomegalovirus Infection and Detection Methods, Chinese Journal of Virology, Jan. 2012, vol. 28, No. 1.
UniProtKB/Swiss-Prot: P08318.1, Dep. Apr. 24, 1993, pp. 150.
UniProtKB/Swiss-Prot: P13200.3: 19900101; Cytoplasmic envelopment protein 3, UniProtKB/Swiss-Prot: P13200.3, Dep. Apr. 24, 1993, pp. 28.
Bruminhent, Jackrapong, et al, Risk Factors for Cytomegalovirus Reactivation After Liver Transplantation: Can Pre-Transplant Cytomegalovirus Antibody Titers Predict Outcome?; Liver Transplantation 21:539-546, Apr. 2015, American Association for the Study of Liver Diseases.

\* cited by examiner

SEQUENCE LISTING

```
<160> NUMBER OF SEQ ID NOS: 19

<210> SEQ ID NO 1
<211> LENGTH: 1048
<212> TYPE: PRT
```

<213> ORGANISM: Human cytomegalovirus

<400> SEQUENCE: 1

```
Met Ser Leu Gln Phe Ile Gly Leu Gln Arg Arg Asp Val Val Ala Leu
1               5                   10                  15

Val Asn Phe Leu Arg His Leu Thr Gln Lys Pro Asp Val Asp Leu Glu
            20                  25                  30

Ala His Pro Lys Ile Leu Lys Lys Cys Gly Glu Lys Arg Leu His Arg
        35                  40                  45

Arg Thr Val Leu Phe Asn Glu Leu Met Leu Trp Leu Gly Tyr Tyr Arg
    50                  55                  60

Glu Leu Arg Phe His Asn Pro Asp Leu Ser Ser Val Leu Glu Glu Phe
65                  70                  75                  80

Glu Val Arg Cys Val Ala Val Ala Arg Arg Gly Tyr Thr Tyr Pro Phe
                85                  90                  95

Gly Asp Arg Gly Lys Ala Arg Asp His Leu Ala Val Leu Asp Arg Thr
            100                 105                 110

Glu Phe Asp Thr Asp Val Arg His Asp Ala Glu Ile Val Glu Arg Ala
        115                 120                 125

Leu Val Ser Ala Val Ile Leu Ala Lys Met Ser Val Arg Glu Thr Leu
    130                 135                 140

Val Thr Ala Ile Gly Gln Thr Glu Pro Ile Ala Phe Val His Leu Lys
145                 150                 155                 160

Asp Thr Glu Val Gln Arg Ile Glu Glu Asn Leu Glu Gly Val Arg Arg
                165                 170                 175

Asn Met Phe Cys Val Lys Pro Leu Asp Leu Asn Leu Asp Arg His Ala
            180                 185                 190

Asn Thr Ala Leu Val Asn Ala Val Asn Lys Leu Val Tyr Thr Gly Arg
        195                 200                 205

Leu Ile Met Asn Val Arg Arg Ser Trp Glu Glu Leu Glu Arg Lys Cys
    210                 215                 220

Leu Ala Arg Ile Gln Glu Arg Cys Lys Leu Leu Val Lys Glu Leu Arg
225                 230                 235                 240

Met Cys Leu Ser Phe Asp Ser Asn Tyr Cys Arg Asn Ile Leu Lys His
                245                 250                 255

Ala Val Glu Asn Gly Asp Ser Ala Asp Thr Leu Leu Glu Leu Leu Ile
            260                 265                 270

Glu Asp Phe Asp Ile Tyr Val Asp Ser Phe Pro Gln Ser Ala His Thr
        275                 280                 285

Phe Leu Gly Ala Arg Ser Pro Ser Leu Glu Phe Asp Asp Ala Asn
    290                 295                 300

Leu Leu Ser Leu Gly Gly Gly Ser Ala Phe Ser Ser Val Pro Lys Lys
305                 310                 315                 320

His Val Pro Thr Gln Pro Leu Asp Gly Trp Ser Trp Ile Ala Ser Pro
                325                 330                 335

Trp Lys Gly His Lys Pro Phe Arg Phe Glu Ala His Gly Ser Leu Ala
            340                 345                 350

Pro Ala Ala Glu Ala His Ala Ala Arg Ser Ala Ala Val Gly Tyr Tyr
        355                 360                 365

Asp Glu Glu Glu Lys Arg Arg Glu Arg Gln Lys Arg Val Asp Asp Glu
    370                 375                 380

Val Val Gln Arg Glu Lys Gln Gln Leu Lys Ala Trp Glu Glu Arg Gln
385                 390                 395                 400
```

-continued

```
Gln Asn Leu Gln Gln Arg Gln Gln Pro Pro Pro Ala Arg Lys
                405                 410                 415

Pro Ser Ala Ser Arg Arg Leu Phe Gly Ser Ala Asp Glu Asp
                420                 425                 430

Asp Asp Asp Asp Glu Lys Asn Ile Phe Thr Pro Ile Lys Lys Pro
            435                 440                 445

Gly Thr Ser Gly Lys Gly Ala Ala Ser Gly Gly Val Ser Ser Ile
            450                 455                 460

Phe Ser Gly Leu Leu Ser Ser Gly Ser Gln Lys Pro Thr Ser Gly Pro
465                 470                 475                 480

Leu Asn Ile Pro Gln Gln Gln Arg His Ala Ala Phe Ser Leu Val
                485                 490                 495

Ser Pro Gln Val Thr Lys Ala Ser Pro Gly Arg Val Arg Arg Asp Ser
                500                 505                 510

Ala Trp Asp Val Arg Pro Leu Thr Glu Thr Arg Gly Asp Leu Phe Ser
                515                 520                 525

Gly Asp Glu Asp Ser Asp Ser Ser Asp Gly Tyr Pro Pro Asn Arg Gln
                530                 535                 540

Asp Pro Arg Phe Thr Asp Thr Leu Val Asp Ile Thr Asp Thr Glu Thr
545                 550                 555                 560

Ser Ala Lys Pro Pro Val Thr Thr Ala Tyr Lys Phe Glu Gln Pro Thr
                565                 570                 575

Leu Thr Phe Gly Ala Gly Val Asn Val Pro Ala Gly Ala Gly Ala Ala
                580                 585                 590

Ile Leu Thr Pro Thr Pro Val Asn Pro Ser Thr Ala Pro Ala Pro Ala
                595                 600                 605

Pro Thr Pro Thr Phe Ala Gly Thr Gln Thr Pro Val Asn Gly Asn Ser
                610                 615                 620

Pro Trp Ala Pro Thr Ala Pro Leu Pro Gly Asp Met Asn Pro Ala Asn
625                 630                 635                 640

Trp Pro Arg Glu Arg Ala Trp Ala Leu Lys Asn Pro His Leu Ala Tyr
                645                 650                 655

Asn Pro Phe Arg Met Pro Thr Thr Ser Thr Ala Ser Gln Asn Thr Val
                660                 665                 670

Ser Thr Thr Pro Arg Arg Pro Ser Thr Pro Arg Ala Ala Val Thr Gln
                675                 680                 685

Thr Ala Ser Arg Asp Ala Ala Asp Glu Val Trp Ala Leu Arg Asp Gln
                690                 695                 700

Thr Ala Glu Ser Pro Val Glu Asp Ser Glu Glu Asp Asp Ser
705                 710                 715                 720

Ser Asp Thr Gly Ser Val Val Ser Leu Gly His Thr Thr Pro Ser Ser
                725                 730                 735

Asp Tyr Asn Asn Asp Val Ile Ser Pro Pro Ser Gln Thr Pro Glu Gln
                740                 745                 750

Ser Thr Pro Ser Arg Ile Arg Lys Ala Lys Leu Ser Ser Pro Met Thr
                755                 760                 765

Thr Thr Ser Thr Ser Gln Lys Pro Val Leu Gly Lys Arg Val Ala Thr
                770                 775                 780

Pro His Ala Ser Ala Arg Ala Gln Thr Val Thr Ser Thr Pro Val Gln
785                 790                 795                 800

Gly Arg Leu Glu Lys Gln Val Ser Gly Thr Pro Ser Thr Val Pro Ala
                805                 810                 815

Thr Leu Leu Gln Pro Gln Pro Ala Ser Ser Lys Thr Thr Ser Ser Arg
```

```
                      820                 825                 830
Asn Val Thr Ser Gly Ala Gly Thr Ser Ser Ala Ser Ser Ala Arg Gln
            835                 840                 845

Pro Ser Ala Ser Ala Ser Val Leu Ser Pro Thr Glu Asp Val Val
        850                 855                 860

Ser Pro Ala Thr Ser Pro Leu Ser Met Leu Ser Ser Ala Ser Pro Ser
865                 870                 875                 880

Pro Ala Lys Ser Ala Pro Pro Ser Pro Val Lys Gly Arg Gly Ser Arg
                885                 890                 895

Val Gly Val Pro Ser Leu Lys Pro Thr Leu Gly Gly Lys Ala Val Val
        900                 905                 910

Gly Arg Pro Pro Ser Val Pro Val Ser Gly Ser Ala Pro Gly Arg Leu
        915                 920                 925

Ser Gly Ser Ser Arg Ala Ala Ser Thr Thr Pro Thr Tyr Pro Ala Val
        930                 935                 940

Thr Thr Val Tyr Pro Pro Ser Ser Thr Ala Lys Ser Ser Val Ser Asn
945                 950                 955                 960

Ala Pro Pro Val Ala Ser Pro Ser Ile Leu Lys Pro Gly Ala Ser Ala
                965                 970                 975

Ala Leu Gln Ser Arg Arg Ser Thr Gly Thr Ala Ala Val Gly Ser Pro
            980                 985                 990

Val Lys Ser Thr Thr Gly Met Lys Thr Val Ala Phe Asp Leu Ser Ser
        995                1000                1005

Pro Gln Lys Ser Gly Thr Gly Pro Gln Pro Gly Ser Ala Gly Met
        1010                1015                1020

Gly Gly Ala Lys Thr Pro Ser Asp Ala Val Gln Asn Ile Leu Gln
        1025                1030                1035

Lys Ile Glu Lys Ile Lys Asn Thr Glu Glu
        1040                1045

<210> SEQ ID NO 2
<211> LENGTH: 188
<212> TYPE: PRT
<213> ORGANISM: Human cytomegalovirus

<400> SEQUENCE: 2

Asp Asp Val Val Ser Pro Ala Thr Ser Pro Leu Ser Met Leu Ser Ser
1               5                  10                  15

Ala Ser Pro Ser Pro Ala Lys Ser Ala Pro Pro Ser Pro Val Lys Gly
            20                  25                  30

Arg Gly Ser Arg Val Gly Val Pro Ser Leu Lys Pro Thr Leu Gly Gly
        35                  40                  45

Lys Ala Val Val Gly Arg Pro Pro Ser Val Pro Val Ser Gly Ser Ala
50                  55                  60

Pro Gly Arg Leu Ser Gly Ser Ser Arg Ala Ala Ser Thr Thr Pro Thr
65                  70                  75                  80

Tyr Pro Ala Val Thr Thr Val Tyr Pro Pro Ser Ser Thr Ala Lys Ser
                85                  90                  95

Ser Val Ser Asn Ala Pro Pro Val Ala Ser Pro Ser Ile Leu Lys Pro
            100                 105                 110

Gly Ala Ser Ala Ala Leu Gln Ser Arg Arg Ser Thr Gly Thr Ala Ala
        115                 120                 125

Val Gly Ser Pro Val Lys Ser Thr Thr Gly Met Lys Thr Val Ala Phe
    130                 135                 140
```

```
Asp Leu Ser Ser Pro Gln Lys Ser Gly Thr Gly Pro Gln Pro Gly Ser
145                 150                 155                 160

Ala Gly Met Gly Gly Ala Lys Thr Pro Ser Asp Ala Val Gln Asn Ile
            165                 170                 175

Leu Gln Lys Ile Glu Lys Ile Lys Asn Thr Glu Glu
        180                 185

<210> SEQ ID NO 3
<211> LENGTH: 190
<212> TYPE: PRT
<213> ORGANISM: Human cytomegalovirus

<400> SEQUENCE: 3

Met Gly Ala Glu Leu Cys Lys Arg Ile Cys Cys Glu Phe Gly Thr Thr
1               5                   10                  15

Pro Gly Glu Pro Leu Lys Asp Ala Leu Gly Arg Gln Val Ser Leu Arg
            20                  25                  30

Ser Tyr Asp Asn Ile Pro Pro Thr Ser Ser Asp Glu Gly Glu Asp
        35                  40                  45

Asp Asp Asp Gly Glu Asp Asp Asn Glu Glu Arg Gln Gln Lys Leu
    50                  55                  60

Arg Leu Cys Gly Ser Gly Cys Gly Gly Asn Asp Ser Ser Ser Gly Ser
65                  70                  75                  80

His Arg Glu Ala Thr His Asp Gly Ser Lys Lys Asn Ala Val Arg Ser
                85                  90                  95

Thr Phe Arg Glu Asp Lys Ala Pro Lys Pro Ser Lys Gln Ser Lys Lys
            100                 105                 110

Lys Lys Lys Pro Ser Lys His His His His Gln Gln Ser Ser Ile Met
        115                 120                 125

Gln Glu Thr Asp Asp Leu Asp Glu Glu Asp Thr Ser Ile Tyr Leu Ser
    130                 135                 140

Pro Pro Pro Val Pro Pro Val Gln Val Val Ala Lys Arg Leu Pro Arg
145                 150                 155                 160

Pro Asp Thr Pro Arg Thr Pro Arg Gln Lys Lys Ile Ser Gln Arg Pro
                165                 170                 175

Pro Thr Pro Gly Thr Lys Lys Pro Ala Ala Ser Leu Pro Phe
            180                 185                 190

<210> SEQ ID NO 4
<211> LENGTH: 561
<212> TYPE: PRT
<213> ORGANISM: Human cytomegalovirus

<400> SEQUENCE: 4

Met Glu Ser Arg Gly Arg Arg Cys Pro Glu Met Ile Ser Val Leu Gly
1               5                   10                  15

Pro Ile Ser Gly His Val Leu Lys Ala Val Phe Ser Arg Gly Asp Thr
            20                  25                  30

Pro Val Leu Pro His Glu Thr Arg Leu Leu Gln Thr Gly Ile His Val
        35                  40                  45

Arg Val Ser Gln Pro Ser Leu Ile Leu Val Ser Gln Tyr Thr Pro Asp
    50                  55                  60

Ser Thr Pro Cys His Arg Gly Asp Asn Gln Leu Gln Val Gln His Thr
65                  70                  75                  80

Tyr Phe Thr Gly Ser Glu Val Glu Asn Val Ser Val Asn Val His Asn
                85                  90                  95
```

```
Pro Thr Gly Arg Ser Ile Cys Pro Ser Gln Glu Pro Met Ser Ile Tyr
                100                 105                 110

Val Tyr Ala Leu Pro Leu Lys Met Leu Asn Ile Pro Ser Ile Asn Val
            115                 120                 125

His His Tyr Pro Ser Ala Ala Glu Arg Lys His Arg His Leu Pro Val
        130                 135                 140

Ala Asp Ala Val Ile His Ala Ser Gly Lys Gln Met Trp Gln Ala Arg
145                 150                 155                 160

Leu Thr Val Ser Gly Leu Ala Trp Thr Arg Gln Gln Asn Gln Trp Lys
                165                 170                 175

Glu Pro Asp Val Tyr Tyr Thr Ser Ala Phe Val Phe Pro Thr Lys Asp
            180                 185                 190

Val Ala Leu Arg His Val Val Cys Ala His Glu Leu Val Cys Ser Met
        195                 200                 205

Glu Asn Thr Arg Ala Thr Lys Met Gln Val Ile Gly Asp Gln Tyr Val
    210                 215                 220

Lys Val Tyr Leu Glu Ser Phe Cys Glu Asp Val Pro Ser Gly Lys Leu
225                 230                 235                 240

Phe Met His Val Thr Leu Gly Ser Asp Val Glu Glu Asp Leu Thr Met
                245                 250                 255

Thr Arg Asn Pro Gln Pro Phe Met Arg Pro His Glu Arg Asn Gly Phe
            260                 265                 270

Thr Val Leu Cys Pro Lys Asn Met Ile Ile Lys Pro Gly Lys Ile Ser
        275                 280                 285

His Ile Met Leu Asp Val Ala Phe Thr Ser His Glu His Phe Gly Leu
    290                 295                 300

Leu Cys Pro Lys Ser Ile Pro Gly Leu Ser Ile Ser Gly Asn Leu Leu
305                 310                 315                 320

Met Asn Gly Gln Gln Ile Phe Leu Glu Val Gln Ala Ile Arg Glu Thr
                325                 330                 335

Val Glu Leu Arg Gln Tyr Asp Pro Val Ala Ala Leu Phe Phe Phe Asp
            340                 345                 350

Ile Asp Leu Leu Leu Gln Arg Gly Pro Gln Tyr Ser Glu His Pro Thr
        355                 360                 365

Phe Thr Ser Gln Tyr Arg Ile Gln Gly Lys Leu Glu Tyr Arg His Thr
    370                 375                 380

Trp Asp Arg His Asp Glu Gly Ala Ala Gln Gly Asp Asp Asp Val Trp
385                 390                 395                 400

Thr Ser Gly Ser Asp Ser Asp Glu Glu Leu Val Thr Thr Glu Arg Lys
                405                 410                 415

Thr Pro Arg Val Thr Gly Gly Ala Met Ala Gly Ala Ser Thr Ser Ser
            420                 425                 430

Ala Gly Arg Lys Arg Lys Ser Ala Ser Ser Ala Thr Ala Cys Thr Ser
        435                 440                 445

Gly Val Met Thr Arg Gly Arg Leu Lys Ala Glu Ser Thr Val Ala Pro
    450                 455                 460

Glu Glu Asp Thr Asp Glu Asp Ser Asp Asn Glu Ile His Asn Pro Ala
465                 470                 475                 480

Val Phe Thr Trp Pro Pro Trp Gln Ala Gly Ile Leu Ala Arg Asn Leu
                485                 490                 495

Val Pro Met Val Ala Thr Val Gln Gly Gln Asn Leu Lys Tyr Gln Glu
            500                 505                 510

Phe Phe Trp Asp Ala Asn Asp Ile Tyr Arg Ile Phe Ala Glu Leu Glu
```

```
            515                 520                 525
Gly Val Trp Gln Pro Ala Ala Gln Pro Lys Arg Arg His Arg Gln
    530                 535                 540

Asp Ala Leu Pro Gly Pro Cys Ile Ala Ser Thr Pro Lys Lys His Arg
545                 550                 555                 560

Gly

<210> SEQ ID NO 5
<211> LENGTH: 433
<212> TYPE: PRT
<213> ORGANISM: Human cytomegalovirus

<400> SEQUENCE: 5

Met Asp Arg Lys Thr Arg Leu Ser Glu Pro Thr Leu Ala Leu Arg
1               5                   10                  15

Leu Lys Pro Tyr Lys Thr Ala Ile Gln Gln Leu Arg Ser Val Ile Arg
                20                  25                  30

Ala Leu Lys Glu Asn Thr Val Thr Phe Leu Pro Thr Pro Ser Leu
            35                  40                  45

Ile Leu Gln Thr Val Arg Ser His Cys Val Ser Lys Ile Thr Phe Asn
50                  55                  60

Ser Ser Cys Leu Tyr Ile Thr Asp Lys Ser Phe Gln Pro Lys Thr Ile
65                  70                  75                  80

Asn Asn Ser Thr Pro Leu Leu Gly Asn Phe Met Tyr Leu Thr Ser Ser
                85                  90                  95

Lys Asp Leu Thr Lys Phe Tyr Val Gln Asp Ile Ser Asp Leu Ser Ala
            100                 105                 110

Lys Ile Ser Met Cys Ala Pro Asp Phe Asn Met Glu Phe Ser Ser Ala
        115                 120                 125

Cys Val His Gly Gln Asp Ile Val Arg Glu Ser Glu Asn Ser Ala Val
130                 135                 140

His Val Asp Leu Asp Phe Gly Val Val Ala Asp Leu Leu Lys Trp Ile
145                 150                 155                 160

Gly Pro His Thr Arg Val Lys Arg Asn Val Lys Lys Ala Pro Cys Pro
                165                 170                 175

Thr Gly Thr Val Gln Ile Leu Val His Ala Gly Pro Pro Ala Ile Lys
            180                 185                 190

Phe Ile Leu Thr Asn Gly Ser Glu Leu Glu Phe Thr Ser Asn Asn Arg
        195                 200                 205

Val Ser Phe His Gly Val Lys Asn Met Arg Ile Asn Val Gln Leu Lys
210                 215                 220

Asn Phe Tyr Gln Thr Leu Leu Asn Cys Ala Val Thr Lys Leu Pro Cys
225                 230                 235                 240

Thr Leu Arg Ile Val Thr Glu His Asp Thr Leu Leu Tyr Val Ala Ser
                245                 250                 255

Arg Asn Gly Leu Phe Ala Val Glu Asn Phe Leu Thr Glu Glu Pro Phe
            260                 265                 270

Gln Arg Gly Asp Pro Phe Asp Lys Asn Tyr Val Gly Asn Ser Gly Lys
        275                 280                 285

Ser Arg Gly Gly Gly Gly Gly Gly Ser Leu Ser Ser Leu Ala Asn
    290                 295                 300

Ala Gly Gly Leu His Asp Asp Gly Pro Gly Leu Asp Asn Asp Leu Met
305                 310                 315                 320

Asn Glu Pro Met Gly Leu Gly Gly Leu Gly Gly Gly Gly Gly Gly
```

-continued

```
                    325                 330                 335
Gly Lys Lys His Asp Arg Gly Gly Gly Ser Gly Thr Arg Lys
            340                 345                 350
Met Ser Ser Gly Gly Gly Gly Asp His Asp His Gly Leu Ser Ser
            355                 360                 365
Lys Glu Lys Tyr Glu Gln His Lys Ile Thr Ser Tyr Leu Thr Ser Lys
        370                 375                 380
Gly Gly Ser Gly Gly Gly Gly Gly Gly Gly Leu Asp Arg
385                 390                 395                 400
Asn Ser Gly Asn Tyr Phe Asn Asp Ala Lys Glu Glu Ser Asp Ser Glu
                405                 410                 415
Asp Ser Val Thr Phe Glu Phe Val Pro Asn Thr Lys Lys Gln Lys Cys
                420                 425                 430
Gly
```

<210> SEQ ID NO 6
<211> LENGTH: 373
<212> TYPE: PRT
<213> ORGANISM: Human cytomegalovirus

<400> SEQUENCE: 6

```
Met Ser His Pro Leu Ser Ala Ala Val Pro Ala Ala Thr Ala Pro Pro
1               5                   10                  15
Gly Ala Thr Val Ala Gly Ala Ser Pro Ala Val Ser Ser Leu Ala Trp
            20                  25                  30
Pro His Asp Gly Val Tyr Leu Pro Lys Asp Ala Phe Phe Ser Leu Leu
        35                  40                  45
Gly Ala Ser Arg Ser Ala Val Pro Val Met Tyr Pro Gly Ala Val Ala
    50                  55                  60
Ala Pro Pro Ser Ala Ser Pro Ala Pro Leu Pro Leu Pro Ser Tyr Pro
65                  70                  75                  80
Ala Ser Tyr Gly Ala Pro Val Val Gly Tyr Asp Gln Leu Ala Ala Arg
                85                  90                  95
His Phe Ala Asp Tyr Val Asp Pro His Tyr Pro Gly Trp Gly Arg Arg
            100                 105                 110
Tyr Glu Pro Ala Pro Ser Leu His Pro Ser Tyr Pro Val Pro Pro Pro
        115                 120                 125
Pro Ser Pro Ala Tyr Tyr Arg Arg Asp Ser Pro Gly Gly Met Asp
    130                 135                 140
Glu Pro Pro Ser Gly Trp Glu Arg Tyr Asp Gly Gly His Arg Gly Gln
145                 150                 155                 160
Ser Gln Lys Gln His Arg His Gly Gly Ser Gly Gly His Asn Lys Arg
                165                 170                 175
Arg Lys Glu Thr Ala Ala Ala Ser Ser Ser Ser Asp Glu Asp Leu
            180                 185                 190
Ser Phe Pro Gly Glu Ala Glu His Gly Arg Ala Arg Lys Arg Leu Lys
        195                 200                 205
Ser His Val Asn Ser Asp Gly Ser Gly Gly His Ala Gly Ser Asn
    210                 215                 220
Gln Gln Gln Gln Gln Arg Tyr Asp Glu Leu Arg Asp Ala Ile His Glu
225                 230                 235                 240
Leu Lys Arg Asp Leu Phe Ala Ala Arg Gln Ser Ser Thr Leu Leu Ser
                245                 250                 255
Ala Ala Leu Pro Ser Ala Ala Ser Ser Pro Thr Thr Thr Val
```

```
                260                 265                 270
Cys Thr Pro Thr Gly Glu Leu Thr Ser Gly Gly Gly Glu Thr Pro Thr
            275                 280                 285
Ala Leu Leu Ser Gly Gly Ala Lys Val Ala Glu Arg Ala Gln Ala Gly
        290                 295                 300
Val Val Asn Ala Ser Cys Arg Leu Ala Thr Ala Ser Gly Ser Glu Ala
305                 310                 315                 320
Ala Thr Ala Gly Pro Ser Thr Ala Gly Ser Ser Cys Pro Ala Ser
                325                 330                 335
Val Val Leu Ala Ala Ala Ala Gln Ala Ala Ala Ser Gln Ser
            340                 345                 350
Pro Pro Lys Asp Met Val Asp Leu Asn Arg Arg Ile Phe Val Ala Ala
        355                 360                 365
Leu Asn Lys Leu Glu
    370

<210> SEQ ID NO 7
<211> LENGTH: 75
<212> TYPE: PRT
<213> ORGANISM: Human cytomegalovirus

<400> SEQUENCE: 7

Met Ser Asn Thr Ala Pro Gly Pro Thr Val Ala Asn Lys Arg Asp Glu
1               5                   10                  15
Lys His Arg His Val Asn Val Val Leu Glu Leu Pro Thr Glu Ile
                20                  25                  30
Ser Glu Ala Thr His Pro Val Leu Ala Thr Met Leu Ser Lys Tyr Thr
            35                  40                  45
Arg Met Ser Ser Leu Phe Asn Asp Lys Cys Ala Phe Lys Leu Asp Leu
        50                  55                  60
Leu Arg Met Val Ala Val Ser Arg Thr Arg Arg
65                  70                  75

<210> SEQ ID NO 8
<211> LENGTH: 27
<212> TYPE: DNA
<213> ORGANISM: artificial
<220> FEATURE:
<223> OTHER INFORMATION: primer

<400> SEQUENCE: 8
ggatccatga gtttgcagtt tatcggt                                           27

<210> SEQ ID NO 9
<211> LENGTH: 27
<212> TYPE: DNA
<213> ORGANISM: artificial
<220> FEATURE:
<223> OTHER INFORMATION: primer

<400> SEQUENCE: 9
gctagcttcc tccgtgttct taatctt                                           27

<210> SEQ ID NO 10
<211> LENGTH: 27
<212> TYPE: DNA
<213> ORGANISM: artificial
<220> FEATURE:
<223> OTHER INFORMATION: primer

<400> SEQUENCE: 10
```

```
ggatccatgg agtcgcgcgg tcgccgt                                              27

<210> SEQ ID NO 11
<211> LENGTH: 27
<212> TYPE: DNA
<213> ORGANISM: artificial
<220> FEATURE:
<223> OTHER INFORMATION: primer

<400> SEQUENCE: 11
gctagcacct cggtgctttt tgggcgt                                              27

<210> SEQ ID NO 12
<211> LENGTH: 27
<212> TYPE: DNA
<213> ORGANISM: artificial
<220> FEATURE:
<223> OTHER INFORMATION: primer

<400> SEQUENCE: 12
ggatccatgg atcgcaagac gcgcctc                                              27

<210> SEQ ID NO 13
<211> LENGTH: 27
<212> TYPE: DNA
<213> ORGANISM: artificial
<220> FEATURE:
<223> OTHER INFORMATION: primer

<400> SEQUENCE: 13
gctagcgccg cacttttgct tcttggt                                              27

<210> SEQ ID NO 14
<211> LENGTH: 27
<212> TYPE: DNA
<213> ORGANISM: artificial
<220> FEATURE:
<223> OTHER INFORMATION: primer

<400> SEQUENCE: 14
gaattcatgt cgcaccctct gagtgct                                              27

<210> SEQ ID NO 15
<211> LENGTH: 27
<212> TYPE: DNA
<213> ORGANISM: artificial
<220> FEATURE:
<223> OTHER INFORMATION: primer

<400> SEQUENCE: 15
gctagcctcg agcttattga gcgcagc                                              27

<210> SEQ ID NO 16
<211> LENGTH: 27
<212> TYPE: DNA
<213> ORGANISM: artificial
<220> FEATURE:
<223> OTHER INFORMATION: primer

<400> SEQUENCE: 16
ggatccatgg gtgccgaact ctgcaaa                                              27

<210> SEQ ID NO 17
<211> LENGTH: 27
<212> TYPE: DNA
```

```
<213> ORGANISM: artificial
<220> FEATURE:
<223> OTHER INFORMATION: primer

<400> SEQUENCE: 17
gaattcaaag ggcaaggagg cggcggg                                              27

<210> SEQ ID NO 18
<211> LENGTH: 27
<212> TYPE: DNA
<213> ORGANISM: artificial
<220> FEATURE:
<223> OTHER INFORMATION: primer

<400> SEQUENCE: 18
ggatccatgt ctaacaccgc gccggga                                              27

<210> SEQ ID NO 19
<211> LENGTH: 24
<212> TYPE: DNA
<213> ORGANISM: artificial
<220> FEATURE:
<223> OTHER INFORMATION: primer

<400> SEQUENCE: 19
gaattcgcgc cgggtgcgcg acac                                                 24
```

METHOD FOR ASSESSING RISK OF HUMAN CYTOMEGALOVIRUS ACTIVE INFECTION IN BODY AND RELATED KIT

CROSS-REFERENCE TO RELATED APPLICATIONS

This application claims priority under 35 U.S.C. § 371 to Patent Cooperation Treaty application PCT/CN2016/072094, filed Jan. 26, 2016, which claims the benefit of Chinese Patent Application No. 201510067190.3, filed Feb. 9, 2015, the entire contents of which are incorporated herein by reference.

SEQUENCE LISTING

This application incorporates in its entirety the Sequence Listing entitled "IEC150012PCT-SEQLIST" (27,316 kilobytes), which was created on Feb. 9, 2015 and filed electronically herewith.

TECHNICAL FIELD

The invention belongs to the fields of medicine and immunology, particularly, the field of immunological diagnosis. In particular, the invention discloses a method for assessing whether a subject is at risk of developing human cytomegalovirus (HCMV) active infection and a kit therefore. The method comprises the steps of: (1) determining the level of an antibody against a HCMV protein in a body fluid sample from the subject; and (2) comparing the level with a predetermined reference value, wherein if the level is below the predetermined reference value, the subject is determined to be at risk of developing HCMV active infection. In addition, the invention also discloses a method for screening a candidate drug which is capable of improving the ability of a subject to resist human cytomegalovirus (HCMV) active infection, and a kit therefore.

BACKGROUND ART

Human Cytomegalovirus (HCMV), a DNA virus, is a human pathogen belonging to the family of Herpesviridae. Cytomegalovirus infection is widely present worldwide. Once infected by HCMV, human body will carry a latent virus for a lifetime, and the latent virus may be activated occasionally.

Most of HCMV infections are inapparent infections, but would result in serious or even lethal diseaeses in fetuses and immunocompromised populations. For example, if congenital CMV infection occurs in fetus (i.e., CMV passes through blood-placenta barrier and infects intrauterine fetus), it will result in serious clinical hazards, including fetal death, abortion, birth defects, and the like [1,2] (Dollard S C, Grosse S D, Ross D S. New estimates of the prevalence of neurological and sensory sequelae and mortality associated with congenital cytomegalovirus infection. Rev Med Virol. 2007, 17: 355-363; Jiang Yi. Congenital cytomegalovirus infection: transmission from mother to infant and diagnosis. CHINESE JOURNAL OF NEONATOLOGY. 2009, 24:261-265). Most of studies show that CMV is a congenital infectious pathogen in neonate, which is the most common and the most harmful pathogen in the world, and the most important cause for sensorineural hearing loss and neural development retardation in children. In immunocompromised populations, such as organ transplant patients and AIDS patients, HCMV will activate infection and cause systemic complication.

Therefore, it is necessary to screen pregnant women susceptible to congenital CMV infection or immunosuppressed patients susceptible to human cytomegalovirus (HCMV) active infection, in order to employ intervention measures prior to occurrence of harmfulness.

Researchers believed in the past that antibody-negative pregnant mothers were susceptible to primary cytomegalovirus infection in pregnancy, and therefore it was quite possible to result in congenital infection in fetus [3,4] (Fowler K B, Stagno S, Pass R F, et al. The outcome of congenital cytomegalovirus infection in relation to maternal antibody status. N Engl J Med, 1992, 326: 663-667.2; Kenneson A, Cannon M J. Review and meta-analysis of the epidemiology of congenital cytomegalovirus infection. Rev Med Virol, 2007, 17: 253-276); the newborns delivered by antibody-positive pregnant mothers rarely had serious clinical outcomes. However, in recent years, the results of the systemic researches conducted in some developing countries where CMV is highly prevalent have gradually reversed this erroneous cognition. The results of these systemic researches demonstrates that most of the children with hearing disorder in developing countries are resulted from transmission from CMV antibody-positive mother to infant [5-7] (Manicklal S, Emery V C, Lazzarotto T, Boppana S B, Gupta R K. The "silent" global burden of congenital cytomegalovirus. Clin Microbiol Rev. 2013, 26: 86-102; Mussi-Pinhata M M, Yamamoto A Y, Moura Brito R M, de Lima Isaac M, de Carvalho e Oliveira P F, Boppana S, Britt W J. Birth prevalence and natural history of congenital cytomegalovirus infection in a highly seroimmune population. Clin Infect Dis. 2009, 49:522-528; Yamamoto A Y, Mussi-Pinhata M M, Isaac Mde L, Amaral F R, Carvalheiro C G, Aragon D C, Manfredi A K, Boppana S B, Britt W J. Congenital cytomegalovirus infection as a cause of sensorineural hearing loss in a highly immune population. Pediatr Infect Dis J. 2011, 30:1043-1046). Some studies show that intrauterine infection in the fetus of pregnant women who are seropositive for CMV prior to pregnancy is associated with maternal recurrent infection (also called "reactivation" or "reinfection") by CMV during pregnancy [8,9] (Boppana S B, Rivera L B, Fowler K B, Mach M, Britt W J. Intrauterine transmission of cytomegalovirus to infants of women with pre-conceptional immunity. N Engl J Med. 2001, 344: 1366-1371; Ross S A, Arora N, Novak Z, Fowler K B, Britt W J, Boppana S B. Cytomegalovirus reinfections in healthy seroimmune women. J Infect Dis. 2010, 201: 386-389). Now, CMV-IgM and IgG antibody assays are commonly used in various countries to determine prenatal CMV active infection in pregnant women. IgM and IgG antibody assays are of certain value for diagnosis of primary infection in antibody-negative pregnant women prior to pregnancy. However, when IgM and IgG antibody assays are used to diagnose reinfection in antibody-positive pregnant women prior to pregnancy, both the sensitivity and specificity have been questioned a lot [10,11] (He Xiaozhou, Wang Xiaofang, Wang Shiwen; Research Progress in Congenital Cytomegalovirus Infection and Detection Method thereof. Chinese Journal of Virology. 2012, 28:73-77; Ross S A, Novak Z, Pati S, Boppana S B. Overview of the diagnosis of cytomegalovirus infection. Infect Disord Drug Targets. 2011, 11:466-474).

Therefore, there is need in this field to develop new methods with high sensitivity and specificity so as to accurately and effectively assess whether a subject is at risk of developing human cytomegalovirus (HCMV) active infection.

CONTENTS OF INVENTION

In the invention, unless otherwise specified, the scientific and technical terms used herein have the meanings as generally understood by a person skilled in the art. Moreover, the laboratory operations of cell culture, molecular genetics, nucleic acid chemistry and immunology used herein are the routine operations widely used in the corresponding fields. Meanwhile, in order to better understand the invention, the definitions and explanations of the relevant terms are provided as follows.

As used herein, the term "cytomegalovirus active infection" refers to primary infection with CMV in a subject that has never been infected with CMV; and recurrent infection with CMV or activation of a latent CMV virus (also called "reinfection" or "reactivation") in a subject that has been infected with CMV before (who generally carries a latent virus, and is generally positive in serological examination result). Typical manifestation of cytomegalovirus active infection is the generation of a significant immune response to the infected cytomegalovirus (for the first time or again) in a subject, resulting in a significantly increased level of an antibody against a CMV protein in the subject. Therefore, cytomegalovirus active infection is also called a virus event. In general, if the level of an antibody against a CMV protein in a subject increases by 4 folds or more, it can be determined that the subject has cytomegalovirus active infection (or, a virus event).

As used herein, the term "pp150" or "pp150 protein" refers to a phosphorylated protein in CMV virus envelope layer, also called UL32 protein. pp150 protein is one of the high-abundant CMV proteins, is closely associated with assembly and secretion of virus, is conservative among various CMV strains, and has good immunoreactivity with CMV-infected serum [12] (Jahn G, Scholl B C, Traupe B, Fleckenstein B. The two major structural phosphoproteins (pp65 and pp150) of human cytomegalovirus and their antigenic properties. J Gen Virol. 1987, 68:1327-1337). Since pp150 has good conservatism and immuno-reactivity, it has been used in the detection of CMV-IgG antibodies now [13] (Plachter B, Wieczorek L, Scholl B C, Ziegelmaier R, Jahn G. Detection of cytomegalovirus antibodies by an enzyme-linked immunosorbent assay using recombinant polypeptides of the large phosphorylated tegument protein pp150. J Clin Microbiol. 1992, 30:201-206). Positive result in serologic test (i.e., an antibody against pp150 is present in serum) indicates that the individual has been infected by CMV, and an immune response to pp150 has been generated. However, the correlation between the level of an antibody against pp150 with the probability of developing cytomegalovirus active infection in a subject has never been taught or suggested.

The amino acid sequence of pp150 protein is well known by a person skilled in the art, and its typical example can be found in, for example, GenBank Accession No. ACL51112. As used herein, when the amino acid sequence of pp150 protein is mentioned, it is described by the sequence set forth in SEQ ID NO: 1. For example, the expression "aa 861-1048 of pp150" or "amino acids from positions 861 to 1048 of pp150" refers to the amino acid residues from positions 861 to 1048 of the polypeptide set forth in SEQ ID NO: 1. However, a person skilled in the art understands that in the amino acid sequence of pp150, mutation or variation (including, but not limited to, substitution, deletion and/or addition, for example, pp150 from different isolated strains of CMV virus) may occur naturally or be introduced artificially, without affecting the biological function thereof. Therefore, in the invention, the term "pp150" should include all such sequences, including, for example, the sequence set forth in SEQ ID NO: 1 and its natural or artificial variants. Moreover, when a sequence fragment of pp150 is described, it includes not only a sequence fragment of SEQ ID NO: 1, but also the corresponding sequence fragment of its natural or artificial variants. For example, the expression "aa 861-1048 of pp150" or "the amino acid residues from positions 861 to 1048 of pp150" includes the amino acid residues from positions 861 to 1048 of SEQ ID NO: 1, and the corresponding fragment of its variants (natural or artificial).

As used herein, the term "pp28" or "pp28 protein" refers to a phosphorylated protein in CMV virus envelope layer, also called UL99 protein (Gambarino S, Callea S, Rizzo G, Montanari P, Loiacono E, Bergallo M. Evaluation of UL99 transcript as a target for antiviral treatment efficacy. J Virol Methods. 2014, 207:104-9; John Paul Tomtishen III. Human cytomegalovirus tegument proteins (pp65, pp71, pp150, pp28). Virol J. 2012, 9:22).

The amino acid sequence of pp28 protein is well known by a person skilled in the art, and its typical example may be found in, for example, GenBank Accession No. ACL51167.1. As used herein, when the amino acid sequence of pp28 protein is mentioned, it is described by the sequence set forth in SEQ ID NO: 3. For example, the expression "aa 1-190 of pp28" or "the amino acid residues from positions 1 to 190 of pp28" refers to the amino acid residues from positions 1 to 190 of the polypeptide set forth in SEQ ID NO: 3. However, a person skilled in the art understands that in the amino acid sequence of pp28, mutation or variation (including, but not limited to, substitution, deletion and/or addition, for example, pp28 from different isolated strains of CMV virus) may occur naturally or be introduced artificially, without affecting the biological function thereof. Therefore, in the invention, the term "pp28" should include all such sequences, including, for example, the sequence set forth in SEQ ID NO: 3 and its natural or artificial variants. Moreover, when a sequence fragment of pp28 is described, it includes not only a sequence fragment of SEQ ID NO: 3, but also the corresponding sequence fragment of its natural or artificial variants. For example, the expression "aa 1-190 of pp28" or "the amino acid residues from positions 1 to 190 of pp28" includes the amino acid residues from positions 1 to 190 of SEQ ID NO: 3, and the corresponding fragment of its variants (natural or artificial).

As used herein, the term "pp65" or "pp65 protein" refers to a phosphorylated protein in CMV virus envelope layer, also called UL83 protein (Jahn G, Scholl B C, Traupe B, Fleckenstein B. The two major structural phosphoproteins (pp65 and pp150) of human cytomegalovirus and their antigenic properties. J Gen Virol. 1987, 68:1327-1337; John Paul Tomtishen III. Human cytomegalovirus tegument proteins (pp65, pp71, pp150, pp28). Virol J. 2012, 9:22).

The amino acid sequence of pp65 protein is well known by a person skilled in the art, and its typical example may be found in, for example, GenBank Accession No. ACL51152.1. As used herein, when the amino acid sequence of pp65 protein is mentioned, it is described by the sequence set forth in SEQ ID NO: 4. For example, the expression "aa 1-561 of pp65" or "the amino acid residues from positions 1 to 561 of pp65" refers to the amino acid residues from positions 1 to 561 of the polypeptide set forth in SEQ ID NO: 4. However, a person skilled in the art understands that in the amino acid sequence of pp65, mutation or variation (including, but not limited to, substitution, deletion and/or addition, for example, pp65 from different isolated strains of CMV virus) may occur naturally or be introduced artificially, without affecting the biological function thereof. Therefore, in the invention, the term "pp65" should include all such sequences, including, for example, the sequence set forth in SEQ ID NO: 4 and its natural or artificial variants. Moreover, when a sequence fragment of pp65 is described, it includes not only a sequence fragment of SEQ ID NO: 4, but also the corresponding sequence fragment of its natural or artificial variants. For example, the expression "aa 1-561 of pp65" or "the amino acid residues from positions 1 to 561 of pp65" includes the amino acid residues from positions 1 to 561 of SEQ ID NO: 4, and the corresponding fragment of its variants (natural or artificial).

As used herein, the term "gp52" or "gp52 protein" refers to a phosphorylated protein in CMV virus envelope layer, also called UL44 protein (Strang B L, Boulant S, Chang L, et al. Human cytomegalovirus UL44 concentrates at the periphery of replication compartments, the site of viral DNA synthesis[J]. Journal of virology, 2012, 86: 2089-2095; Sinigalia E, Alvisi G, Segré C V, et al. The human cytomegalovirus DNA polymerase processivity factor UL44 is modified by SUMO in a DNA-dependent manner[J]. PLoS One, 2012, 7(11): e49630).

The amino acid sequence of gp52 protein is well known by a person skilled in the art, and its typical example can be found in, for example, GenBank Accession No. ACL51123.1. As used herein, when the amino acid sequence of gp52 protein, it is described by the sequence set forth in SEQ ID NO: 5. For example, the expression "aa 1-433 of gp52" or "the amino acid residues from positions 1 to 433 of gp52" refers to the amino acid residues from positions 1 to 433 of the polypeptide set forth in SEQ ID NO: 5. However, a person skilled in the art understands that in the amino acid sequence of gp52, mutation or variation (including, but not limited to, substitution, deletion and/or addition, for example, gp52 from different isolated strains of CMV virus) may occur naturally or be introduced artificially, without affecting the biological function thereof. Therefore, in the invention, the term "gp52" should include all such sequences, including, for example, the sequence set forth in SEQ ID NO: 5 and its natural or artificial variants. Moreover, when a sequence fragment of gp52 is described, it includes not only a sequence fragment of SEQ ID NO: 5, but also the corresponding sequence fragment of its natural or artificial variants. For example, the expression "aa 1-433 of gp52" or "the amino acid residues from positions 1 to 433 of gp52" includes the amino acid residues from positions 1 to 433 of SEQ ID NO: 5, and the corresponding fragment of its variants (natural or artificial).

As used herein, the term "pp38" or "pp38 protein" refers to a phosphorylated protein in CMV virus envelope layer, also called UL80.5 protein (Loveland A N, Nguyen N L, Brignole E J, et al. The amino-conserved domain of human cytomegalovirus UL80a proteins is required for key interactions during early stages of capsid formation and virus production. Journal of virology, 2007, 81:620-628; Wood L J, Baxter M K, Plafker S M, et al. Human cytomegalovirus capsid assembly protein precursor (pUL80. 5) interacts with itself and with the major capsid protein (pUL86) through two different domains. Journal of virology, 1997, 71: 179-190).

The amino acid sequence of pp38 protein is well known by a person skilled in the art, and its typical example can be found in, for example, GenBank Accession No. ACL51150.1. As used herein, when the amino acid sequence of pp38 protein is mentioned, it is described by the sequence set forth in SEQ ID NO: 6. For example, the expression "aa 1-373 of pp38" or "the amino acid residues from positions 1 to 373 of pp38" refers to the amino acid residues from positions 1 to 373 of the polypeptide set forth in SEQ ID NO: 6. However, a person skilled in the art understands that in the amino acid sequence of pp38, mutation or variation (including, but not limited to, substitution, deletion and/or addition, for example, pp38 from different isolated strains of CMV virus) may occur naturally or be introduced artificially, without affecting the biological function thereof. Therefore, in the invention, the term "pp38" should include all such sequences, including, for example, the sequence set forth in SEQ ID NO: 6 and its natural or artificial variants. Moreover, when a sequence fragment of pp38 is described, it includes not only a sequence fragment of SEQ ID NO: 6, but also the corresponding sequence fragment of its natural or artificial variants. For example, the expression "aa 1-373 of pp38" or "the amino acid residues from positions 1 to 373 of pp38" includes the amino acid residues from positions 1 to 373 of SEQ ID NO: 6, and the corresponding fragment of its variants (natural or artificial).

As used herein, the term "UL48a" or "UL48a protein" refers to a capsid protein of CMV virus (Baldick C J, Shenk T. Proteins associated with purified human cytomegalovirus particles. Journal of virology, 1996, 70: 6097-6105).

The amino acid sequence of UL48a protein is well known by a person skilled in the art, and its typical example can be found in, for example, GenBank Accession No. ACL51128.1. As used herein, when the amino acid sequence of UL48a protein, it is described by the sequence set forth in SEQ ID NO: 7. For example, the expression "aa 1-75 of UL48a" or "the amino acid residues from positions 1 to 75 of UL48a" refers to the amino acid residues from positions 1 to 75 of the polypeptide set forth in SEQ ID NO: 7. However, a person skilled in the art understands that in the amino acid sequence of UL48a, mutation or variation (including, but not limited to, substitution, deletion and/or addition, for example, UL48a from different isolated strains of CMV virus) may occur naturally or be introduced artificially, without affecting the biological function thereof. Therefore, in the invention, the term "UL48a" should include all such sequences, including, for example, the sequence set forth in SEQ ID NO: 7 and its natural or artificial variants. Moreover, when a sequence fragment of UL48a is described, it includes not only a sequence fragment of SEQ ID NO: 7, but also the corresponding sequence fragment of its natural or artificial variants. For example, the expression "aa 1-75 of UL48a" or "the amino acid residues from positions 1 to 75 of UL48a" includes the amino acid residues from positions 1 to 75 of SEQ ID NO: 7, and the corresponding fragment of its variants (natural or artificial).

As used herein, the term "IE1 protein" refers to an immediate early protein of CMV virus (Torres L, Tang Q. Immediate-Early (IE) gene regulation of cytomegalovirus: IE1- and pp71-mediated viral strategies against cellular defenses[J]. Virologica Sinica, 2014, 29: 343-352; McVoy M A. Cytomegalovirus vaccines. Clinical infectious diseases, 2013, 57: S196-S199).

The amino acid sequence of IE1 protein is well known by a person skilled in the art, and its typical example may be found in, for example, GenBank Accession No. ACL51183.1.

According to the invention, the expression "a corresponding sequence fragment" or "a corresponding fragment" refers to a fragment located at an equivalent position in the sequences for alignment, when the sequences are subjected to optimal alignment (i.e., the sequences are aligned to obtain the highest percent identity).

As used herein, the term "identity" refers to the match degree between two polypeptides or between two nucleic acids. When two sequences for comparison have the same base or amino acid monomer sub-unit at a certain site (e.g., each of two DNA molecules has an adenine at a certain site, or each of two polypeptides has a lysine at a certain site), the two molecules are identical at the site. The percent identity between two sequences is a function of the number of identical sites shared by the two sequences over the total number of sites for comparison×100. For example, if 6 of 10 sites of two sequences are matched, these two sequences have an identity of 60%. For example, DNA sequences: CTGACT and CAGGTT share an identity of 50% (3 of 6 sites are matched). Generally, the comparison of two sequences is conducted in a manner to produce maximum identity. Such alignment can be conducted by, for example, using a computer program such as Align program (DNAstar, Inc.) which is based on the method of Needleman, et al. (J. Mol. Biol. 48:443-453, 1970). The percent identity between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percentage of identity between two amino acid sequences can be determined by the algorithm of Needleman and Wunsch (J. Mol. Biol. 48:444-453 (1970)) which has been incorporated into the GAP program in the GCG software package using either a Blossum 62 matrix or a PAM250 matrix, and a gap weight of 16, 14, 12, 10, 8, 6, or 4 and a length weight of 1, 2, 3, 4, 5, or 6.

As used herein, the term "conservative substitution" refers to amino acid substitutions which would not disadvantageously affect or change the essential properties of a protein/polypeptide comprising an amino acid sequence. For example, a conservative substitution may be introduced by standard techniques known in the art such as site-directed mutagenesis and PCR-mediated mutagenesis. Conservative amino acid substitutions include substitutions wherein an amino acid residue is substituted with another amino acid residue having a similar side chain, for example, a residue physically or functionally similar (such as, having similar size, shape, charge, chemical property including the capability of forming covalent bond or hydrogen bond, etc.) to the corresponding amino acid residue. The families of amino acid residues having similar side chains have been defined in the art. These families include amino acids having alkaline side chains (for example, lysine, arginine and histidine), amino acids having acidic side chains (for example, aspartic acid and glutamic acid), amino acids having uncharged polar side chains (for example, glycine, asparagine, glutamine, serine, threonine, tyrosine, cysteine, tryptophan), amino acids having nonpolar side chains (for example, alanine, valine, leucine, isoleucine, proline, phenylalanine, methionine), amino acids having β-branched side chains (such as threonine, valine, isoleucine) and amino acids having aromatic side chains (for example, tyrosine, phenylalanine, tryptophan, histidine). Therefore, a corresponding amino acid residue is preferably substituted with another amino acid residue from the same side-chain family. Methods for identifying amino acid conservative substitutions are well known in the art (see, for example, Brummell et al., Biochem. 32: 1180-1187 (1993); Kobayashi et al., Protein Eng. 12(10): 879-884 (1999); and Burks et al., Proc. Natl. Acad. Sci. USA 94: 412-417 (1997), which are incorporated herein by reference).

As used herein, the term "antibody" generally refers to an immunoglobulin molecule consisting of two pairs of polypeptide chains (each has a light (L) chain and a heavy (H) chain). Light chains of an antibody may be classified into κ and λ light chain. Heavy chains may be classified into μ, δ, γ, α and ε, which define isotypes of an antibody as IgM, IgD, IgG, IgA and IgE, respectively. In a light chain and a heavy chain, a variable region is linked to a constant region via a "J" region of about 12 or more amino acids, and a heavy chain further comprises a "D" region of about 3 or more amino acids. Each heavy chain consists of a heavy chain variable region ($V_H$) and a heavy chain constant region ($C_H$). A heavy chain constant region consists of 3 domains ($C_H1$, $C_H2$ and $C_H3$). Each light chain consists of a light chain variable region ($V_L$) and a light chain constant region ($C_L$). A light chain constant region consists of a domain $C_L$. The constant region of an antibody can mediate the binding of an immunoglobulin to a host tissue or factor, including various cells (e.g., effector cells) of an immune system and the first component (C1q) of classical complement system. $V_H$ and $V_L$ region can also be divided into hypervariable regions (called complementary determining regions (CDR)), which are interspaced by relatively conservative regions (called framework region (FR)). Each $V_H$ and $V_L$ consists of 3 CDRs and 4 FRs in the following order: FR1, CDR1, FR2, CDR2, FR3, CDR3, FR4 from N-terminal to C-terminal. The variable region ($V_H$ and $V_L$) of each heavy/light chain pair forms an antigen binding site, respectively. Distribution of amino acids in various regions or domains follows the definition in Kabat Sequences of Proteins of Immunological Interest (National Institutes of Health, Bethesda, Md. (1987 and 1991)), or Chothia & Lesk (1987) J. Mol. Biol. 196: 901-917; Chothia et al., (1989) Nature 342:878-883. The term "antibody" is not restricted by any specific method for producing antibodies. For example, antibodies include particularly, recombinant antibodies, monoclonal antibodies and polyclonal antibodies. Antibodies may be of different antibody isotypes, for example, IgG (e.g., IgG1, IgG2, IgG3 or IgG4 subtype), IgA1, IgA2, IgD, IgE or IgM antibody.

As used herein, the term "level of an antibody" refers to the amount of an antibody capable of reacting with human cytomegalovirus protein (for example, pp150/pp28), which, for example, may be determined by any relative or absolute quantitative means (including, but not limited to any detection means capable of obtaining the level of an antibody, such as ELISA, colloidal gold method or chemiluminescence method), and for example, may be expressed as strength of antibody-antigen reaction, an antibody titer, an antibody quantitative detection value (for example, an antibody absolute quantity).

As used herein, the term "antibody titer" refers to the minimum concentration (also called the maximum dilution degree) of an antibody-containing sample (for example, serum, an antibody solution) needed for recognizing an antigen (or an antigenic fragment thereof, for example, an antigen epitope) that is specifically bound by the antibody; which is generally expressed as the maximum dilution degree that can still result in a positive result. Methods for determining the antibody titer of a certain sample are well known by a person skilled in the art, for example, the antibody titer of a sample can be determined by ELISA method generally. The ELISA method, for example, can comprise the following steps of: (1) coating a microwell plate with an antigen protein (or an antigenic fragment thereof) that is specifically bound by an antibody, as a coating antigen; (2) subjecting an antibody-containing sample (for example, serum) to serial dilution; (3) adding the diluted samples to the wells in the microwell plate coated in step (1); and (4) determining the presence of the antibody binding to the coating antigen in the microwell plate (for example, using an antibody against the antibody, or a labelled antigen protein, etc.), and therefore determining the maximum dilution degree of the sample that can still result in a positive result (i.e., the antibody titer of the sample).

As used herein, the term "absolute quantity of an antibody" refers to the quantity of an antibody expressed by a biological activity of the antibody, which is generally expressed as international unit IU/ml or its variant form (for example, IU/L, mIU/ml, etc.). Methods for determining the absolute quantity of an antibody in a certain sample are well known by a person skilled in the art. For example, the antibody reactivity of an antibody-containing sample (for example, serum) is compared with the antibody reactivity of a standard sample comprising an antibody in a known amount, so as to determine the absolute quantity of the antibody in the sample. For example, the method can comprise the following steps of: (1) determining the antibody reactivity of the serial diluents of a standard sample by ELISA, and plotting an antibody content-antibody reactivity standard curve; (2) determining the antibody reactivity of an antibody-containing sample (or its diluent); and (3) converting the antibody reactivity of the sample (or its diluent) into the absolute quantity of the antibody contained in the sample by using the standard curve.

As used herein, the term "antibody reactivity" refers to the ability of an antibody to specifically recognize an antigen, which can be easily determined by immunologic assay (for example, ELISA). For example, antibody reactivity can be expressed as OD value obtained by the ELISA assay for determining antigen-antibody binding.

As used herein, the term "antigenic fragment" refers to a fragment of an antigen protein that retains the ability of specifically binding to an antibody that specifically recognizes the antigen protein. A person skilled in the art can obtain such antigenic fragments by conventional technical means. For example, the method can comprise the following steps of: (1) preparing various fragments of an antigen protein (for example, by genetic engineering technology, chemical synthetic technology, enzymolysis of antigen protein, etc.); and (2) determining whether the prepared fragments retain the ability of specifically binding to an antibody that specifically recognizes the antigen protein, by immunologic assay (for example, ELISA), thereby screening the antigenic fragments of the antigen protein.

As used herein, the term "immunologic assay" refers to an assay utilizing the specific interaction/binding affinity between an antigen and an antibody, which is generally used to determine the presence or level of a specific antigen or antibody in a sample. Such an immunologic assay is well known for a person skilled in the art, including, but not limited to ELISA assay, Western blot, surface plasmon resonance, Elispot assay, and the like.

As used herein, the term "specific binding" refers to a non-random binding reaction between two molecules, such as the reaction between an antibody and an antigen that the antibody is directed to. In some embodiments, an antibody specifically binding to a certain antigen (or an antibody having specificity for a certain antigen) refers to an antibody binding to the antigen with an affinity ($K_D$) of below about $10^{-5}$ M, for example, below about $10^{-6}$ M, $10^{-7}$ M, $10^{-8}$ M, $10^{-9}$ M or $10^{-10}$ M or less.

As used herein, the term "$K_D$" refers to a dissociation equilibrium constant of a specific antibody-antigen interaction, which is used to describe the binding affinity between an antibody and an antigen. The lower the dissociation equilibrium constant is, the tighter the antibody-antigen binding is, and the higher the affinity between the antibody and the antigen is. In general, an antibody binds to an antigen with a dissociation equilibrium constant ($K_D$) of below about $10^{-5}$ M, for example, below about $10^{-6}$ M, $10^{-7}$ M, $10^{-8}$ M, $10^{-9}$ M or $10^{-10}$ M or less, for example, determined by surface plasmon resonance (SPR) in BIA-CORE instrument.

As used herein, the term "subject" includes, but is not limited to, various animal, particularly mammal, for example, human.

As used herein, the term "body fluid sample" refers to a sample comprising the body fluid or a fraction thereof obtained from a subject. A body fluid sample may comprise or be a body fluid (or a fraction thereof) directly obtained from a subject, or may comprise or be a treated body fluid (for example, an isolated body fluid fraction), and optionally comprise other components, such as a buffer, an anticoagulant, and a diluent. A variety of body fluids or fractions thereof obtained from a subject are well known by a person skilled in the art, including, but not limited to, blood, serum, plasma, urine, saliva, etc.

As used herein, the term "a reagent capable of determining the level of an antibody against a HCMV protein" refers to a reagent capable of quantitatively and semi-quantitatively determining the level of an antibody against a HCMV protein in a sample. In general, it is particularly preferred that the reagent can determine the level of an antibody against a HCMV protein in a sample by immunologic assay. The employment of immunologic assay is particularly favorable, because it utilizes the specific interaction/binding affinity between an antigen and an antibody. Therefore, as long as a reagent retains its antigenicity of reacting with an antibody (for example, an antibody against a HCMV protein), the reagent can determine the level of an antibody against a HCMV protein in a sample by immunologic assay (that is, the reagent can be used as a reagent capable of determining the level of an antibody against a HCMV protein). Various reagents that retain the antigenicity of reacting with an antibody (for example, an antibody against a HCMV protein) can be readily envisaged and obtained by a person skilled in the art, including, but not limited to, an antigen protein itself (in the present application, a HCMV protein) or an antigenic fragment thereof, a fusion protein comprising the antigen protein (in the present application, a HCMV protein) or an antigenic fragment thereof, and any combination thereof.

As used herein, the term "test animal" refers to an animal for use in experiment, which is generally a non-human mammal, such as a model animal (for example, mouse, rat, rabbit, primate). A person skilled in the art can select a variety of suitable test animals depending on the practical need in experiment.

As used herein, the term "relative risk (RR)", also called risk ratio, refers to the ratio of the probability of developing a disease (in the invention, HCMV active infection) in a subject having a certain parameter or index (in the invention, an antibody level, for example, the level of an antibody against pp150 or pp28) below the reference value, to the probability of developing a disease in a subject having the parameter or index above the reference value. Relative risk is an index reflecting the correlation strength between a parameter/index and development of a disease. It is generally believed that when RR is 1.0-1.1, there is no correlation between the parameter/index and the disease; when RR is 1.2-1.4, there is a weak correlation between the parameter/index and the disease; when RR is 1.5-2.9, there is a moderate correlation between the parameter/index and the disease; when RR is 3.0-9.9, there is a strong correlation between the parameter/index and the disease; when RR is greater than 10, there is a very strong correlation between the parameter/index and the disease.

As used herein, the term "Youden index" refers to an index for evaluating validity of a screening test/diagnostic test. When the false negative rate (omission diagnose rate) and false positive rate (mistake diagnose rate) of a screening/diagnostic test are of equal significance, a Youden index is the sum of sensitivity and specificity of the test minus 1. Youden index represents the total ability of a screening/diagnostic test to identify true patients and non-patients. A larger Youden index value indicates a better effect of a screening/diagnostic test and a higher validity.

One technical problem to be solved by the invention is to provide a method for accurately and effectively assessing the probability of developing cytomegalovirus active infection in a subject (such as a pregnant woman, an organ transplant patient, and a HIV-infected person), which can provide support for employing intervention measures in order to reduce the probability of congenital cytomegalovirus infection; and can direct clinical medication to prevent complications in patients.

For this purpose, the inventor expressed and purified the test proteins commonly used in the research on diagnosis of cytomegalovirus [14] (Plachter B, Wieczorek L, Scholl B C, Ziegelmaier R, Jahn G. Detection of cytomegalovirus antibodies by an enzyme-linked immunosorbent assay using recombinant polypeptides of the large phosphorylated tegument protein pp150. J Clin Microbiol. 1992, 30:201-206.), i.e., pp150 (UL32), pp28 (UL99), pp38 (UL80.5), UL48a, gp52 (UL44) and pp65 (UL83); and then tried to use the antigens to establish methods and platforms for assessing the probability of developing cytomegalovirus active infection in a subject. After a series of studies and experiments, the inventor found that the level of an antibody against pp150 (UL32) and/or pp28 (UL99) in serum from a subject (which may be, for example, determined by ELISA using pp150 (UL32) and/or pp28 (UL99) as coating antigen) can effectively and reliably reflect the probability of developing cytomegalovirus active infection in the subject. Therefore, the inventor, based on the detection of the level of an antibody against pp150 (UL32) and/or pp28 (UL99), has successfully established methods and platforms for assessing the probability of developing cytomegalovirus active infection in a subject.

Therefore, in one aspect, the invention provides a method for assessing whether a subject is at risk of developing human cytomegalovirus (HCMV) active infection, comprising the following steps of:

(1) determining the level of an antibody against a HCMV protein in a body fluid sample from the subject; and (2) comparing the level with a predetermined reference value; wherein, if the level is below the reference value, the subject is determined to be at risk of developing HCMV active infection.

In a preferred embodiment, the subject is a mammal, such as human. In a preferred embodiment, the body fluid sample is selected from blood, serum, plasma, urine and saliva.

In a preferred embodiment, the active infection is a primary infection by HCMV in a subject that has not been infected by HCMV, or, a re-infection by HCMV or activation of latent HCMV in a subject that has been infected by HCMV.

In a preferred embodiment, the HCMV protein is selected from pp150 and/or pp28.

In a preferred embodiment, the level of an antibody against a HCMV protein in the body fluid sample is determined by immunologic assay. In a further preferred embodiment, the immunologic assay is selected from ELISA assay, Western Blot, surface plasmon resonance, and Elispot assay.

In a preferred embodiment, the level refers to an antibody titer (for example, an antibody titer determined by ELISA), and the reference value is a predetermined antibody titer; or, the level refers to an antibody absolute quantity (for example, an absolute quantity expressed by IU/ml) and the reference value refers to a predetermined antibody absolute quantity (for example, an absolute quantity expressed by IU/ml).

In a preferred embodiment, in the step (1), the antibody titer of the antibody against pp150 and/or pp28 in the body fluid sample is determined by ELISA. In a preferred embodiment, the reference value is an antibody titer in a range of 40-320. In a preferred embodiment, the reference value is an antibody titer in a range of 40-160. For example, the reference value is an antibody titer of 40, 80 or 160. In a preferred embodiment, the reference value is an antibody titer of 80.

As shown in the invention, when the reference value is between 40 and 320, a subject with an antibody titer below the reference value, has a relative risk of greater than 10 for developing HCMV active infection, and the lower limit of 95% CI is greater than 7. This indicates that there is a strong correlation or a very strong correlation between the parameter (antibody titer) and HCMV active infection.

Therefore, in a preferred embodiment, the reference value is 40, and if the antibody titer of the antibody against pp150 is below or equal to 40, the subject is determined to have a relative risk of 11.2 for developing HCMV active infection, and 95% CI is 8.7-14.6. In some preferred embodiments, the reference value is set as an antibody titer of 40, and the method for predicting HCMV active infection has a sensitivity of 57.3%, a specificity of 94.7%, and a Youden index of 0.52.

In another preferred embodiment, the reference value is 80, and if the antibody titer of the antibody against pp150 is below or equal to 80, the subject is determined to have a relative risk of 10.6 for developing HCMV active infection, and 95% CI is 7.7-14.6. In some preferred embodiments, the reference value is set as an antibody titer of 80, and the method for predicting HCMV active infection has a sensitivity of 73.1%, a specificity of 85.7%, and a Youden index of 0.59.

In another preferred embodiment, the reference value is 160, and if the antibody titer of the antibody against pp150 is below or equal to 160, the subject is determined to have a relative risk of 14.8 for developing HCMV active infection, and 95% CI is 9.0-24.6. In some preferred embodiments, the reference value is set as an antibody titer of 160, and the method for predicting HCMV active infection has a sensitivity of 90.6%, a specificity of 66.4%, and a Youden index of 0.57.

In another preferred embodiment, the reference value is 320, and if the antibody titer of the antibody against pp150 is below or equal to 320, the subject is determined to have a relative risk of 23.7 for developing HCMV active infection, and 95% CI is 8.8-63.4. In some preferred embodiments, the reference value is set as an antibody titer of 320, and the method for predicting HCMV active infection has a sensitivity of 97.7%, a specificity of 40.1%, and a Youden index of 0.37.

From another point of view, a high or low antibody titer level also indicates a high or low risk of developing HCMV active infection in a subject directly. As shown in the invention, if the antibody titer of an antibody against pp150 is below or equal to 40, the risk of developing HCMV active infection in the subject can be up to 55.37%; if the antibody titer of the antibody against pp150 is below or equal to 80, the risk of developing HCMV active infection in the subject can be up to 36.98%; if the antibody titer of the antibody against pp150 is below or equal to 160, the risk of developing HCMV active infection in the subject can be up to 23.66%; if the antibody titer of the antibody against pp150 is below or equal to 320, the risk of developing HCMV active infection in the subject can be up to 15.77%. The data is obtained from a population including 1659 subjects. Although the calculated data may be slightly varied in a larger population, it can determined unambiguously that there is a strong negative correlation between the antibody titer of an antibody against pp150 and HCMV active infection, and the antibody titer can be used to determine the risk of developing HCMV active infection in a subject.

Therefore, in a preferred embodiment, the reference value is 40, and if the antibody titer of the antibody against pp150 is below or equal to 40, the subject is determined to have a probability of 55.37% for developing HCMV active infection. In another preferred embodiment, the reference value is 80, and if the antibody titer of the antibody against pp150 is below or equal to 80, the subject is determined to have a probability of 36.98% for developing HCMV active infection. In another preferred embodiment, the reference value is 160, and if the antibody titer of the antibody against pp150 is below or equal to 160, the subject is determined to have a probability of 23.66% for developing HCMV active infection. In another preferred embodiment, the reference value is 320, and if the antibody titer of the antibody against pp150 is below or equal to 320, the subject is determined to have a probability of 15.77% for developing HCMV active infection.

In a preferred embodiment, pp150 and/or an antigenic fragment thereof (for example, a fragment comprising aa 861-1048 of pp150) is used to determine the antibody titer of an antibody against pp150 in the body fluid sample by ELISA; and/or, pp28 and/or an antigenic fragment thereof is used to determine the antibody titer of an antibody against pp28 in the body fluid sample by ELISA.

In a preferred embodiment, pp150 has an amino acid sequence set forth in SEQ ID NO: 1; and/or, the antigenic fragment of pp150 has an amino acid sequence set forth in SEQ ID NO: 2; and/or, pp28 has an amino acid sequence set forth in SEQ ID NO: 3.

In another preferred embodiment, in the step (1), the absolute quantity of the antibody against pp150 and/or pp28 in the body fluid sample (for example, an absolute quantity expressed by IU/ml) is determined.

In a preferred embodiment, the absolute quantity of the antibody against pp150 and/or pp28 in the body fluid sample is determined by comparing the reactivity of the antibody against pp150 and/or pp28 in the body fluid sample with the antibody reactivity of a standard sample with a known antibody content. In a preferred embodiment, the reference value is an antibody absolute quantity in a range of 0.8-6.4 IU/ml. In a preferred embodiment, the reference value is an antibody absolute quantity in a range of 0.8-3.2 IU/ml. For example, the reference value is an antibody absolute quantity of 0.8, 1.6, or 3.2 IU/ml. In a preferred embodiment, the reference value is an antibody absolute quantity of 3.2 IU/ml.

As shown in the invention, when reference value is between 0.8 and 6.4 IU/ml, the subject has an antibody absolute quantity below the reference value has a relative risk of greater than 11 for developing HCMV active infection, and the lower limit of 95% CI is greater than 7. This indicates that there is a strong correlation or a very strong correlation between the parameter (an antibody absolute quantity) and HCMV active infection.

Therefore, in a preferred embodiment, the reference value is 0.8 IU/ml, and if the absolute quantity of the antibody against pp150 is below or equal to 0.8 IU/ml, the subject is determined to have a relative risk of 11.6 for developing HCMV active infection, and 95% CI is 7.8-17.2. In some preferred embodiments, the reference value is 0.8 IU/ml, and the method for predicting HCMV active infection has a sensitivity of 46.15%, a specificity of 96.97%, and a Youden index of 0.43.

In another preferred embodiment, the reference value is 1.6 IU/ml, and if the absolute quantity of the antibody against pp150 is below or equal to 1.6 IU/ml, the subject is determined to have a relative risk of 15.2 for developing HCMV active infection, and 95% CI is 9.5-24.3. In some preferred embodiments, the reference value is 1.6 IU/ml, and the method for predicting HCMV active infection has a sensitivity of 67.69%, a specificity of 93.34%, and a Youden index of 0.61.

In another preferred embodiment, the reference value is 3.2 IU/ml, and if the absolute quantity of the antibody against pp150 is below or equal to 3.2 IU/ml, the subject is determined to have a relative risk of 19.0 for developing HCMV active infection, and 95% CI is 9.6-37.7. In some preferred embodiments, the reference value is 3.2 IU/ml, and the method for predicting HCMV active infection has a sensitivity of 86.15%, a specificity of 81.39%, and a Youden index of 0.68.

In another preferred embodiment, the reference value is 6.4 IU/ml, and if the antibody absolute quantity of the antibody against pp150 is below or equal to 6.4 IU/ml, the subject is determined to have a relative risk of 25.2 for developing HCMV active infection, and 95% CI is 8.0-79.6. In some preferred embodiments, the reference value is 6.4 IU/ml, and the method for predicting HCMV active infection has a sensitivity of 95.38%, a specificity of 59.91%, and a Youden index of 0.55.

From another point of view, a high or low antibody absolute quantity also indicates a high or low risk of developing HCMV active infection in a subject directly. As shown in the invention, if the antibody absolute quantity of the antibody against pp150 is below or equal to 0.8 IU/ml, the risk of developing HCMV active infection in the subject can be up to 60.0%; if the antibody absolute quantity of the antibody against pp150 is below or equal to 1.6 IU/ml, the risk of developing HCMV active infection in the subject can be up to 50.0%; if the antibody absolute quantity of the antibody against pp150 is below or equal to 3.2 IU/ml, the risk of developing HCMV active infection in the subject can be up to 31.3%; if the antibody absolute quantity of the antibody against pp150 is below or equal to 6.4 IU/ml, the risk of developing HCMV active infection in the subject can be up to 19.0%. The data is obtained from a population including 726 subjects. Although the calculated data may be slightly varied in a larger population, it can determined unambiguously that there is a strong negative correlation between the antibody absolute quantity of the antibody against pp150 and HCMV active infection, and the antibody titer can be used to determine the risk of developing HCMV active infection in the subject.

Therefore, in a preferred embodiment, the reference value is 0.8 IU/ml, and if the absolute quantity of the antibody against pp150 is below or equal to 0.8 IU/ml, the subject is determined to have a probability of 60.0% for developing HCMV active infection. In a preferred embodiment, the reference value is 1.6 IU/ml, and if the absolute quantity of the antibody against pp150 is below or equal to 1.6 IU/ml, the subject is determined to have a probability of 50.0% for developing HCMV active infection. In a preferred embodiment, the reference value is 3.2 IU/ml, and if the absolute quantity of the antibody against pp150 is below or equal to 3.2 IU/ml, the subject is determined to have a probability of 31.3% for developing HCMV active infection. In a preferred embodiment, the reference value is 6.4 IU/ml, and if the antibody absolute quantity of the antibody against pp150 is below or equal to 6.4 IU/ml, the subject is determined to have a probability of 19.0% for developing HCMV active infection.

In a preferred embodiment, the method according to the invention further comprises:

before the step (1), providing a body fluid sample from the subject; and/or after the step (2), administering a vaccine or antibody against HCMV to the subject that is determined to be at risk of developing HCMV active infection, so as to reduce the risk of developing HCMV active infection in the subject.

In one aspect, the invention provides use of a reagent capable of determining the level of an antibody against a HCMV protein in the manufacture of a kit for assessing whether a subject is at risk of developing human cytomegalovirus (HCMV) active infection by determining the level of an antibody against a HCMV protein in a body fluid sample from the subject.

In a preferred embodiment, the reagent is capable of determining the level of an antibody against a HCMV protein by immunologic assay. In a further preferred embodiment, the immunologic assay is selected from ELISA assay, Western Blot, surface plasmon resonance, and Elispot assay.

In a preferred embodiment, the reagent is selected from: HCMV protein or an antigenic fragment thereof, a fusion protein comprising the HCMV protein or an antigenic fragment thereof, and any combination thereof.

In a preferred embodiment, the HCMV protein is selected from pp150 and/or pp28.

In a preferred embodiment, the HCMV protein is pp150, and the reagent is pp150 and/or an antigenic fragment thereof (for example, a fragment comprising aa 861-1048 of pp150); or, the HCMV protein is pp28, and the reagent is pp28 and/or an antigenic fragment thereof; or, the HCMV protein is pp150 and pp28, and the reagent comprises: pp150 and/or an antigenic fragment thereof (for example, a fragment comprising aa 861-1048 of pp150) as a first component, and pp28 and/or an antigenic fragment thereof as a second component.

In a preferred embodiment, pp150 has an amino acid sequence set forth in SEQ ID NO: 1; and/or, the antigenic fragment of pp150 has an amino acid sequence set forth in SEQ ID NO: 2; and/or, pp28 has an amino acid sequence set forth in SEQ ID NO: 3;

In a preferred embodiment, the subject is a mammal, such as human.

In a preferred embodiment, the body fluid sample is selected from blood, serum, plasma, urine and saliva.

In a preferred embodiment, the active infection is a primary infection by HCMV in a subject that has not been infected by HCMV, or, a re-infection by HCMV or activation of latent HCMV in a subject that has been infected by HCMV.

In a preferred embodiment, the kit further comprises:

(i) a device for collecting or storing the body fluid sample from the subject;

(ii) additional reagents necessary for the assay (for example, a buffer, a diluent, a blocking solution, a labelled anti-antibody, and/or a standard sample); and/or, (iii) a vaccine or antibody against HCMV.

In a preferred embodiment, the kit assesses whether a subject is at risk of developing human cytomegalovirus (HCMV) active infection by a method comprising the following steps of:

(1) using the reagent to determine the level of an antibody against a HCMV protein in a body fluid sample from the subject; and, (2) comparing the level with a predetermined reference value;

wherein, if the level is below the reference value, the subject is determined to be at risk of developing HCMV active infection.

In a further preferred embodiment, in the method, the level refers to an antibody titer (for example, an antibody titer determined by ELISA), and the reference value refers to a predetermined antibody titer; or, the level refers to an antibody absolute quantity (for example, an absolute quantity expressed by IU/ml), and the reference value refers to a predetermined antibody absolute quantity (for example, an absolute quantity expressed by IU/ml).

In a further preferred embodiment, in the method, in the step (1), the antibody titer of the antibody against pp150 and/or pp28 in the body fluid sample is determined by ELISA. In a preferred embodiment, pp150 and/or an antigenic fragment thereof (for example, a fragment comprising aa 861-1048 of pp150) is used to determine the antibody titer of the antibody against pp150 in the body fluid sample by ELISA; and/or, pp28 and/or an antigenic fragment thereof is used to determine the antibody titer of the antibody against pp28 in the body fluid sample by ELISA. In a preferred embodiment, the reference value is an antibody titer in a range of 40-320. In a preferred embodiment, the reference value is an antibody titer in a range of 40-160. For example, the reference value is an antibody titer of 40, 80 or 160. In a preferred embodiment, the reference value is an antibody titer of 80.

In a preferred embodiment, the reference value is 40, and if the antibody titer of the antibody against pp150 is below or equal to 40, the subject is determined to have a relative risk of 11.2 for developing HCMV active infection, and 95% CI is 8.7-14.6. In a preferred embodiment, the reference value is 40, and if the antibody titer of the antibody against pp150 is below or equal to 40, the subject is determined to have a probability of 55.37% for developing HCMV active infection. In some preferred embodiments, the reference value is set as an antibody titer of 40, and the method for predicting HCMV active infection has a sensitivity of 57.3%, a specificity of 94.7%, and a Youden index of 0.52.

In another preferred embodiment, the reference value is 80, and if the antibody titer of the antibody against pp150 is below or equal to 80, the subject is determined to have a relative risk of 10.6 for developing HCMV active infection, and 95% CI is 7.7-14.6. In another preferred embodiment, the reference value is 80, and if the antibody titer of the antibody against pp150 is below or equal to 80, the subject is determined to have a probability of 36.98% for developing HCMV active infection. In some preferred embodiments, the reference value is set as an antibody titer of 80, and the method for predicting HCMV active infection has a sensitivity of 73.1%, a specificity of 85.7%, and a Youden index of 0.59.

In another preferred embodiment, the reference value is 160, and if the antibody titer of the antibody against pp150 is below or equal to 160, the subject is determined to have a relative risk of 14.8 for developing HCMV active infection, and 95% CI is 9.0-24.6. In another preferred embodiment, the reference value is 160, and if the antibody titer of the antibody against pp150 is below or equal to 160, the subject is determined to have a probability of 23.66% for developing HCMV active infection. In some preferred embodiments, the reference value is set as an antibody titer of 160, and the method for predicting HCMV active infection has a sensitivity of 90.6%, a specificity of 66.4%, and a Youden index of 0.57.

In another preferred embodiment, the reference value is 320, and if the antibody titer of the antibody against pp150 is below or equal to 320, the subject is determined to have a relative risk of 23.7 for developing HCMV active infection, and 95% CI is 8.8-63.4. In another preferred embodiment, the reference value is 320, and if the antibody titer of the antibody against pp150 is below or equal to 320, the subject is determined to have a probability of 15.77% for developing HCMV active infection. In some preferred embodiments, the reference value is set as an antibody titer of 320, and the method for predicting HCMV active infection has a sensitivity of 97.7%, a specificity of 40.1%, and a Youden index of 0.37.

In another preferred embodiment, in the method, in the step (1), the absolute quantity of the antibody against pp150 and/or pp28 in the body fluid sample (for example, an absolute quantity expressed by IU/ml) is determined. In a preferred embodiment, the absolute quantity of the antibody against pp150 and/or pp28 in the body fluid sample is determined by comparing the reactivity of the antibody against pp150 and/or pp28 in the body fluid sample with the antibody reactivity of a standard sample with a known antibody content. In a preferred embodiment, the reference value is an antibody absolute quantity in a range of 0.8-6.4 IU/ml. In a preferred embodiment, the reference value is an antibody absolute quantity in a range of 0.8-3.2 IU/ml. For example, the reference value is an antibody absolute quantity of 0.8, 1.6, or 3.2 IU/ml. In a preferred embodiment, the reference value is an antibody absolute quantity of 3.2 IU/ml.

In a preferred embodiment, the reference value is 0.8 IU/ml, and if the absolute quantity of the antibody against pp150 is below or equal to 0.8 IU/ml, the subject is determined to have a relative risk of 11.6 for developing HCMV active infection, and 95% CI is 7.8-17.2. In a preferred embodiment, the reference value is 0.8 IU/ml, and if the absolute quantity of the antibody against pp150 is below or equal to 0.8 IU/ml, the subject is determined to have a probability of 60.0% for developing HCMV active infection. In some preferred embodiments, the reference value is 0.8 IU/ml, and the method for predicting HCMV active infection has a sensitivity of 46.15%, a specificity of 96.97%, and a Youden index of 0.43.

In another preferred embodiment, the reference value is 1.6 IU/ml, and if the absolute quantity of the antibody against pp150 is below or equal to 1.6 IU/ml, the subject is determined to have a relative risk of 15.2 for developing HCMV active infection, and 95% CI is 9.5-24.3. In a preferred embodiment, the reference value is 1.6 IU/ml, and if the absolute quantity of the antibody against pp150 is below or equal to 1.6 IU/ml, the subject is determined to have a probability of 50.0% for developing HCMV active infection. In some preferred embodiments, the reference value is 1.6 IU/ml, and the method for predicting HCMV active infection has a sensitivity of 67.69%, a specificity of 93.34%, and a Youden index of 0.61.

In another preferred embodiment, the reference value is 3.2 IU/ml, and if the absolute quantity of the antibody against pp150 is below or equal to 3.2 IU/ml, the subject is determined to have a relative risk of 19.0 for developing HCMV active infection, and 95% CI is 9.6-37.7. In a preferred embodiment, the reference value is 3.2 IU/ml, and if the absolute quantity of the antibody against pp150 is below or equal to 3.2 IU/ml, the subject is determined to have a probability of 31.3% for developing HCMV active infection. In some preferred embodiments, the reference value is 3.2 IU/ml, and the method for predicting HCMV active infection has a sensitivity of 86.15%, a specificity of 81.39%, and a Youden index of 0.68.

In another preferred embodiment, the reference value is 6.4 IU/ml, and if the antibody absolute quantity of the antibody against pp150 is below or equal to 6.4 IU/ml, the subject is determined to have a relative risk of 25.2 for developing HCMV active infection, and 95% CI is 8.0-79.6. In a preferred embodiment, the reference value is 6.4 IU/ml, and if the antibody absolute quantity of the antibody against pp150 is below or equal to 6.4 IU/ml, the subject is determined to have a probability of for 19.0% developing HCMV active infection. In some preferred embodiments, the reference value is 6.4 IU/ml, and the method for predicting HCMV active infection has a sensitivity of 95.38%, a specificity of 59.91%, and a Youden index of 0.55.

In one aspect, the invention provides a kit for assessing whether a subject is at risk of developing human cytomegalovirus (HCMV) active infection, comprising a reagent capable of determining the level of an antibody against a HCMV protein, and optionally, instructions of using the reagent to determine the level of an antibody against a HCMV protein in a body fluid sample from the subject so as to assess whether the subject is at risk of developing human cytomegalovirus (HCMV) active infection.

In a preferred embodiment, the reagent is capable of determining the level of an antibody against a HCMV protein by immunologic assay. In a further preferred embodiment, the immunologic assay is selected from ELISA assay, Western Blot, surface plasmon resonance, and Elispot assay.

In a preferred embodiment, the reagent is selected from: HCMV protein or an antigenic fragment thereof, a fusion protein comprising the HCMV protein or an antigenic fragment thereof, and any combination thereof. In a preferred embodiment, the HCMV protein is selected from pp150 and/or pp28.

In a preferred embodiment, the HCMV protein is pp150, and the reagent is pp150 and/or an antigenic fragment thereof (for example, a fragment comprising aa 861-1048 of pp150); or, the HCMV protein is pp28, and the reagent is pp28 and/or an antigenic fragment thereof; or, the HCMV protein is pp150 and pp28, and the reagent comprises: pp150 and/or an antigenic fragment thereof (for example, a fragment comprising aa 861-1048 of pp150) as a first component, and pp28 and/or an antigenic fragment thereof as a second component.

In a preferred embodiment, pp150 has an amino acid sequence set forth in SEQ ID NO: 1; and/or, the antigenic fragment of pp150 has an amino acid sequence set forth in SEQ ID NO: 2; and/or, pp28 has an amino acid sequence set forth in SEQ ID NO: 3;

In a preferred embodiment, the subject is a mammal, such as human. In a preferred embodiment, the body fluid sample is selected from blood, serum, plasma, urine and saliva.

In a preferred embodiment, the active infection is a primary infection by HCMV in a subject that has not been infected by HCMV, or, a re-infection by HCMV or activation of latent HCMV in a subject that has been infected by HCMV.

In a preferred embodiment, the kit further comprises:
(i) a device for collecting or storing the body fluid sample from the subject;
(ii) additional reagents necessary for the assay (for example, a buffer, a diluent, a blocking solution, a labelled anti-antibody, and/or a standard sample); and/or,
(iii) a vaccine or antibody against HCMV.

In a preferred embodiment, the kit assesses whether a subject is at risk of developing human cytomegalovirus (HCMV) active infection by a method comprising the following steps of:
(1) using the reagent to determine the level of an antibody against a HCMV protein in a body fluid sample from the subject; and,
(2) comparing the level with a predetermined reference value;
wherein, if the level is below the reference value, the subject is determined to be at risk of developing HCMV active infection.

In a further preferred embodiment, in the method, the level refers to an antibody titer (for example, an antibody titer determined by ELISA), and the reference value refers to a predetermined antibody titer; or, the level refers to an antibody absolute quantity (for example, an absolute quantity expressed by IU/ml), and the reference value refers to a predetermined antibody absolute quantity (for example, an absolute quantity expressed by IU/ml).

In a further preferred embodiment, in the method, in the step (1), the antibody titer of the antibody against pp150 and/or pp28 in the body fluid sample is determined by ELISA; In a preferred embodiment, pp150 and/or an antigenic fragment thereof (for example, a fragment comprising aa 861-1048 of pp150) is used to determine the antibody titer of the antibody against pp150 in the body fluid sample by ELISA; and/or, pp28 and/or an antigenic fragment thereof is used to determine the antibody titer of the antibody against pp28 in the body fluid sample by ELISA. In a preferred embodiment, the reference value is an antibody titer in a range of 40-320. In a preferred embodiment, the reference value is an antibody titer in a range of 40-160. For example, the reference value is an antibody titer of 40, 80 or 160. In a preferred embodiment, the reference value is an antibody titer of 80.

In a preferred embodiment, the reference value is 40, and if the antibody titer of the antibody against pp150 is below or equal to 40, the subject is determined to have a relative risk of 11.2 for developing HCMV active infection, and 95% CI is 8.7-14.6. In a preferred embodiment, the reference value is 40, and if the antibody titer of the antibody against pp150 is below or equal to 40, the subject is determined to have a probability of 55.37% for developing HCMV active infection. In some preferred embodiments, the reference value is set as an antibody titer of 40, and the method for predicting HCMV active infection has a sensitivity of 57.3%, a specificity of 94.7%, and a Youden index of 0.52.

In another preferred embodiment, the reference value is 80, and if the antibody titer of the antibody against pp150 is below or equal to 80, the subject is determined to have a relative risk of 10.6 for developing HCMV active infection, and 95% CI is 7.7-14.6. In another preferred embodiment, the reference value is 80, and if the antibody titer of the antibody against pp150 is below or equal to 80, the subject is determined to have a probability of 36.98% for developing HCMV active infection. In some preferred embodiments, the reference value is set as an antibody titer of 80, and the method for predicting HCMV active infection has a sensitivity of 73.1%, a specificity of 85.7%, and a Youden index of 0.59.

In another preferred embodiment, the reference value is 160, and if the antibody titer of the antibody against pp150 is below or equal to 160, the subject is determined to have a relative risk of 14.8 for developing HCMV active infection, and 95% CI is 9.0-24.6. In another preferred embodiment, the reference value is 160, and if the antibody titer of the antibody against pp150 is below or equal to 160, the subject is determined to have a probability of 23.66% for developing HCMV active infection. In some preferred embodiments, the reference value is set as an antibody titer of 160, and the method for predicting HCMV active infection has a sensitivity of 90.6%, a specificity of 66.4%, and a Youden index of 0.57.

In another preferred embodiment, the reference value is 320, and if the antibody titer of the antibody against pp150 is below or equal to 320, the subject is determined to have a relative risk of 23.7 for developing HCMV active infection, and 95% CI is 8.8-63.4. In another preferred embodiment, the reference value is 320, and if the antibody titer of the antibody against pp150 is below or equal to 320, the subject is determined to have a probability of 15.77% for developing HCMV active infection. In some preferred embodiments, the reference value is set as an antibody titer of 320, and the method for predicting HCMV active infection has a sensitivity of 97.7%, a specificity of 40.1%, and a Youden index of 0.37.

In another preferred embodiment, in the method, in the step (1), the absolute quantity of the antibody against pp150 and/or pp28 in the body fluid sample (for example, an absolute quantity expressed by IU/ml). In a preferred embodiment, the absolute quantity of the antibody against pp150 and/or pp28 in the body fluid sample is determined by comparing the reactivity of the antibody against pp150 and/or pp28 in the body fluid sample with the antibody reactivity of a standard sample with a known antibody content. In a preferred embodiment, the reference value is an antibody absolute quantity in a range of 0.8-6.4 IU/ml. In a preferred embodiment, the reference value is an antibody absolute quantity in a range of 0.8-3.2 IU/ml. For example, the reference value is an antibody absolute quantity of 0.8, 1.6, or 3.2 IU/ml. In a preferred embodiment, the reference value is an antibody absolute quantity of 3.2 IU/ml.

In a preferred embodiment, the reference value is 0.8 IU/ml, and if the absolute quantity of the antibody against pp150 is below or equal to 0.8 IU/ml, the subject is determined to have a relative risk of 11.6 for developing HCMV active infection, and 95% CI is 7.8-17.2. In a preferred embodiment, the reference value is 0.8 IU/ml, and if the absolute quantity of the antibody against pp150 is below or equal to 0.8 IU/ml, the subject is determined to have a probability of 60.0% for developing HCMV active infection. In some preferred embodiments, the reference value is 0.8

IU/ml, and the method for predicting HCMV active infection has a sensitivity of 46.15%, a specificity of 96.97%, and a Youden index of 0.43.

In another preferred embodiment, the reference value is 1.6 IU/ml, and if the absolute quantity of the antibody against pp150 is below or equal to 1.6 IU/ml, the subject is determined to have a relative risk of 15.2 for developing HCMV active infection, and 95% CI is 9.5-24.3. In a preferred embodiment, the reference value is 1.6 IU/ml, and if the absolute quantity of the antibody against pp150 is below or equal to 1.6 IU/ml, the subject is determined to have a probability of 50.0% for developing HCMV active infection. In some preferred embodiments, the reference value is 1.6 IU/ml, and the method for predicting HCMV active infection has a sensitivity of 67.69%, a specificity of 93.34%, and a Youden index of 0.61.

In another preferred embodiment, the reference value is 3.2 IU/ml, and if the absolute quantity of the antibody against pp150 is below or equal to 3.2 IU/ml, the subject is determined to have a relative risk of 19.0 for developing HCMV active infection, and 95% CI is 9.6-37.7. In a preferred embodiment, the reference value is 3.2 IU/ml, and if the absolute quantity of the antibody against pp150 is below or equal to 3.2 IU/ml, the subject is determined to have a probability of 31.3% for developing HCMV active infection. In some preferred embodiments, the reference value is 3.2 IU/ml, and the method for predicting HCMV active infection has a sensitivity of 86.15%, a specificity of 81.39%, and a Youden index of 0.68.

In another preferred embodiment, the reference value is 6.4 IU/ml, and if the antibody absolute quantity of the antibody against pp150 is below or equal to 6.4 IU/ml, the subject is determined to have a relative risk of 25.2 for developing HCMV active infection, and 95% CI is 8.0-79.6. In a preferred embodiment, the reference value is 6.4 IU/ml, and if the antibody absolute quantity of the antibody against pp150 is below or equal to 6.4 IU/ml, the subject is determined to have a probability of 19.0% for developing HCMV active infection. In some preferred embodiments, the reference value is 6.4 IU/ml, and the method for predicting HCMV active infection has a sensitivity of 95.38%, a specificity of 59.91%, and a Youden index of 0.55.

The method of the invention can determine the level of an antibody against a HCMV protein in a body fluid sample from a subject, and therefore reliably and effectively assessing whether the subject is at risk of developing human cytomegalovirus (HCMV) active infection. Based on this, if after the administration of a certain candidate drug, a subject has the level of an antibody against a HCMV protein increased (compared to the level before the administration of the candidate drug) in a body fluid sample therefrom, it indicates that after the administration of the candidate drug, the subject has the risk of developing human cytomegalovirus (HCMV) active infection reduced. Therefore, it can be reasonably determined that the candidate drug used can improve the ability of a subject to resist human cytomegalovirus (HCMV) active infection, and reduce the risk of developing human cytomegalovirus (HCMV) active infection in a subject.

Therefore, in another aspect, the invention provides a method for screening a candidate drug capable of improving the ability of a subject to resist human cytomegalovirus (HCMV) active infection or reducing the risk of developing human cytomegalovirus (HCMV) active infection in a subject, comprising the following steps of:

(1) before administering a candidate drug to a test animal, determining a first level of an antibody against a HCMV protein in a body fluid sample from the test animal;

(2) administering the candidate drug to the test animal;

(3) after administering the candidate drug to the test animal, determining a second level of the antibody against a HCMV protein in the body fluid sample from the test animal;

(4) comparing the first level with the second level, wherein, if the first level is below the second level, the candidate drug is determined to be capable of improving the ability of a subject to resist human cytomegalovirus (HCMV) active infection or reducing the risk of developing human cytomegalovirus (HCMV) active infection.

In a preferred embodiment, the test animal is a non-human mammal, such as a model animal (for example, mouse, rat, rabbit, primate). In a preferred embodiment, the body fluid sample is selected from blood, serum, plasma, urine and saliva.

In a preferred embodiment, the subject is a mammal, such as human.

In a preferred embodiment, the active infection is a primary infection by HCMV in a subject that has not been infected by HCMV, or, a re-infection by HCMV or activation of latent HCMV in a subject that has been infected by HCMV.

In a preferred embodiment, the HCMV protein is selected from pp150 and/or pp28.

In a preferred embodiment, the level of an antibody against a HCMV protein in the body fluid sample is determined by immunologic assay. In a further preferred embodiment, the immunologic assay is selected from ELISA assay, Western Blot, surface plasmon resonance, and Elispot assay.

In a preferred embodiment, the first level and the second level refer to an antibody titer (for example, an antibody titer determined by ELISA); or, the first level and the second level refer to an antibody absolute quantity (for example, an absolute quantity expressed by IU/ml).

In a preferred embodiment, in the steps (1) and (3), the first level and the second level of an antibody against pp150 and/or pp28 in the body fluid sample are determined by ELISA. In a preferred embodiment, pp150 and/or an antigenic fragment thereof (for example, a fragment comprising aa 861-1048 of pp150) is used to determine the first level and the second level of an antibody against pp150 in the body fluid sample by ELISA; and/or, pp28 and/or an antigenic fragment thereof is used to determine the first level and the second level of an antibody against pp28 in the body fluid sample by ELISA.

In a preferred embodiment, pp150 has an amino acid sequence set forth in SEQ ID NO: 1; and/or, the antigenic fragment of pp150 has an amino acid sequence set forth in SEQ ID NO: 2; and/or, pp28 has an amino acid sequence set forth in SEQ ID NO: 3.

In a preferred embodiment, the first level and the second level of an antibody against pp150 and/or pp28 in the body fluid sample are determined by comparing the reactivity of the antibody against pp150 and/or pp28 in the body fluid sample with the antibody reactivity of a standard sample with a known antibody content.

In another aspect, the invention provides use of a reagent capable of determining the level of an antibody against a HCMV protein in the manufacture of a kit for screening a candidate drug capable of improving the ability of a subject to resist human cytomegalovirus (HCMV) active infection or reducing the risk of developing human cytomegalovirus (HCMV) active infection in a subject.

In a preferred embodiment, the reagent is capable of determining the level of an antibody against a HCMV protein by immunologic assay. In a further preferred embodiment, the immunologic assay is selected from ELISA assay, Western Blot, surface plasmon resonance, and Elispot assay.

In a preferred embodiment, the reagent is selected from: HCMV protein or an antigenic fragment thereof, a fusion protein comprising the HCMV protein or an antigenic fragment thereof, and any combination thereof. In a preferred embodiment, the HCMV protein is selected from pp150 and/or pp28.

In a preferred embodiment, the HCMV protein is pp150, and the reagent is pp150 and/or an antigenic fragment thereof (for example, a fragment comprising aa 861-1048 of pp150); or, the HCMV protein is pp28, and the reagent is pp28 and/or an antigenic fragment thereof; or, the HCMV protein is pp150 and pp28, and the reagent comprises: pp150 and/or an antigenic fragment thereof (for example, a fragment comprising aa 861-1048 of pp150) as a first component, and pp28 and/or an antigenic fragment thereof as a second component.

In a preferred embodiment, pp150 has an amino acid sequence set forth in SEQ ID NO: 1; and/or, the antigenic fragment of pp150 has an amino acid sequence set forth in SEQ ID NO: 2; and/or, pp28 has an amino acid sequence set forth in SEQ ID NO: 3.

In a preferred embodiment, the subject is a mammal, such as human.

In a preferred embodiment, the active infection is a primary infection by HCMV in a subject that has not been infected by HCMV, or, a re-infection by HCMV or activation of latent HCMV in a subject that has been infected by HCMV.

In a preferred embodiment, the kit screens a candidate drug capable of improving the ability of a subject to resist human cytomegalovirus (HCMV) active infection or reducing the risk of developing human cytomegalovirus (HCMV) active infection in a subject by a method comprising the following steps of:

(1) before administering a candidate drug to a test animal, determining a first level of an antibody against a HCMV protein in a body fluid sample from the test animal;

(2) administering the candidate drug to the test animal;

(3) after administering the candidate drug to the test animal, determining a second level of the antibody against a HCMV protein in the body fluid sample from the test animal; and (4) comparing the first level with the second level, wherein, if the first level is below the second level, the candidate drug is determined to be capable of improving the ability of a subject to resist human cytomegalovirus (HCMV) active infection or reducing the risk of developing human cytomegalovirus (HCMV) active infection.

In a preferred embodiment, the test animal is a non-human mammal, such as a model animal (for example, mouse, rat, rabbit, primate).

In a preferred embodiment, the body fluid sample is selected from blood, serum, plasma, urine and saliva.

In a preferred embodiment, the kit further comprises:

(i) a device for collecting or storing the body fluid sample from the test animal; and/or (ii) additional reagents necessary for determining the first level and the second level (for example, a buffer, a diluent, a blocking solution, a labelled anti-antibody, and/or a standard sample).

In a preferred embodiment, the first level and the second level refer to an antibody titer (for example, an antibody titer determined by ELISA); or, the first level and the second level refer to an antibody absolute quantity (for example, an absolute quantity expressed by IU/ml).

In a preferred embodiment, in the method, in the steps (1) and (3), the first level and the second level of the antibody against pp150 and/or pp28 in the body fluid sample are determined by ELISA. In a preferred embodiment, pp150 and/or an antigenic fragment thereof (for example, a fragment comprising aa 861-1048 of pp150) is used to determine the first level and the second level of an antibody against pp150 in the body fluid sample by ELISA; and/or, pp28 and/or an antigenic fragment thereof is used to determine the first level and the second level of an antibody against pp28 in the body fluid sample by ELISA.

In a preferred embodiment, pp150 has an amino acid sequence set forth in SEQ ID NO: 1; and/or, the antigenic fragment of pp150 has an amino acid sequence set forth in SEQ ID NO: 2; and/or, pp28 has an amino acid sequence set forth in SEQ ID NO: 3.

In a preferred embodiment, the first level and the second level of the antibody against pp150 and/or pp28 in the body fluid sample are determined by comparing the reactivity of the antibody against pp150 and/or pp28 in the body fluid sample with the antibody reactivity of a standard sample with a known antibody content.

In another aspect, the invention provides a kit for screening a candidate drug capable of improving the ability of a subject to resist human cytomegalovirus (HCMV) active infection or reducing the risk of developing human cytomegalovirus (HCMV) active infection in a subject, comprising a reagent capable of determining the level of an antibody against a HCMV protein, and optionally, instructions of using the reagent to screen a candidate drug capable of improving the ability of a subject to resist human cytomegalovirus (HCMV) active infection or reducing the risk of developing human cytomegalovirus (HCMV) active infection in a subject.

In a preferred embodiment, the reagent is capable of determining the level of an antibody against a HCMV protein by immunologic assay. In a further preferred embodiment, the immunologic assay is selected from ELISA assay, Western Blot, surface plasmon resonance, and Elispot assay;

In a preferred embodiment, the reagent is selected from: HCMV protein or an antigenic fragment thereof, a fusion protein comprising the HCMV protein or an antigenic fragment thereof, and any combination thereof. In a preferred embodiment, the HCMV protein is selected from pp150 and/or pp28.

In a preferred embodiment, the HCMV protein is pp150, and the reagent is pp150 and/or an antigenic fragment thereof (for example, a fragment comprising aa 861-1048 of pp150); or, the HCMV protein is pp28, and the reagent is pp28 and/or an antigenic fragment thereof; or, the HCMV protein is pp150 and pp28, and the reagent comprises: pp150 and/or an antigenic fragment thereof (for example, a fragment comprising aa 861-1048 of pp150) as a first component, and pp28 and/or an antigenic fragment thereof as a second component.

In a preferred embodiment, pp150 has an amino acid sequence set forth in SEQ ID NO: 1; and/or, the antigenic fragment of pp150 has an amino acid sequence set forth in SEQ ID NO: 2; and/or, pp28 has an amino acid sequence set forth in SEQ ID NO: 3.

In a preferred embodiment, the subject is a mammal, such as human.

In a preferred embodiment, the active infection is a primary infection by HCMV in a subject that has not been infected by HCMV, or, a re-infection by HCMV or activation of latent HCMV in a subject that has been infected by HCMV.

In a preferred embodiment, the kit screens a candidate drug capable of improving the ability of a subject to resist human cytomegalovirus (HCMV) active infection or reducing the risk of developing human cytomegalovirus (HCMV) active infection in a subject by a method comprising the following steps of:

(1) before administering a candidate drug to a test animal, determining a first level of an antibody against a HCMV protein in a body fluid sample from the test animal;

(2) administering the candidate drug to the test animal;

(3) after administering the candidate drug to the test animal, determining a second level of the antibody against a HCMV protein in the body fluid sample from the test animal; and (4) comparing the first level with the second level;

wherein, if the first level is below the second level, the candidate drug is determined to be capable of improving the ability of a subject to resist human cytomegalovirus (HCMV) active infection or reducing the risk of developing human cytomegalovirus (HCMV) active infection.

In a preferred embodiment, the test animal is a non-human mammal, such as a model animal (for example, mouse, rat, rabbit, primate). In a preferred embodiment, the body fluid sample is selected from blood, serum, plasma, urine and saliva.

In a preferred embodiment, the kit further comprises:

(i) a device for collecting or storing the body fluid sample from the test animal; and/or (ii) additional reagents necessary for determining the first level and the second level (for example, a buffer, a diluent, a blocking solution, a labelled anti-antibody, and/or a standard sample).

In a preferred embodiment, the first level and the second level refer to an antibody titer (for example, an antibody titer determined by ELISA); or, the first level and the second level refer to an antibody absolute quantity (for example, an absolute quantity expressed by IU/ml).

In a preferred embodiment, in the method, in the steps (1) and (3), the first level and the second level of the antibody against pp150 and/or pp28 in the body fluid sample are determined by ELISA. In a preferred embodiment, pp150 and/or an antigenic fragment thereof (for example, a fragment comprising aa 861-1048 of pp150) is used to determine the first level and the second level of an antibody against pp150 in the body fluid sample by ELISA; and/or, pp28 and/or an antigenic fragment thereof is used to determine the first level and the second level of an antibody against pp28 in the body fluid sample by ELISA.

In a preferred embodiment, pp150 has an amino acid sequence set forth in SEQ ID NO: 1; and/or, the antigenic fragment of pp150 has an amino acid sequence set forth in SEQ ID NO: 2; and/or, pp28 has an amino acid sequence set forth in SEQ ID NO: 3.

In a preferred embodiment, the first level and the second level of the antibody against pp150 and/or pp28 in the body fluid sample are determined by comparing the reactivity of the antibody against pp150 and/or pp28 in the body fluid sample with the antibody reactivity of a standard sample with a known antibody content.

Beneficial Effects of the Invention

As compared with the prior art, the technical solutions of the invention have the following beneficial effects.

(1) The invention demonstrates for the first time the significant correlation between the level of an antibody against a HCMV protein (for example, pp150/pp28) and the risk of developing human cytomegalovirus (HCMV) active infection. In particular, the invention demonstrates for the first time that when the antibody titer of an antibody against pp150 in a body fluid sample from a subject is below or equal to 40, the subject has a probability of 55.37% for developing HCMV active infection, the relative risk is 11.2, and 95% CI is 8.7-14.6; when the antibody titer of an antibody against pp150 in a body fluid sample from a subject is below or equal to 80, the subject has a probability of 36.98% for developing HCMV active infection, the relative risk is 10.6, and 95% CI is 7.7-14.6; when the antibody titer of an antibody against pp150 in a body fluid sample from a subject is below or equal to 160, the subject has a probability of 23.66% for developing HCMV active infection, the relative risk is 14.8, and 95% CI is 9.0-24.6; when the antibody titer of an antibody against pp150 in a body fluid sample from a subject is below or equal to 320, the subject has a probability of 15.77% for developing HCMV active infection, the relative risk is 23.7, and 95% CI is 8.8-63.4. In addition, the invention also demonstrates for the first time that when the content of an antibody against pp150 in a body fluid sample from a subject is below 0.8 IU/ml, the subject has a probability of 60.0% for developing HCMV active infection, the relative risk is 11.6, and 95% CI is 7.8-17.2; when the content of an antibody against pp150 in a body fluid sample from a subject is below 1.6 IU/ml, the subject has a probability of 50.0% for developing HCMV active infection, the relative risk is 15.2, and 95% CI is 9.5-24.3; when the content of an antibody against pp150 in a body fluid sample from a subject is below 3.2 IU/ml, the subject has a probability of 31.3% for developing HCMV active infection, the relative risk is 19.0, and 95% CI is 9.6-37.7; when the content of an antibody against pp150 in a body fluid sample from a subject is below 6.4 IU/ml, the subject has a probability of 19.0% for developing HCMV active infection, the relative risk is 25.2, and 95% CI is 8.0-79.6. These solve the technical problem urgent to be solved in the art, i.e., to provide a highly sensitive and specific method capable of assessing the risk of developing human cytomegalovirus (HCMV) active infection in a subject accurately, reliably and effectively.

(2) The level of an antibody against a HCMV protein (for example, pp150/pp28) can be used as an index for predicting the risk of developing human cytomegalovirus (HCMV) active infection (for example, the risk of re-developing HCMV infection in a seropositive population); and, the methods according to the invention can be used to screen individuals (i.e., high-risk individuals) susceptible to human cytomegalovirus (HCMV) active infection from a natural population or a population in a high risk HCMV active infection area. Therefore, the methods according to the invention can provide support for employing intervention measures, and can direct clinical medication to prevent complications in patients. For example, the methods according to the invention may be applied to pregnant women to screen high-risk individuals, and can reduce the probability of neonatal congenital CMV infection; or, the methods according to the invention can be applied to immunocompromised patients such as organ transplant patients, to screen high-risk individuals, and reduce the probability of complications in patients by employing intervention measures and clinical medication in the individuals.

(3) The methods according to the invention can be used to screen a candidate drug capable of improving the ability of a subject to resist human cytomegalovirus (HCMV) active infection or reducing the risk of developing human cytomegalovirus (HCMV) active infection in a subject. Therefore, the methods according to the invention provides new concept and solution for developing new drugs for preventing and/or treating HCMV infection.

The embodiments of the invention are described in detail by reference to the drawings and examples. However, a person skilled in the art would understand that the following drawings and examples are intended for illustrating the invention only, rather than defining the scope of the invention. According to the detailed description of the following drawings and preferred embodiments, various purposes and advantages of the invention are apparent for a person skilled in the art.

DESCRIPTION OF THE DRAWINGS

FIG. 1A shows the correlation analysis of the detection results of 288 serum samples by the ELISA assay using pp150 and pp150-2 as coating antigens (abscissa) and the ELISA assay using purified virus as coating antigen (ordinate). The results show that the results determined by the two ELISA assays are highly identical, the coincidence rate of them is 99.3%, and the correlation of response intensity is significant (correlation coefficient r=0.85). FIG. 1B shows the comparison of the detection results of 36 serum samples by the ELISA assay using pp150 and pp150-2 as coating antigens and the ELISA assay using a commercially available CMV-IgG reagent (Diasorin-IgG) as coating antigen. The results show that the reactivity of the pp150 & pp150-2-based ELISA assay according to the invention is significantly stronger than the reactivity of Diasorin-based ELISA assay, and the reactivity of the latter to positive serums is substantively at a relatively low level. The results in FIGS. 1A and 1B show that the ELISA assay platform established in Example 2 can be used to determine the level of an antibody against a CMV protein (an antibody against pp150) in a serum sample accurately, reliably and effectively.

FIG. 6B shows the analysis of sensitivity and specificity of the pp150 assay platform for assessing the occurrence of a virus event (HCMV active infection), when the occurrence of a virus event (HCMV active infection) is defined by the circumstance where the detection results of the other assay platforms are triple positive or more.

FIG. 6C shows the analysis of sensitivity and specificity of the pp150 assay platform for assessing the occurrence of a virus event (HCMV active infection), when the occurrence of a virus event (HCMV active infection) is defined by the circumstance where the detection results of the other assay platforms are quadruple positive or more.

Figure 6A:
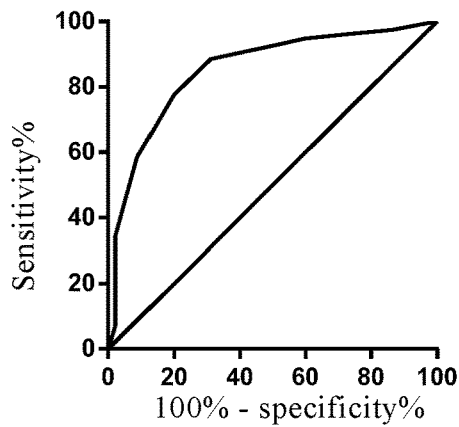
FIG. 6A-C shows the ROC curve analysis by the pp150 & pp150-2-based ELISA assay platform (called pp150 assay platform for short) under different criteria for a virus event in Example 6, wherein abscissa represents (100%−the detection specificity % of the assay platform), and the ordinate represents the detection sensitivity % of the assay platform; and, FIG. 6A shows the analysis of sensitivity and specificity of the pp150 assay platform for assessing the occurrence of a virus event (HCMV active infection), when the occurrence of a virus event (HCMV active infection) is defined by the circumstance where the detection results of the other assay platforms are double positive or more.
Figure 6B:
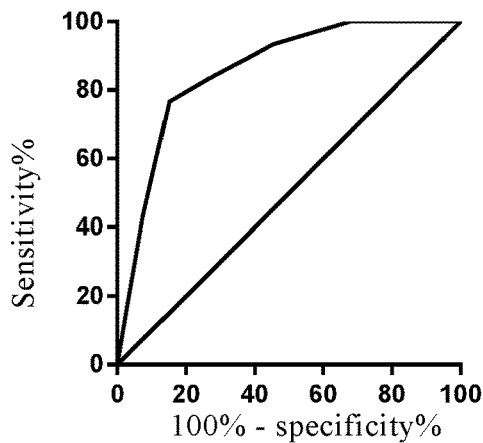
Figure 6C:
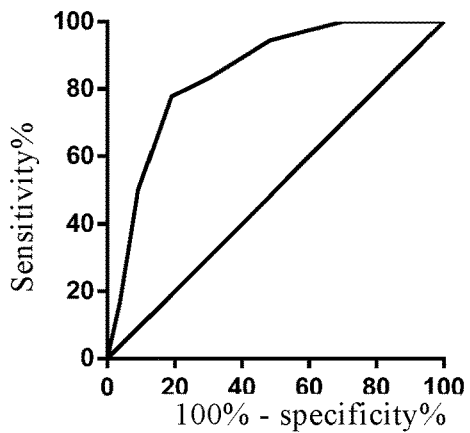

The results in FIG. 6A-C show that under all the three circumstances, the pp150 assay platform has an accuracy of above 80% for predicting the occurrence of a virus event (HCMV active infection), and therefore can be used to assess the risk of developing human cytomegalovirus (HCMV) active infection in a subject accurately, reliably and effectively.

Figure 7A:
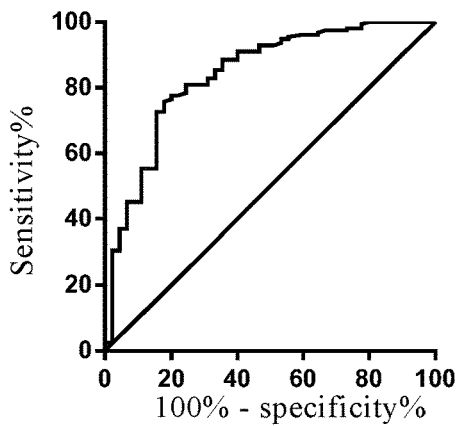
Figure 7B:
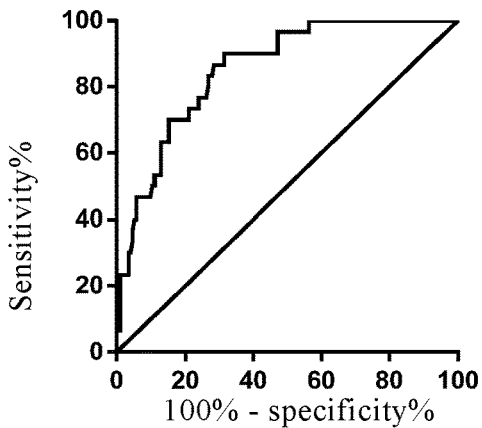
Figure 7C:
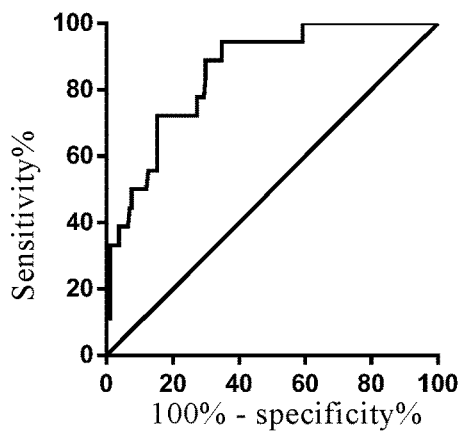

FIG. 7A-C shows the ROC curve analysis of the pp28-based ELISA assay platform (called pp28 assay platform for short) under different criteria for a virus event in Example 6, wherein abscissa represents (100%−the detection specificity % of the assay platform), and the ordinate represents the detection sensitivity % of the assay platform; and, FIG. 7A shows the analysis of sensitivity and specificity of the pp28 assay platform for assessing the occurrence of a virus event (HCMV active infection), when the occurrence of a virus event (HCMV active infection) is defined by the circumstance where the detection results of the other assay platforms are double positive or more.

FIG. 7B shows the analysis of sensitivity and specificity of the pp28 assay platform for assessing the occurrence of a virus event (HCMV active infection), when the occurrence of a virus event (HCMV active infection) is defined by the circumstance where the detection results of the other assay platforms are triple positive or more.

FIG. 7C shows the analysis of sensitivity and specificity of the pp28 assay platform for assessing the occurrence of a virus event (HCMV active infection), when the occurrence of a virus event (HCMV active infection) is defined by the circumstance where the detection results of the other assay platforms are quadruple positive or more.

The results in FIG. 7A-C show that under all the three circumstances, the pp28 assay platform has an accuracy of above 78% for predicting the occurrence of a virus event (HCMV active infection), and therefore can be used to assess the risk of developing human cytomegalovirus (HCMV) active infection in a subject accurately, reliably and effectively.

Figure 8:
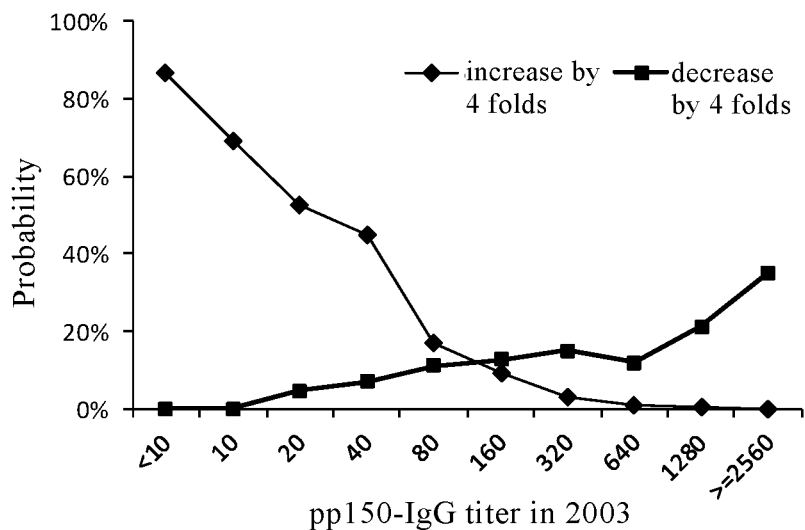

FIG. 8 shows the change in the antibody titer of an antibody against pp150 in a certain natural population as described in Example 7 over 12 months (one year), wherein, abscissa represents a baseline antibody level (antibody titer), ordinate represents the probability that the antibody level increases or decreases by 4 folds one year later. The results show that individuals with a higher baseline antibody level, have a lower probability that the level of an antibody against pp150 increases by 4 folds or more (i.e., developing HCMV active infection) one year later; while, individuals with a lower baseline antibody level of an individual, have a higher probability that the level of an antibody against pp150 increases by 4 folds or more (i.e., developing HCMV active infection) one year later. The risk of developing HCMV active infection in an individual is negatively correlated with the baseline antibody level.

Figure 9:
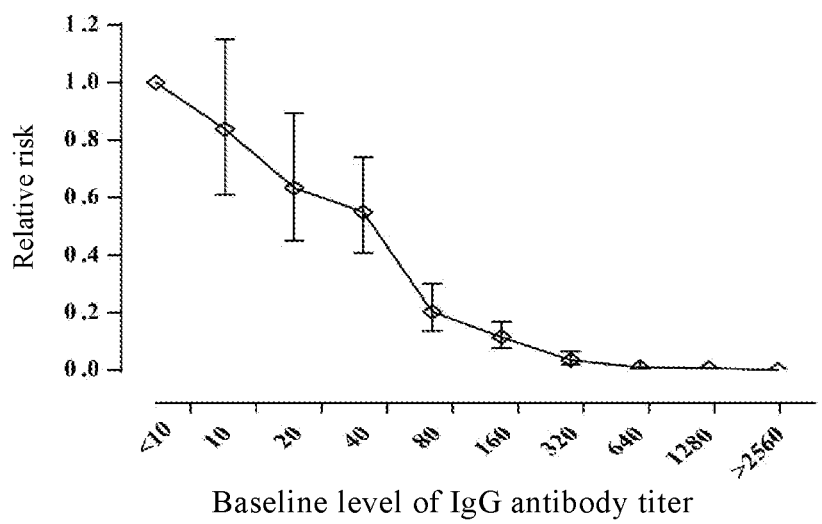

FIG. 9 shows the correlation between the baseline level of an antibody against pp150 and the risk of developing HCMV active infection in a certain natural population as described in Example 7, wherein, abscissa represents the baseline level of an antibody against pp150 (antibody titer), and ordinate represents the risk of developing HCMV active infection (ratio). The results show that individuals with a lower baseline antibody level, have a higher risk of developing HCMV active infection (i.e., the level of an antibody against pp150 increases by 4 folds or more) later. The risk of HCMV active infection is negatively correlated with the baseline antibody level. When the baseline antibody level (antibody titer) is lower than 10, the risk of developing HCMV active infection is up to 82.6%; and when the baseline antibody level (antibody titer) is no more than 160, the risk of developing HCMV active infection is up to 23.66%.

Figure 10:
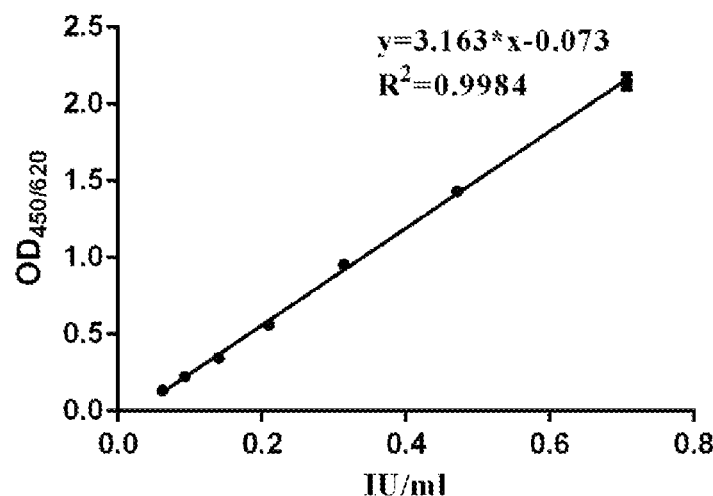

FIG. 10 shows an antibody content-antibody reactivity standard curve plotted using a standard sample (Paul-Ehrlich-Instltut, Referenz-CMV-IgG, Juli 1996, 110 IU/ml) comprising an antibody in a known amount, wherein, abscissa represents an antibody content (expressed as IU/ml); and ordinate represents antibody reactivity (expressed by the OD value obtained by ELISA). The results show that there is a significant linear relationship between the antibody content and antibody reactivity ($R^2$=0.9984), and the linearity range is more than an order of magnitude. Therefore, the antibody content-antibody reactivity standard curve plotted using a standard sample can be used to accurately quantify the antibody content (expressed as IU/ml) in a sample.

Figure 11:
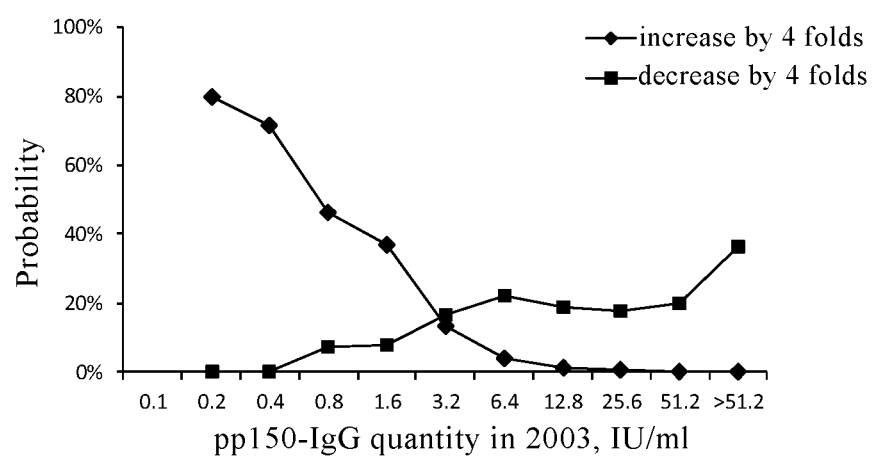

FIG. 11 shows the change in the content of an antibody against pp150 in a certain natural population as described in Example 8 over 12 months (one year), wherein, abscissa represents a baseline antibody level (antibody content), and ordinate represents the probability that the antibody level increases or decreases by 4 folds one year later. The results show that individuals with a lower baseline antibody level, have a higher probability that the level of an antibody against pp150 increases by 4 folds or more one year later (i.e., the antibody level obtained by the second detection is at least 4 folds higher than the antibody level obtained by the first detection, indicating that the individual has HCMV active infection within the interval of 12 months); while, individuals with a higher baseline antibody level, has a lower probability that the level of an antibody against pp150 increases by 4 folds or more one year later (i.e., developing HCMV active infection). The risk of developing HCMV active infection in an individual is negatively correlated with the baseline antibody level in serum.

Figure 12:
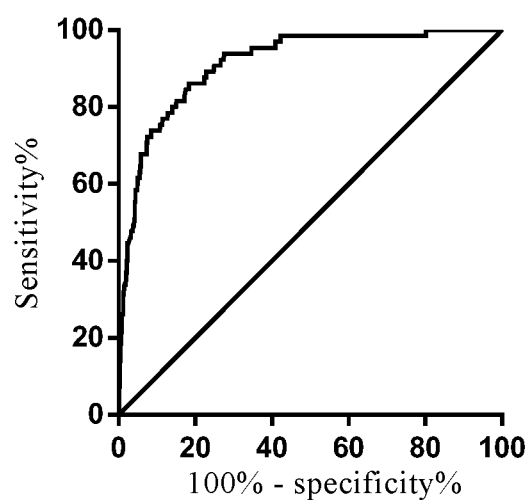

FIG. 12 shows ROC curve analytic results of the method described in Example 8, wherein, the method predicts HCMV active infection based on the content/absolute quantity of an antibody against pp150 in serum, wherein abscissa represents (100%−specificity % of the method), and ordinate represents the sensitivity % of the method. The results in FIG. 12 show that the method of the invention can be used to assess the risk of developing human cytomegalovirus (HCMV) active infection in a subject accurately, reliably and effectively.

SEQUENCE INFORMATION

The information of the sequences involved in the invention are provided in the following Table 1.

TABLE 1

Sequence information

| SEQ ID NO | Name | Sequence information 5'-3' |
|---|---|---|
| 1 | HCMV pp150 | MSLQFIGLQRRDVVALVNFLRHLTQKPDVDLEAHPKILKKCGEKRLHR RTVLFNELMLWLGYYRELRFHNPDLSSVLEEFEVRCVAVARRGYTYPF GDRGKARDHLAVLDRTEFDTDVRHDAEIVERALVSAVILAKMSVRETL VTAIGQTEPIAFVHLKDTEVQRIEENLEGVRRNMFCVKPLDLNLDRHAN TALVNAVNKLVYTGRLIMNVRRSWEELERKCLARIQERCKLLVKELRM CLSFDSNYCRNILKHAVENGDSADTLLELLIEDFDIYVDSFPQSAHTFLG ARSPSLEFDDDANLLSLGGGSAFSSVPKKHVPTQPLDGWSWIASPWKG |

TABLE 1-continued

Sequence information

| SEQ ID NO | Name | Sequence information 5'-3' |
|---|---|---|
| | | HKPFRFEAHGSLAPAAEAHAARSAAVGYYDEEEKRRERQKRVDDEVV QREKQQLKAWEERQQNLQQRQQQPPPPARKPSASRRLFGSSADEDDDD DDDEKNIFTPIKKPGTSGKGAASGGGVSSIFSGLLSSGSQKPTSGPLNIPQ QQQRHAAFSLVSPQVTKASPGRVRRDSAWDVRPLTETRGDLFSGDEDS DSSDGYPPNRQDPRFTDTLVDITDTETSAKPPVTTAYKFEQPTLTFGAGV NVPAGAGAAILTPTPVNPSTAPAPAPTPTFAGTQTPVNGNSPWAPTAPLP GDMNPANWPRERAWALKNPHLAYNPFRMPTTSTASQNTVSTTPRRPST PRAAVTQTASRDAADEVWALRDQTAESPVEDSEEEDDDSSDTGSVVSL GHTTPSSDYNNDVISPPSQTPEQSTPSRIRKAKLSSPMTTTSTSQKPVLGK RVATPHASARAQTVTSTPVQGRLEKQVSGTPSTVPATLLQPQPASSKTT SSRNVTSGAGTSSASSARQPSASASVLSPTEDDVVSPATSPLSMLSSASP SPAKSAPPSPVKGRGSRVGVPSLKPTLGGKAVVGRPPSVPVSGSAPGRL SGSSRAASTTPTYPAVTTVYPPSSTAKSSVSNAPPVASPSILKPGASAALQ SRRSTGTAAVGSPVKSTTGMKTVAFDLSSPQKSGTGPQPGSAGMGGAK TPSDAVQNILQKIEKIKNTEE |
| 2 | HCMV pp150-2 | DDVVSPATSPLSMLSSASPSPAKSAPPSPVKGRGSRVGVPSLKPTLGGKA VVGRPPSVPVSGSAPGRLSGSSRAASTTPTYPAVTTVYPPSSTAKSSVSN APPVASPSILKPGASAALQSRRSTGTAAVGSPVKSTTGMKTVAFDLSSP QKSGTGPQPGSAGMGGAKTPSDAVQNILQKIEKIKNTEE |
| 3 | HCMV pp28 | MGAELCKRICCEFGTTPGEPLKDALGRQVSLRSYDNIPPTSSSDEGEDDD DGEDDDNEERQQKLRLCGSGCGGNDSSSGSHREATHDGSKKNAVRSTF REDKAPKPSKQSKKKKKPSKFIHHHQQSSIMQETDDLDEEDTSIYLSPPP VPPVQVVAKRLPRPDTPRTPRQKKISQRPPTPGTKKPAASLPF |
| 4 | HCMV pp65 | MESRGRRCPEMISVLGPISGHVLKAVFSRGDTPVLPHETRLLQTGIHVRV SQPSLILVSQYTPDSTPCHRGDNQLQVQHTYFTGSEVENVSVNVHNPTG RSICPSQEPMSIYVYALPLKMLNIPSINVFIHYPSAAERKHRHLPVADAVI HASGKQMWQARLTVSGLAWTRQQNQWKEPDVYYTSAFVFPTKDVAL RHVVCAHELVCSMENTRATKMQVIGDQYVKVYLESFCEDVPSGKLFM HVTLGSDVEEDLTMTRNPQPFMRPHERNGFTVLCPKNMIIKPGKISHIM LDVAFTSHEHFGLLCPKSIPGLSISGNLLMNGQQIFLEVQAIRETVELRQ YDPVAALFFFDIDLLLQRGPQYSEHPTFTSQYRIQGKLEYRHTWDRHDE GAAQGDDDVWTSGSDSDEELVTTERKTPRVTGGGAMAGASTSAGRKR KSASSATACTSGVMTRGRLKAESTVAPEEDTDEDSDNEIHNPAVFTWPP WQAGILARNLVPMVATVQGQNLKYQEFFWDANDIYRIFAELEGVWQP AAQPKRRRHRQDALPGPCIASTPKKHRG |
| 5 | HCMV gp52 | MDRKTRLSEPPTLALRLKPYKTAIQQLRSVIRALKENTTVTFLPTPSLILQ TVRSHCVSKITFNSSCLYITDKSFQPKTINNSTPLLGNFMYLTSSKDLTKF YVQDISDLSAKISMCAPDFNMEFSSACVHGQDIVRESENSAVHVDLDFG VVADLLKWIGPHTRVKRNVKKAPCPTGTVQILVHAGPPAIKFILTNGSE LEFTSNNRVSFHGVKNMRINVQLKNFYQTLLNCAVTKLPCTLRIVTEHD TLLYVASRNGLFAVENFLTEEPFQRGDPFDKNYVGNSGKSRGGGGGGG SLSSLANAGGLHDDGPGLDNDLMNEPMGLGGLGGGGGGGGKHDRG GGGGSGTRKMSSGGGGGDHDHGLSSKEKYEQHKITSYLTSKGGSGGG GGGGGGGLDRNSGNYFNDAKEESDSEDSVTFEFVPNTKKQKCG |
| 6 | HCMV pp38 | MSHPLSAAVPAATAPPGATVAGASPAVSSLAWPHDGVYLPKDAFFSLL GASRSAVPVMYPGAVAAPPSASPAPLPLPSYPASYGAPVVGYDQLAAR HFADYVDPHYPGWGRRYEPAPSLHPSYPVPPPPSPAYYRRRDSPGGMD EPPSGWERYDGGHRGQSQKQHRHGGSGGHNKRRKETAAASSSSSDED LSFPGEAEHGRARKRLKSHVNSDGGSGGHAGSNQQQQQRYDELRDAIH ELKRDLFAARQSSTLLSAALPSAASSSPTTTTVCTPTGELTSGGGETPTA LLSGGAKVAERAQAGVVNASCRLATASGSEAATAGPSTAGSSSCPASV VLAAAAAQAAAASQSPPKDMVDLNRRIFVAALNKLE |
| 7 | UL48a | MSNTAPGPTVANKRDEKHRHVVNVVLELPTEISEATHPVLATMLSKYT RMSSLFNDKCAFKLDLLRMVAVSRTRR |
| 8 | primer | GGATCCATGAGTTTGCAGTTTATCGGT |
| 9 | primer | GCTAGCTTCCTCCGTGTTCTTAATCTT |
| 10 | primer | GGATCCATGGAGTCGCGCGGTCGCCGT |
| 11 | primer | GCTAGCACCTCGGTGCTTTTTGGGCGT |
| 12 | primer | GGATCCATGGATCGCAAGACGCGCCTC |
| 13 | primer | GCTAGCGCCGCACTTTTGCTTCTTGGT |
| 14 | primer | GAATTCATGTCGCACCCTCTGAGTGCT |

TABLE 1-continued

Sequence information

| SEQ ID NO | Name | Sequence information 5'-3' |
|---|---|---|
| 15 | primer | GCTAGCCTCGAGCTTATTGAGCGCAGC |
| 16 | primer | GGATCCATGGGTGCCGAACTCTGCAAA |
| 17 | primer | GAATTCAAAGGGCAAGGAGGCGGCGGG |
| 18 | primer | GGATCCATGTCTAACACCGCGCCGGGA |
| 19 | primer | GAATTCGCGCCGGGTGCGCGACAC |

SPECIFIC MODES FOR CARRYING OUT THE INVENTION

The present invention is illustrated by reference to the following examples (which are not intended to limit the protection scope of the present invention).

Unless indicated otherwise, the molecular biological experimental methods and immunological assays used in the present invention are carried out substantially in accordance with the methods as described in J. Sambrook et al., Molecular Cloning: A Laboratory Manual (Second Edition), Cold Spring Harbor Laboratory Press, 1989, and F. M. Ausubel et al., Short Protocols in Molecular Biology, 3$^{rd}$ Edition, John Wiley & Sons, Inc., 1995; restriction enzymes are used under the conditions recommended by manufacturers of the products. Those skilled in the art understand that the examples are used for illustrating the present invention, but not intended to limit the protection scope of the present invention.

Example 1. Cloning and Expression of Proteins

In the Example, the inventor obtained 7 proteins by recombinant expression, i.e., HCMV pp150 (UL32), HCMV pp150-2 (a truncated protein of pp150), HCMV pp65 (UL83), HCMV gp52 (UL44), HCMV pp38 (UL80a), HCMV pp28 (UL99) and UL48a. The information of the proteins for recombinant expression is shown in Table 2. The primers for use in PCR amplification of the genes encoding the target proteins are listed in Table 3.

TABLE 2

Information of 7 proteins for recombinant expression

| Protein name | Sequence information | Sequence accession No. | Vector | Bacterial strain |
|---|---|---|---|---|
| HCMV pp150 | SEQ ID NO: 1 | ACL51112 | B11 | BL21 |
| HCMV pp150-2 | SEQ ID NO: 2 | ACL51112 | B11 | BL21 |
| HCMV pp28 | SEQ ID NO: 3 | ACL51167.1 | Pet-GST | er competent |
| HCMV pp65 | SEQ ID NO: 4 | ACL51152.1 | B6 | er competent |
| HCMV gp52 | SEQ ID NO: 5 | ACL51123.1 | B6 | er competent |
| HCMV pp38 | SEQ ID NO: 6 | ACL51150.1 | Pet-GST | er competent |
| UL48a | SEQ ID NO: 7 | ACL51128.1 | Pet-GST | er competent |

TABLE 3

Information of the primers for use in PCR amplification of the genes encoding the target proteins

| SEQ ID NO: | Target protein | Primer | Sequence information 5'-3' |
|---|---|---|---|
| 8 | pp150 (UL32) | upstream | GGATCCATGAGTTTGCAGTTTATCGGT |
| 9 | | downstream | GCTAGCTTCCTCCGTGTTCTTAATCTT |
| 10 | pp65 (UL83) | upstream | GGATCCATGGAGTCGCGCGGTCGCCGT |
| 11 | | downstream | GCTAGCACCTCGGTGCTTTTTGGGCGT |
| 12 | gp52 (UL44) | upstream | GGATCCATGGATCGCAAGACGCGCCTC |
| 13 | | downstream | GCTAGCGCCGCACTTTTGCTTCTTGGT |
| 14 | pp38 (UL80a) | upstream | GAATTCATGTCGCACCCTCTGAGTGCT |
| 15 | | downstream | GCTAGCCTCGAGCTTATTGAGCGCAGC |
| 16 | pp28 (UL99) | upstream | GGATCCATGGGTGCCGAACTCTGCAAA |
| 17 | | downstream | GAATTCAAAGGGCAAGGAGGCGGCGGG |
| 18 | UL48a | upstream | GGATCCATGTCTAACACCGCGCCGGGA |
| 19 | | downstream | GAATTCGCGCCGGGTGCGCGACAC |

Example 2. Establishment of an Antigen Protein-Based ELISA Assay Platform for Detecting an Antibody In the Example, based on HCMV pp150 & pp150-2 (as a combination coating antigen), HCMV pp65 (UL83), HCMV gp52 (UL44), HCMV pp38 (UL80a), HCMV pp28 (UL99) or UL48a, respectively, the inventor established the ELISA assay platforms for detecting an antibody against pp150, an antibody against pp65, an antibody against gp52, an antibody against pp38, an antibody against pp28 and an antibody against UL48a, respectively (called pp150 assay platform, pp65 assay platform, gp52 assay platform, pp38 assay platform, pp28 assay platform, and UL48a assay platform for short, respectively), each comprising: a microwell plate coated with an antigen protein (i.e., a coating antigen), a coating buffer, a blocking solution, a washing solution, an enzyme-labelled anti-human IgG antibody, an enzyme-labelled antibody diluent, negative/positive control, a chromogenic solution and a stop solution.

Coating antigen: HCMV pp150 and pp150-2, HCMV pp65 (UL83), HCMV gp52 (UL44), HCMV pp38 (UL80a), HCMV pp28 (UL99) or UL48a.

Sample diluent: Tris-Base buffer (pH 7.8-8.3), comprising 1-5% (mass/volume ratio) of bovine serum albumin, 5-10% (mass/volume ratio) of sucrose and 2-7% (mass/volume ratio) of casein; and 7-12% (volume/volume ratio) of fetal bovine serum.

Concentrated washing solution: comprising a phosphate buffer (pH 7-7.6) and a surfactant Tween20.

Enzyme-labelled anti-human IgG antibody: Horseradish peroxidase (HRP)-labelled mouse anti-human IgG monoclonal antibody.

Diluent for enzyme-labelled antibody: a phosphate buffer (pH 6.8-7.3), wherein each 1000 ml phosphate buffer comprises 0.1-1 M NaCl and 0.3-1% (mass/volume ratio) of casein, 0.1-0.4% (mass/volume ratio) of TritonX-100, 7-12% (volume/volume ratio) of fetal bovine serum, and 0.2-0.5% (mass/volume ratio) of Geltin.

Chromogenic solution: A solution comprising trisodium citrate, citric acid, sodium acetate, glacial acetic acid and hydrogen peroxide; and, B solution comprising absolute ethyl alcohol, ethylene glycol, dimethyl formamide, and 3,3,5,5-tetramethylbenzidine.

Stop solution: 0.1-1 M sulphuric acid.

Figure 1A:
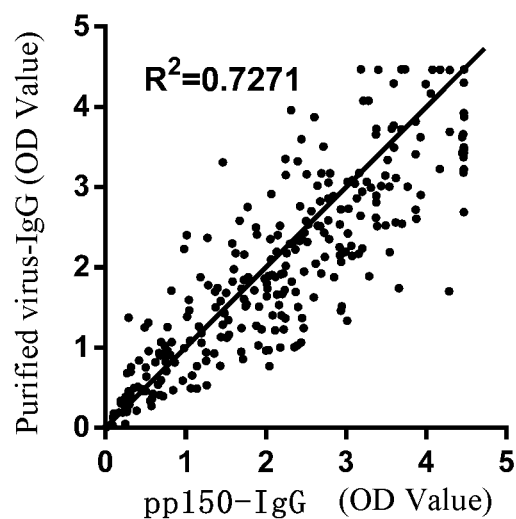
FIGS. 1A and 1B show that the ELISA assay platform (based on pp150 & pp150-2) established in Example 2 can be used to determine the level of an antibody against a CMV protein (an antibody against pp150), and further to determine whether a serum sample is positive or negative.
Figure 1B:
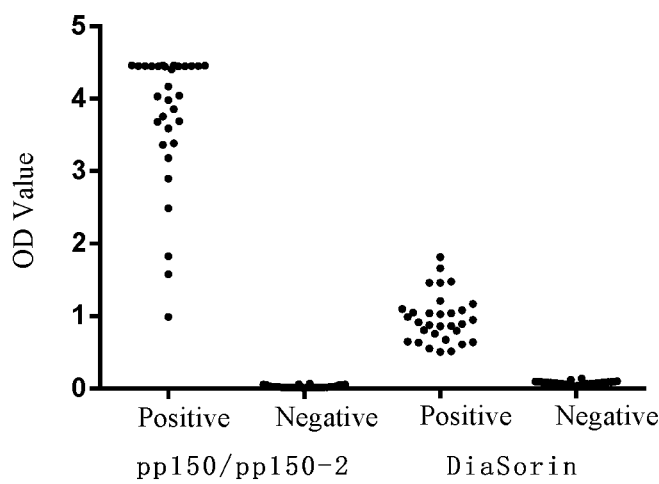

The pp150 antibody assay platform was used as an example below to show the effect of the ELISA assay platform established in the Example. The pp150 & pp150-2-based ELISA assay platform and purified virus-based ELISA assay platform were used to determine 288 randomly selected serums in parallel. The results are shown in FIG. 1A. The results show that the results determined by the two ELISA assay platforms are highly identical, the coincidence rate of them is 99.3%, and the correlation of response intensity is good (correlation coefficient r=0.85). In addition, the pp150 & pp150-2-based ELISA assay platform and a commercially available CMV-IgG reagent (Diasorin-IgG)-based ELISA assay platform were used to determine 36 randomly selected serums in parallel. The results are shown in FIG. 1B. The results show that the reactivity of the pp150 & pp150-2-based ELISA assay platform is significantly stronger than the reactivity of the Diasorin-based ELISA assay platform, wherein the latter has a relatively low level of reactivity for most of the positive serums. The results in FIGS. 1A and 1B show that the ELISA assay platforms established in the Example can be used to determine the level of an antibody against a CMV protein (an antibody against pp150) in a serum sample accurately, reliably and effectively.

Example 3. Detection of an Anti-HCMV-IE1 Antibody by Elispot Assay Platform

In the Example, the inventor established an IE1 protein-based Elispot assay platform for detecting an anti-HCMV-IE1 antibody.

IE1 is a HCMV immediate early protein that is present in the nucleus of an infected cell one hour after the infection. The Elispot assay established in the Example is a method for quickly determining cytomegalovirus titer that was established based on a traditional enzyme-linked immunospot assay in combination with Elispot automated spot counter. Compared with the traditional method for detecting TCID50, the Elispot assay established in the Example obtains the experimental results by the specific binding between a monoclonal antibody and a virus immediate early protein, rather than obtaining the experimental results by cytopathogenic counting or plaque formation. Therefore, since the cells infected by a virus can be detected in the Elispot assay before cytopathogeny, it greatly shortens the time for detection (20 h). In addition, in the Elispot assay, the results are read by automated image collection and spot counting program of the Elispot assay instrument, which greatly improve the stability and accuracy of the detection.

Figure 2:
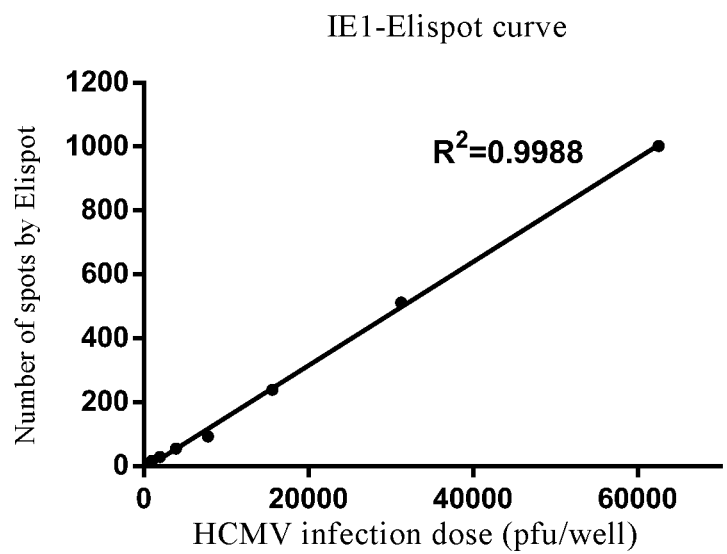
FIG. 2 shows the correlation between HCMV infection dose and Elispot detection value, in the IE1 protein-based Elispot assay platform established in Example 3. The results show that there is a significant linear relationship ($R^2$=0.9988) between HCMV infection dose and Elispot detection value in the Elispot assay platform. This indicates that the Elispot assay platform established in Example 3 can be used to determine the level of an antibody against a CMV protein (an antibody against IE1 protein) in a serum sample accurately, reliably and effectively.

FIG. 2 shows the correlation between the HCMV infection dose and the Elispot detection value, in the IE1 protein-based Elispot assay platform as established in the Example. The results show that there is a significant linear relationship ($R^2=0.9988$) between the HCMV infection dose and the Elispot detection value in the Elispot assay platform. This indicates that the Elispot assay platform established in the Example can be used to determine the level of an antibody against a CMV protein (an antibody against IE1 protein) in a serum sample accurately, reliably and effectively.

Figure 3:
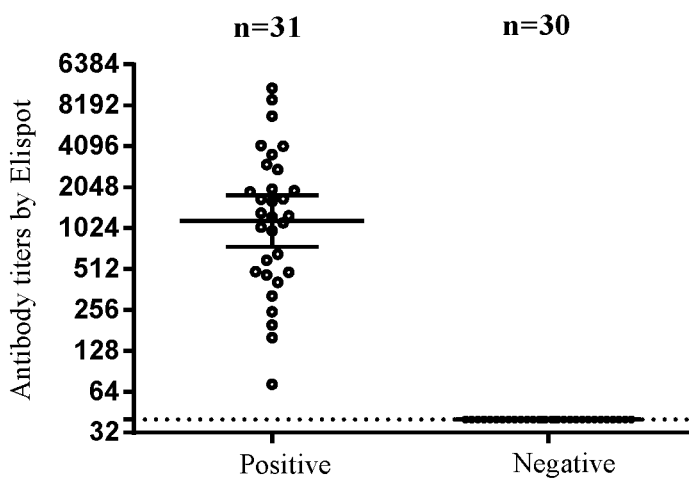
FIG. 3 shows the comparison of the detection results (Elispot NT50) of 61 serum samples by the IE1 protein-based Elispot assay platform established in Example 3 and the detection results by a commercially available HCMV IgG antibody assay kit (Diasorin IgG reagent), wherein, 31 serum samples, which were detected to be positive by the kit, were also detected to be positive in the detection results by the Elispot assay platform; 30 serum samples, which were detected to be negative by the kit, were also detected to be negative in the detection results by the Elispot assay platform; their results are completely consistent with each other. This indicates the accuracy and reliability of the Elispot assay platform established in Example 3.

Furthermore, the results obtained by the Elispot assay platform established in the Example were compared with the results obtained by the commercially available HCMV IgG antibody assay kit (Diasorin-IgG agent, DIASORIN, P002033). The results are shown in FIG. 3. The results show that among the 61 serum samples detected in parallel, the 31 serum samples, which were determined by the kit to be positive, were also positive in the results determined by the Elispot assay platform; and the 30 serum samples, which were determined by the kit to be negative, were also negative in the results determined by the Elispot assay platform; their results were completely identical to each other. This indicates the accuracy and reliability of the Elispot assay platform established in the Example.

Figure 4:
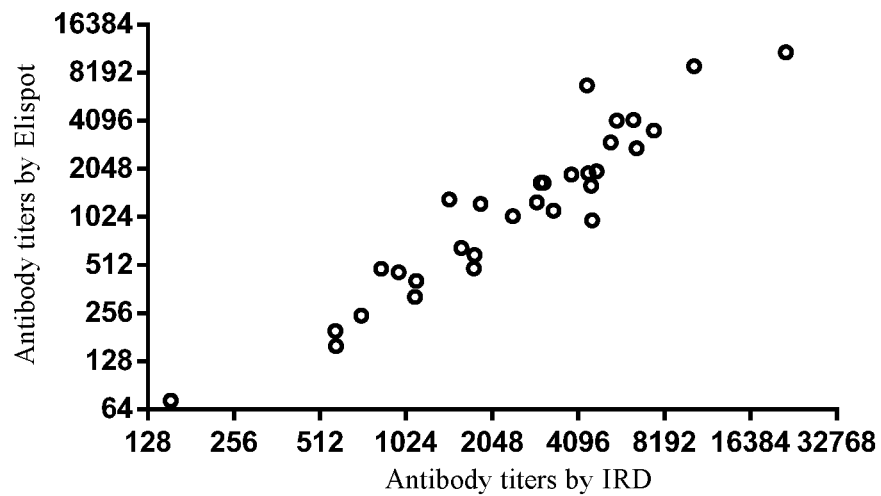
FIG. 4 shows the correlation between the detection results (Elispot NT50) of 61 serum samples by the IE1 protein-based Elispot assay platform established in Example 3 and the detection results by a commercially available HCMV IRD neutralization assay platform (IRD NT50). The results show that there is a significant correlation ($R^2$=0.8960) between the detection results (Elispot NT50) by the Elispot assay platform and the detection results by the IRD neutralization assay platform (IRD NT50). This indicates the accuracy and reliability of the Elispot assay platform established in Example 3.

Furthermore, the results determined by the Elispot assay platform established in the Example were compared with the results determined by HCMV IRD neutralization assay platform as established by Aimin Tang et al. (Aimin Tang, Fengsheng Li, Daniel C. Freed, Adam C. Finnefrock, Danilo R. Casimiro, Dai Wang, Tong-Ming Fu. A novel high-throughput neutralization assay for supporting clinical evaluations of human cytomegalovirus vaccines. Vaccine. 2011 Oct. 26; 29(46): 8350-6). The results are shown in FIG. 4. The results show that the results determined by the Elispot assay platform (Elispot NT50) are in a good correlation ($R^2=0.8960$) with the results determined by the IRD neutralization assay platform (IRD NT50). This indicates the accuracy and reliability of the Elispot assay platform established in the Example.

Example 4. Detection of Serum with a Known Background by ELISA Assay Platform In the Example, the inventor used the ELISA assay platform established in Example 2 to detect the antibodies in 61 serums with known background, so as to confirm the reliability and effectiveness of the ELISA assay platform, wherein the backgrounds of the serum samples had been determined by the commercially available HCMV IRD assay reagent (Aimin Tang, Fengsheng Li, Daniel C. Freed, Adam C. Finnefrock, Danilo R. Casimiro, Dai Wang, Tong-Ming Fu. A novel high-throughput neutralization assay for supporting clinical evaluations of human cytomegalovirus vaccines. Vaccine. 2011, 29:8350-6) and the commercially available HCMV IgG antibody assay kit (Diasorin-IgG agent, DIASORIN, P002033). The detection method comprised the following steps:

step 1: collecting a sample the serum to be tested was centrifuged for 5-10 min (10000 rpm/min), for use in detection;

step 2: loading a sample for detection the ingredients in the kit were equilibrated to room temperature; to the sample well of the coated microwell plate in the ELISA assay platform established in Example 2, a sample diluent (90 ul) and the serum to be tested (10 ul) were added; and meanwhile, a negative control and a positive control were set in the microwell plate, wherein to each of the negative control wells, serum with a negative background (10 ul) and a sample diluent (90 ul) were added; to each of the positive control wells, serum with a positive background (10 ul) and a sample diluent (90 ul) were added; the plate was then shaken to mix the solutions homogeneously on a plate vibrator; the plate was then covered with a sealing film, and the reaction was carried out in a 37° C. incubator/thermostat water bath for 1 h;

step 3: after the reaction, the sealing film was removed, and the wells were washed with a washing solution for 5 times, and dried upside down;

step 4: to each of the wells, an enzyme-labelled anti-human IgG antibody solution (100 ul) was added, and the plate was covered with a sealing film; the reaction was then carried out in a 37° C. incubator/thermostat water bath for 30 min;

step 5: after the reaction, the sealing film was removed, and the wells were washed with a washing solution for 5 times, and dried upside down;

step 6: to each of the wells, a substrate solution A (50 ul) and a substrate solution B (50 ul) were added, and mixed homogeneously; and the reaction was then carried out in a 37° C. incubator/thermostat water bath for 15 min; and step 7: to each well, a stop solution (50 ul) was added, and the plate was then read by a Microplate Reader at OD450, thereby obtaining the OD values for the antibody reactions in the wells. The results are shown in FIG. 5.

Figure 5:
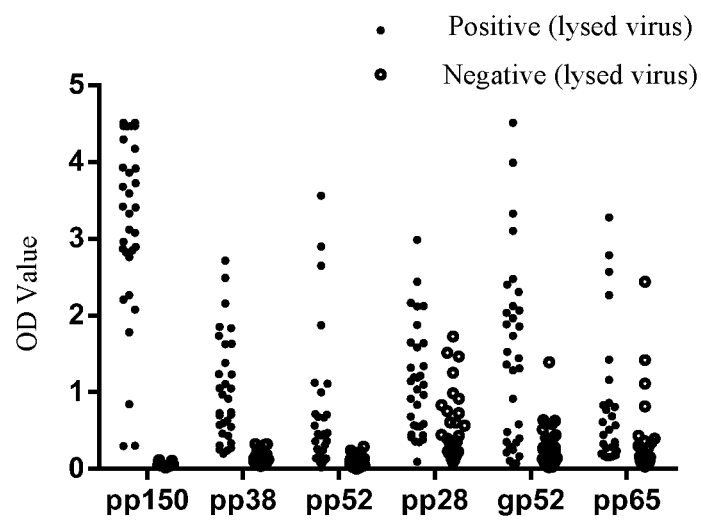
FIG. 5 shows the detection results of 61 serum samples with known background by 6 ELISA assay platforms (which are based on pp150 & pp150-2, HCMV pp65 (UL83), HCMV gp52 (UL44), HCMV pp38 (UL80a), HCMV pp28 (UL99), and UL48a, respectively) established in Example 2, wherein pp150 refers to the ELISA assay platform based on a mixture of pp150 and pp150-2. The results show that the ELISA assay platforms established in Example 2 (in particular, the pp150 & pp150-2-based ELISA assay platform and the pp28-based ELISA assay platform) can determine the level of an antibody against a CMV protein in a serum sample accurately, reliably and effectively, and determine whether a serum sample is negative or positive.

FIG. 5 shows the results of 61 serum samples with known backgrounds as determined by six ELISA assay platforms (which are based on pp150 & pp150-2, HCMV pp65 (UL83), HCMV gp52 (UL44), HCMV pp38 (UL80a), HCMV pp28 (UL99), and UL48a, respectively) as established in Example 2, wherein pp150 refers to the ELISA assay platform based on a mixture of pp150 and pp150-2. The results show that the ELISA assay platforms established in Example 2 (in particular, the pp150 & pp150-2-based ELISA assay platform and the pp28-based ELISA assay platform) can determine the level of an antibody against a CMV protein in a serum sample and determine whether the serum sample is negative or positive, accurately, reliably and effectively.

Example 5. Detection of the Antibody Titer in a Sample by ELISA Assay Platform In the Example, the inventor used the ELISA assay platforms established in Example 2 to determine the antibody titer in a serum sample, so as to confirm the reliability and effectiveness of the ELISA assay platforms.

In brief, in the Example, pp150 was used as an example, and the pp150 & pp150-2-based ELISA assay platform was used to detect HCMV IgG antibody (an antibody against pp150) in parallel in the serial dilution samples of two serums (Serum 1 and Serum 2) (two repeated experimentations were performed for each sample), to determine the antibody titer of an antibody against pp150 in the two serums. During the detection, negative control wells and positive control wells were set, and the detection method comprised the following steps:

step 1: collecting a sample the serum to be tested was centrifuged for 5-10 min (10000 rpm/min), for use in detection;

step 2: loading a sample for detection the ingredients in the kit were equilibrated to room temperature; to the first sample well of the coated microwell plate, a sample diluent (180 ul) was added, and to the second to the tenth sample wells, a sample diluent (100 ul per well) was added; to the first sample well, the serum to be test (20 ul) was then added, and the plate was shaken for 30 s-60 s to mix the solution homogeneously on a plate vibrator; and then, 100 ul solution was drawn from the first sample well and added to the second sample well, and the solution was mixed homogeneously under shaking; 100 ul solution was drawn from the second well and added to the third well, and the solution was mixed homogeneously under shaking; the serial dilution was performed until the tenth well; 100 ul solution was drawn from the tenth well and discarded; the process was repeated to each of the two serums;

meanwhile, negative control wells, positive control wells, and blank control wells were set in the microwell plate, wherein to each of the negative control wells, serum with a negative background (10 ul) and a sample diluent (90 ul) were added; to each of the positive control wells, serum with a positive background (10 ul) and a sample diluent (90 ul) were added; and to each of the blank control wells, a sample diluent (100 ul) was added;

the plate was then covered with a sealing film, and the reaction was carried out in a 37° C. incubator/thermostat water bath for 1 h;

step 3: after the reaction, the sealing film was removed, and the wells were washed with a washing solution for 5 times, and dried upside down;

step 4: to each of the wells, an anti-human IgG antibody solution (100 ul) was added, and the plate was covered with a sealing film; the reaction was then carried out in a 37° C. incubator/thermostat water bath for 30 min;

step 5: after the reaction, the sealing film was removed, and the wells were washed with a washing solution for 5 times, and dried upside down;

step 6: to each of the wells, a substrate solution A (50 ul) and a substrate solution B (50 ul) were added, and mixed homogeneously; and then the reaction was carried out in a 37° C. incubator/thermostat water bath for 15 min; and step 7: to each well, a stop solution (50 ul) was added, and the plate was then read by a Microplate Reader at OD450, thereby obtaining the OD values for the antibody reactions in the wells. The results are shown in Table 4.

In Table 4, Serum 1 and Serum 2 are two independent serum samples, and Group 1 and Group 2 represent two repeated experimentations, and the antibody titer is defined as the maximum dilution fold of serum when OD450 reaches above 0.2. The detection results show that the antibody titer of HCMV IgG (i.e., an antibody against pp150) is 80 in Serum 1, and the antibody titer is 320 in Serum 2.

assay platform and pp65 assay platform (i.e., the number of the samples in which the antibody titer in the latter collected serum increased by 4 folds or more) was 8, 77, 21, 29, 30, 24, and 9, respectively.

Furthermore, in order to evaluate the efficacy of pp150 assay platform for assessing the risk of developing HCMV active infection, the results determined by 6 other assay platforms are used to define an individual having a virus event (i.e., developing HCMV active infection). In brief, the criterion for indicating that an individual has a virus event (i.e., developing HCMV active infection) is that among the 6 detection results of the serum in the individual as obtained by the 6 other assay platforms, at least 2, at least 3 or at least 4 detection results are positive simultaneously.

Table 5 shows the statistical information of the results determined by other 6 assay platforms.

TABLE 4

Determination of antibody titers in samples by ELISA assay platform

| Sample | OD values determined at different dilution folds | | | | | | | | Antibody titer |
|---|---|---|---|---|---|---|---|---|---|
| | 10 | 20 | 40 | 80 | 160 | 320 | 640 | 1280 | |
| Serum 1 (Group 1) | 1.46 | 0.886 | 0.379 | 0.21 | 0.024 | 0.014 | 0.01 | 0.011 | 80 |
| Serum 1 (Group 2) | 1.38 | 0.768 | 0.367 | 0.186 | 0.063 | 0.032 | 0.025 | 0.021 | 160 |
| Serum 2 (Group 1) | 3.288 | 2.289 | 1.533 | 0.783 | 0.406 | 0.201 | 0.087 | 0.042 | 320 |
| Serum 2 (Group 2) | 3.926 | 2.656 | 1.773 | 1.043 | 0.525 | 0.239 | 0.102 | 0.062 | 320 |
| Positive control | 3.589 | 2.503 | 1.614 | 0.918 | 0.441 | 0.163 | 0.061 | 0.02 | 320 |
| Negative control | 0.016 | 0.015 | 0.013 | 0.009 | 0.012 | 0.002 | 0.02 | 0.009 | <10 |
| Blank control | 0.001 | 0.001 | 0.001 | 0.001 | 0.001 | 0.001 | 0.001 | 0.001 | — |

The results in Table 4 show that the ELISA assay platform established in Example 2 (for example, pp150 & pp150-2-based ELISA assay platform) can determine the antibody titer of an antibody against a CMV protein (for example, an antibody against pp150) in a sample accurately, reliably and effectively.

Example 6. Evaluation of the Risk of Developing HCMV Active Infection by ELISA Assay Platform The proteins used in the Example were the proteins obtained in Example 1, and the detection method used was the method described in Example 5.

In brief, in the Example, the ELISA assay platform established in Example 2 (including, pp150 & pp150-2-based ELISA assay platform (called pp150 assay platform for short, the same below), pp28 assay platform, pp38 assay platform, UL48a assay platform, gp52 assay platform, pp65 assay platform) and IE1 antibody assay platform (i.e., the Elispot assay platform for detecting an anti-HCMV-IE1 antibody as described in Example 3) were used to detect the 202 pairs of serums collected from a certain natural population of Guangxi over an interval of 12 months (1 year), which were well preserved.

For each pair of serums, if compared with the serum collected first, the serum collected later has the antibody titer increased by 4 folds or more, it is defined that the detection result of the pair of serums (which are from the same individual, and therefore are regarded as one sample) was "positive".

As defined above, among the 202 pairs of serum samples, the number of the samples determined to be positive by IE1 antibody assay platform, pp150 assay platform, pp28 assay platform, pp38 assay platform, UL48a assay platform, gp52

| Detection results | Number of samples |
|---|---|
| at least 5 results being positive simultaneously (pentuple positive and more) | 5 |
| at least 4 results being positive simultaneously (quadruple positive and more) | 11 |
| at least 3 results being positive simultaneously (triple positive or more) | 19 |
| at least 2 results being positive simultaneously (double positive or more) | 33 |
| at least 1 result being positive simultaneously (single positive or more) | 54 |
| all the 6 results being positive | 148 |

Table 6a shows the results of AUC curve parameter analysis of the pp150 assay platform under different criteria for defining a virus event. Table 6b shows the results of LOGISTIC regression analysis of the pp150 assay platform under different criteria for defining a virus event.

TABLE 6a

AUC curve parameter of the pp150 assay platform under different criteria for defining a virus event

| | Criterion for a virus event | AUC | lower limit | upper limit |
|---|---|---|---|---|
| Baseline level of pp150 antibody | double positive or more | 0.792 | 0.702 | 0.882 |
| | triple positive or more | 0.849 | 0.768 | 0.929 |
| | quadruple positive or more | 0.890 | 0.830 | 0.951 |

TABLE 6b

LOGISTIC regression analysis of the pp150 assay platform under different criteria for defining a virus event

| | Criterion for a virus event | B | sig. | Predict-ivity (%) |
|---|---|---|---|---|
| Baseline level of pp150 antibody | double positive or more | −0.001 | 0.003 | 83.7 |
| | triple positive or more | −0.006 | 0.006 | 90.6 |
| | quadruple positive or more | −0.016 | 0.014 | 94.6 |

The ROC curve analysis of the pp150 assay platform under different criteria for defining a virus event is also shown in FIG. 6A-C, wherein, FIG. 6A show the analysis on sensitivity and specificity of the pp150 assay platform for assessing the occurrence of a virus event (HCMV active infection), when the circumstance where the results determined by other assay platforms are double positive or more is defined as the occurrence of a virus event (HCMV active infection);

FIG. 6B show the analysis on sensitivity and specificity of the pp150 assay platform for assessing the occurrence of a virus event (HCMV active infection), when the circumstance where the results determined by other assay platforms are triple positive or more is defined as the occurrence of a virus event (HCMV active infection); and FIG. 6C show the analysis on sensitivity and specificity of the pp150 assay platform for assessing the occurrence of a virus event (HCMV active infection), when the circumstance where the results determined by other assay platforms are quadruple positive or more is defined as the occurrence of a virus event (HCMV active infection).

The results in Table 6a-6b and FIG. 6A-C show that under all the three circumstances, the accuracy of pp150 assay platform for predicting the occurrence of a virus event (HCMV active infection) is above 80%, and therefore can be used to assess the risk of developing human cytomegalovirus (HCMV) active infection in a subject accurately, reliably and effectively.

Table 7a shows the results of AUC curve parameter analysis of the pp28 assay platform under different criteria for defining a virus event. Table 7b shows the results of LOGISTIC regression analysis of the pp28 assay platform under different criteria for defining a virus event.

TABLE 7a

AUC curve parameter of the pp28 assay platform under different criteria for defining a virus event

| | Criterion for a virus event | AUC | lower limit | Upper limit |
|---|---|---|---|---|
| Baseline level of pp28 antibody | double positive or more | 0.823 | 0.751 | 0.895 |
| | triple positive or more | 0.860 | 0.796 | 0.924 |
| | quadruple positive or more | 0.831 | 0.740 | 0.923 |

TABLE 7b

LOGISTIC regression analysis of the pp28 assay platform under different criteria for defining a virus event

| | Criterion for a virus event | B | sig. | Predict-ability (%) |
|---|---|---|---|---|
| Baseline level of pp28 antibody | double positive or more | −3.258 | 0.000 | 78.2 |
| | triple positive or more | −7.787 | 0.000 | 87.1 |
| | quadruple positive or more | −7.753 | 0.002 | 92.6 |

ROC curve analysis of the pp28 assay platform under different criteria for defining a virus event is also shown in FIGS. 7A-C, wherein, FIG. 7A show the analysis on sensitivity and specificity of the pp28 assay platform for assessing the occurrence of a virus event (HCMV active infection), when the circumstance where the results determined by other assay platforms are double positive or more is defined as the occurrence of a virus event (HCMV active infection);

FIG. 7B show the analysis on sensitivity and specificity of the pp28 assay platform for assessing the occurrence of a virus event (HCMV active infection), when the circumstance where the results determined by other assay platforms are triple positive or more is defined as the occurrence of a virus event (HCMV active infection); and FIG. 7C show the analysis on sensitivity and specificity of the pp28 assay platform for assessing the occurrence of a virus event (HCMV active infection), when the circumstance where the results determined by other assay platforms are quadruple positive or more is defined as the occurrence of a virus event (HCMV active infection).

The results in Table 7a-7b and FIG. 7A-C show that under all the three circumstances, the pp28 assay platform has an accuracy of above 78% for predicting a virus event (HCMV active infection), and therefore can be used to assess the risk of developing human cytomegalovirus (HCMV) active infection in a subject accurately, reliably and effectively.

Example 7. Detection Results of a Certain Natural Population of Guangxi by the pp150 Assay Platform In the Example, the inventor employed the ELISA assay platform (pp150 assay platform) established in Example 2 to assess the risk of developing HCMV active infection in a certain natural population of Guangxi. The detection method and the method for calculating an antibody titer were as described in Example 5.

In brief, the inventor used the pp150 assay platform to detect the two serums obtained from each individual of a certain natural population of Guangxi (1659 persons) before and after an interval of 12 months (1 year). The results show that in the population, the antibody positive rate was 98.7% and 98.9%, and the average antibody titer was 1:269 and 1:260, respectively, for the two detections before and after the interval. This indicates that most of the individuals in the population have been infected with HCMV. The inventor further compared the results of the population obtained by the two detections before and after the interval. The comparative results are shown in FIG. 8-9 and Tables 8a-8b.

In particular, FIG. 8 shows the change in the antibody titer of an antibody against pp150 in the certain natural population over 12 months (one year). The results show that individuals with a higher baseline antibody level (i.e., the antibody titer obtained by the first detection), has a lower probability that the level of an antibody against pp150 increases by 4 folds or more one year later (i.e., the antibody level obtained by the second detection is at least 4 folds higher than the antibody level obtained by the first detection, indicating that the individual has HCMV active infection within the interval of 12 months); while, individuals with a lower baseline antibody level, have a higher probability that the level of an antibody against pp150 increases by 4 folds or more one year later. The results show again that the risk of developing HCMV active infection in an individual is negatively correlated with the baseline antibody level. The lower the level of an antibody against a CMV protein (for example, the titer of an antibody against pp150) is, the higher the risk of infecting CMV in the individual is higher.

FIG. 9 shows the correlation between the baseline level of an antibody against pp150 and the risk of developing HCMV active infection in the natural population, wherein, abscissa represents the baseline level of an antibody against pp150 (antibody titer), and ordinate represents the risk of developing HCMV active infection (ratio). The results show that individuals with a lower baseline antibody level, have a higher risk of developing HCMV active infection later (i.e., the level of an antibody against pp150 increases by 4 folds or more). The risk of HCMV active infection is negatively correlated with the baseline antibody level. When the baseline antibody level (antibody titer) is lower than 10, the risk of developing HCMV active infection is up to 82.6%; and when the baseline antibody level (antibody titer) is no more than 160, the risk of developing HCMV active infection is up to 23.66%. The results in FIG. 9 are also specifically described in Tables 8a-8b.

TABLE 8a

Statistical analysis of the results determined before and after an interval of 12 months in a certain natural population of Guangxi (one year) (I)

| Baseline antibody level | Number of individuals | Number of individuals having a virus event during the period | Infection ratio (%) | relative risk (95% CI) |
|---|---|---|---|---|
| <10 | 23 | 19 | 82.6 | 1.0 |
| 10 | 26 | 18 | 69.2 | 0.838 (0.610-1.151) |
| 20 | 42 | 22 | 52.4 | 0.634 (0.450-0.894) |
| 40 | 86 | 39 | 45.3 | 0.549 (0.407-0.740) |
| 80 | 161 | 27 | 16.8 | 0.203 (0.137-0.300) |
| 160 | 317 | 30 | 9.5 | 0.115 (0.078-0.169) |
| 320 | 404 | 12 | 3.0 | 0.034 (0.020-0.064) |
| 640 | 359 | 3 | 0.8 | 0.010 (0.003-0.032) |
| 1280 | 170 | 1 | 0.6 | 0.007 (0.001-0.051) |
| >2560 | 71 | 0 | 0.0 | 0.0 |
| total | 1659 | 171 | 10.3 | |

TABLE 8b

Statistical analysis of the results determined before and after an interval of 12 months (one year) in a certain natural population of Guangxi (II)

| Baseline antibody level | Number of individuals | Number of individuals having a virus event during the period | Infection ratio (%) | relative risk (95% CI) | Sensitivity | Specificity | Youden index |
|---|---|---|---|---|---|---|---|
| ≤40 | 177 | 98 | 55.37 | 11.2 (8.7-14.6) | 57.3% | 94.7% | 0.52 |
| >40 | 1482 | 73 | 4.93 | | | | |
| ≤80 | 338 | 125 | 36.98 | 10.6 (7.7-14.6) | 73.1% | 85.7% | 0.59 |
| >80 | 1321 | 46 | 3.48 | | | | |
| ≤160 | 655 | 155 | 23.66 | 14.8 (9.0-24.6) | 90.6% | 66.4% | 0.57 |
| >160 | 1004 | 16 | 1.59 | | | | |
| ≤320 | 1059 | 167 | 15.77 | 23.7 (8.8-63.4) | 97.7% | 40.1% | 0.37 |
| >320 | 600 | 4 | 0.67 | | | | |

The results in Table 8a-8b and FIG. 9 also show: (1) for individuals having negative base antibody level (antibody titer<10), the percentage of developing HCMV active infection (primary infection) is up to 82.6% (19/23); while, for individuals having the base antibody level (antibody titer) ≥1:2560, the percentage of developing HCMV active infection (recurrent infection) is 0% (0/71) (p<0.0001); (2) the HCMV active infection ratio is in significantly negative correlation with the base antibody level: the higher the base antibody level is, the lower the HCMV active infection ratio is. For the individuals having an antibody titer>1:80 (accounting for about 80%), the virus active infection ratio is 3.48% within 1 year, while for the individuals having an antibody titer≤1:80 (accounting for about 20%), the virus active infection ratio is 36.98% within 1 year. Similarly, for individuals having an antibody titer≥1:40, the virus active infection ratio is 4.93% within 1 year, while for individuals having an antibody titer≤1:40, the virus active infection ratio is 55.37% within 1 year. For individuals having an antibody titer>1:160, the virus active infection ratio is 1.59% within 1 year, while for individuals having an antibody titer≤1:160, the virus active infection ratio is 23.66% within 1 year.

The results in Table 8b also show: the methods of the invention can be used to determine the relative risk of infection in a subject, wherein, the reference value of the base antibody level (i.e., antibody titer) for determining the relative risk can be set as an antibody titer in a range of 40-320, for example, 40, 80, 160 or an antibody titer of 320. If the antibody titer determined in a sample from a subject is below or equal to the reference value, the subject can be determined to have a high relative risk of developing HCMV active infection. It can be seen from Table 8b that when the reference value is between 40 and 320, the subjects having an antibody titer below the reference value, have a relative risk of more than 10 for developing HCMV active infection, and the lower limit of 95% CI is more than 7. This indicates that there is a strong or a very strong correlation between the parameter (antibody titer) and HCMV active infection.

For example, if the antibody titer determined in a sample from a subject is below or equal to 40, the subject has a relative risk of 11.2 for developing HCMV active infection, and 95% CI is 8.7-14.6 (that is, the risk of developing HCMV active infection is significantly enhanced), compared to a subject having an antibody titer above 40. If the antibody titer determined in a sample from a subject is below or equal to 80, the subject has a relative risk of 10.6 for developing HCMV active infection, and 95% CI is 7.7-14.6, compared to a subject having an antibody titer above 80. If the antibody titer determined in a sample from a subject is below or equal to 160, the subject has a relative risk of 14.8 for developing HCMV active infection, and 95% CI is 9.0-24.6, compared to a subject having an antibody titer above 160. If the antibody titer determined in a sample from a subject is below or equal to 320, the subject has a relative risk of 23.7 for developing HCMV active infection, and 95% CI is 8.8-63.4, compared to a subject having an antibody titer above 320.

In addition, Table 8b also shows that the sensitivity, specificity and Youden index of the methods of the invention for predicting HCMV active infection. It can be seen from Table 8b that when the reference value is set as an antibody titer of 40, the methods of the invention for predicting HCMV active infection have a sensitivity of 57.3%, a specificity of 94.7%, and a Youden index of 0.52; when the reference value is set as an antibody titer of 80, the methods of the invention for predicting HCMV active infection have a sensitivity of 73.1%, a specificity of 85.7%, and a Youden index of 0.59; when the reference value is set as an antibody titer of 160, the methods of the invention for predicting HCMV active infection have a sensitivity of 90.6%, a specificity of 66.4%, and a Youden index of 0.57; when the reference value is set as an antibody titer of 320, the methods of the invention for predicting HCMV active infection have a sensitivity of 97.7%, a specificity of 40.1%, and a Youden index of 0.37. These results show that when the reference value is set as an antibody titer of 80, the methods of the invention have the best predictive effect (i.e, the highest Youden index, which is 0.59); and when the reference value is set as an antibody titer of 160 and 40, the methods of the invention have a good predictive effect (i.e., the Youden index is higher than 0.5).

The multi-factor analysis of the natural population also show that the HCMV active infection rate is independent of gender, age, occupation, degree of education, health habit, etc.

Example 8. Calibration of an Antibody Content in Serum

In the Example, the inventor utilized a standard sample to calibrate the antibody content in a serum sample. The standard sample used was a CMV IgG standard sample (Paul-Ehrlich-Instltut, Referenz-CMV-IgG, Juli 1996, 110 IU/ml), and the target antibody to be calibrated was an antibody against pp150.

For this purpose, the inventor subjected the serial diluents of the standard sample to ELISA assay (the ELISA assay used was as described in Example 5), and plotted the antibody content-antibody reactivity standard curve according to the results determined by ELISA. The standard curve is shown in FIG. 10; wherein, abscissa represents an antibody content (expressed as IU/ml); and ordinate represents antibody reactivity (expressed by the OD value obtained by ELISA). The results show that in a range of 0.06-0.7 IU/ml, there is a significant linear relationship between the antibody content and antibody reactivity ($y=3.163*x-0.073$, $R^2=0.9984$), and the linearity range is more than an order of magnitude. Therefore, the absolute quantification of the antibody content in a serum sample can be carried out by the following solution: (1) subjecting a serum sample to 10-fold gradient dilution; (2) subjecting each diluted serum sample to ELISA assay; and (3) selecting the detection results falling into the linear range, and calculating the antibody content of the initial serum sample according to the linear curve and the dilution fold.

According to the solution above, two serums, collected from each individual of a certain natural population (726 persons) of Guangxi before and after an interval of 12 months (1 year), were subjected to the assay. The detection results show that in the population, the antibody positive rate was 100% as determined before and after an interval of 12 months (1 year), and the average antibody titer was 6.19 IU/ml and 5.08 IU/ml, respectively. The inventor further compared the results determined before and after the interval. The comparative results are shown in FIG. 11 and Table 9.

In particular, FIG. 11 shows the change in the content of an antibody against pp150 in the natural population over 12 months (one year). The results are substantively identical to the results in FIG. 8. Individuals with a lower baseline antibody level, have a higher probability that the level of an antibody against pp150 increases by 4 folds or more one year later (i.e., the antibody level obtained by the second detection is at least 4 folds higher than the antibody level obtained by the first detection, indicating that the individuals have HCMV active infection within the interval of 12 months); while, individuals with a higher baseline antibody level, have a lower probability that the level of an antibody against pp150 increases by 4 folds or more one year later (i.e., developing HCMV active infection). The results show again that the risk of developing HCMV active infection in an individual is negatively correlated with the baseline antibody level in serum. The lower the level of an antibody against HCMV protein (such as the content of an antibody against pp150) in serum is, the higher the risk of infecting HCMV in an individual is.

The results in Tables 9a-9b also show that in the natural population, individuals with a lower baseline antibody level, have a higher risk of developing HCMV active infection later (i.e., the level of an antibody against pp150 increases by 4 folds or more); the baseline level of an antibody against pp150 is in a negative correlation with the risk of HCMV active infection, wherein, an individual, in which the base antibody level is not more than 0.2 IU/ml, has a risk/infection rate of up to 80% for developing HCMV active infection within one year; an individual, in which the base antibody level is not more than 0.8 IU/ml, has a risk/infection rate of up to 60.0% for developing HCMV active infection within one year; an individual, in which the base antibody level is not more than 1.6 IU/ml, has a risk/infection rate of up to 50.0% for developing HCMV active infection within one year; an individual, in which the base antibody level is not more than 3.2 IU/ml, has a risk/infection rate of up to 31.3% for developing HCMV active infection within one year; an individual, in which the base antibody level is not more than 6.4 IU/ml, has a risk/infection rate of up to 19.0% for developing HCMV active infection within one year. In contrast, an individual, in which the base antibody level is above 0.8 IU/ml, has a risk/infection rate of 5.2% for developing HCMV active infection; an individual, in which the base antibody level is above 1.6 IU/ml, has a risk/infection rate of 3.3% for developing HCMV active infection; an individual, in which the base antibody level is above 3.2 IU/ml, has a risk/infection rate of 1.6% for developing HCMV active infection; an individual, in which the base antibody level is higher than 6.4 IU/ml, has a risk/infection rate of 0.8% for developing HCMV active infection; and an individual, in which the base antibody level is above 25.6 IU/ml, has a risk/infection rate of 0 for developing HCMV active infection.

a sample from a subject is below or equal to the reference value, the subject can be regarded as having a high relative risk of developing HCMV active infection. It can be seen from Table 9b that when the reference value is between 0.8 and 6.4 IU/ml, the subjects with an antibody content below the reference value, all have a relative risk of above 11 for developing HCMV active infection exceeding 11, and the lower limit of 95% CI exceeds 7. These indicate that there is a strong correlation or a very strong correlation between the parameter (an antibody content/an antibody absolute quantity) and HCMV active infection.

For example, if the antibody content determined in a sample from a subject is below or equal to 0.8 IU/ml, the subject has a relative risk of 11.6 for developing HCMV active infection, and 95% CI is 7.8-17.2 (that is, the risk of developing HCMV active infection is significantly enhanced), compared to a subject with an antibody content above 0.8 IU/ml. if the antibody content determined in a sample from a subject is below or equal to 1.6 IU/ml, the subject has a relative risk of 15.2 for developing HCMV active infection, and 95% CI is 9.5-24.3, compared to a TABLE 9a Statistical analysis of the results determined before and after an interval of 12 months in a certain natural population of Guangxi (one year) (I)

| Baseline antibody content (IU/ml) | Number of individuals | Number of individuals having a virus event during the period | Infection ratio | Relative risk (95% CI) |
|---|---|---|---|---|
| <=0.2 | 15 | 12 | 80% | 100% |
| 0.2-0.4 | 7 | 5 | 71% | 89.3% (52.4%-152.1%) |
| 0.4-0.8 | 28 | 13 | 46% | 58.0% (36.2%-93.0%) |
| 0.8-1.6 | 38 | 14 | 37% | 46.1% (28.3%-75.0%) |
| 1.6-3.2 | 91 | 12 | 13% | 16.5% (9.2%-29.6%) |
| 3.2-6.4 | 148 | 6 | 4% | 5.1% (2.2%-11.6%) |
| 6.4-12.8 | 186 | 2 | 1% | 1.3% (0.3%-5.5%) |
| 12.8-25.6 | 136 | 1 | 1% | 0.9% (0.1%-6.6%) |
| 25.6-51.2 | 77 | 0 | 0% | 0.8% (0.05%-13.2%) |
| Total | 726 | 65 | 9% | — |

TABLE 9b

Statistical analysis of the results determined before and after an interval of 12 months in a certain natural population of Guangxi (one year) (II)

| Baseline antibody content (IU/ml) | Number of individuals | Number of individuals having a virus event during the period | Infection ratio | relative risk (95% CI) | Sensitivity | Specificity | Youden index |
|---|---|---|---|---|---|---|---|
| <=0.8 | 50 | 30 | 60.0% | 11.6 (7.8-17.2) | 46.15% | 96.97% | 0.43 |
| >0.8 | 676 | 35 | 5.2% | | | | |
| <=1.6 | 88 | 44 | 50.0% | 15.2 (9.5-24.3) | 67.69% | 93.34% | 0.61 |
| >1.6 | 638 | 21 | 3.3% | | | | |
| <=3.2 | 179 | 56 | 31.3% | 19.0 (9.6-37.7) | 86.15% | 81.39% | 0.68 |
| >3.2 | 547 | 9 | 1.6% | | | | |
| <=6.4 | 327 | 62 | 19.0% | 25.2 (8.0-79.6) | 95.38% | 59.91% | 0.55 |
| >6.4 | 399 | 3 | 0.8% | | | | |

The results in Table 9b also show: the methods of the invention can be used to determine the relative risk of infection in a subject, wherein, the reference value of the baseline antibody level (i.e., an antibody content/an antibody absolute quantity) for determining the relative risk can be set as an antibody absolute quantity in a range of 0.8-6.4 IU/ml, for example, an antibody absolute quantity of 0.8, 1.6, 3.2 or 6.4 IU/ml. If the antibody content determined in subject with an antibody content above 1.6 IU/ml. If the antibody content determined in a sample from a subject is below or equal to 3.2 IU/ml, the subject has a relative risk of 19.0 for developing HCMV active infection, and 95% CI is 9.6-37.7, compared to a subject with an antibody content above 3.2 IU/ml. If the antibody content determined in a sample from a subject is below or equal to 6.4 IU/ml, the subject has a relative risk of 25.2 for developing HCMV active infection, and 95% CI is 8.0-79.6, compared to a subject with an antibody content above 6.4 IU/ml.

In addition, Table 9b also shows the sensitivity, specificity and Youden index of the methods of the invention for predicting HCMV active infection when the reference value is set as an antibody content in a range of 0.8-6.4 IU/ml. It can be seen from Table 9b that when the reference value is set as an antibody absolute quantity of 0.8 IU/ml, the methods of the invention for predicting HCMV active infection have a sensitivity of 46.15%, a specificity of 96.97%, and a Youden index of 0.43; when reference value is set as an antibody absolute quantity of 1.6 IU/ml, the methods of the invention for predicting HCMV active infection have a sensitivity of 67.69%, a specificity of 93.34%, and a Youden index of 0.61; when the reference value is set as an antibody absolute quantity of 3.2 IU/ml, the methods of the invention for predicting HCMV active infection have a sensitivity of 86.15%, a specificity of 81.39%, and a Youden index of 0.68; when the reference value is set as an antibody absolute quantity of 6.4 IU/ml, the methods of the invention for predicting HCMV active infection have a sensitivity of 95.38%, a specificity of 59.91%, and a Youden index of 0.55. The results show that when the reference value is set as an antibody absolute quantity of 3.2 IU/ml, the methods of the invention have the best predictive effect (i.e., the highest Youden index, which is 0.68); and, when the reference value is set as an antibody absolute quantity of 0.8, 1.6 and 6.4 IU/ml, the methods of the invention also have good predictive effect (i.e., the Youden index is close to or above 0.5).

In addition, the results in Table 9b also show that with the increase in the set reference value, the methods of the invention for predicting HCMV active infection have the sensitivity increased gradually (increased from 46.15% to 95.38%), but have the specificity decreased gradually (decreased from 99.97% to 59.91%). It is substantively identical to the result of ROC curve analysis. The ROC curve analytic results of the methods are shown in FIG. 12, wherein, the area under the curve is 0.913. It can be seen from FIG. 12 that with the increase in sensitivity, the specificity of the methods of the invention for predicting HCMV active infection decreases gradually. Moreover, the results in FIG. 12 show that the methods of the invention can be used to assess the risk of developing human cytomegalovirus (HCMV) active infection in a subject accurately, reliably and effectively.

Although the embodiments of the invention have been described in detail, a person skilled in the art would understand that according to all the disclosed teachings, details can be amended and modified, and these alterations all fall into the protection scope of the invention. The whole scope of the invention is defined by the attached claims and any equivalent thereof.

REFERENCE DOCUMENTS

Dollard S C, Grosse S D, Ross D S; New estimates of the prevalence of neurological and sensory sequelae and mortality associated with congenital cytomegalovirus infection. Rev Med Virol. 2007, 17:355-363.

Jiang Yi; Congenital cytomegalovirus infection: transmission from mother to infant and diagnosis. CHINESE JOURNAL OF NEONATOLOGY. 2009, 24:261-265.

Fowler K B, Stagno S, Pass R F, et al; The outcome of congenital cytomegalovirus infection in relation to maternal antibody status. N Engl J Med, 1992, 326: 663-667.2

Kenneson A, Cannon M J.; Review and meta-analysis of the epidemiology of congenital cytomegalovirus infection. Rev Med Virol, 2007, 17: 253~276.

Manicklal S, Emery V C, Lazzarotto T, Boppana S B, Gupta R K. The "silent" global burden of congenital cytomegalovirus. Clin Microbiol Rev. 2013, 26:86-102.

Mussi-Pinhata M M, Yamamoto A Y, MouraBrito R M, de Lima Isaac M, de Carvalho e Oliveira P F, Boppana S, Britt W J. Birth prevalence and natural history of congenital cytomegalovirus infection in a highly seroimmune population. Clin Infect Dis. 2009, 49:522-528.

Yamamoto A Y, Mussi-Pinhata M M, Isaac Mde L, Amaral F R, Carvalheiro C G, Aragon D C, Manfredi A K, Boppana S B, Britt W J. Congenital cytomegalovirus infection as a cause of sensorineural hearing loss in a highly immune population. Pediatr Infect Dis J. 2011, 30:1043-1046.

Boppana S B, Rivera L B, Fowler K B, Mach M, Britt W J. Intrauterine transmission of cytomegalovirus to infants of women with preconceptional immunity. N Engl J Med. 2001, 344: 1366-1371.

Ross S A, Arora N, Novak Z, Fowler K B, Britt W J, Boppana S B. Cytomegalovirus reinfections in healthy seroimmune women. J Infect Dis. 2010, 201:386-389.

He Xiaozhou, Wang Xiaofang, Wang Shiwen; Research Progress in Congenital Cytomegalovirus Infection and Detection Method thereof. Chinese Journal of Virology. 2012, 28:73-77.

Ross S A, Novak Z, Pati S, Boppana S B. Overview of the diagnosis of cytomegalovirus infection. Infect Disord Drug Targets. 2011, 11:466-474.

Bernard Weber, Annemarie Berger, Holger Rabenau, Bernard Weber. Human cytomegalovirus infection: diagnostic potential of recombinant antigens for cytomegalovirus antibody detection. Journal of Virological Methods 96 (2001) 157-170.

Jahn G, Scholl B C, Traupe B, Fleckenstein B. The two major structural phosphoproteins (pp65 and pp150) of human cytomegalovirus and their antigenic properties. J Gen Virol. 1987, 68:1327-1337.

Plachter B, Wieczorek L, Scholl B C, Ziegelmaier R, Jahn G. Detection of cytomegalovirus antibodies by an enzyme-linked immunosorbent assay using recombinant polypeptides of the large phosphorylated tegument protein pp150. J Clin Microbiol. 1992, 30: 201-206.

Aimin Tang, Fengsheng Li, Daniel C. Freed, Adam C. Finnefrock, Danilo R. Casimiro, Dai Wang, Tong-Ming Fu. A novel high-throughput neutralization assay for supporting clinical evaluations of human cytomegalovirus vaccines. Vaccine. 2011, 29:8350-6.

The invention claimed is:

1. A method for assessing whether a subject is at risk of developing human cytomegalovirus (HCMV) active infection, comprising the following steps of:
   (1) determining the level of an antibody against a HCMV protein in a body fluid sample from the subject, wherein the antibody is an IgG antibody;
   (2) comparing the level with a predetermined reference value; wherein, the HCMV protein is pp150 or pp28; and if the level is below the reference value, the subject is determined to be at risk of developing HCMV active infection compared with those who have the antibody level above said reference value; and
   (3) treating the subject determined to be at risk of developing HCMV with an appropriate therapeutic regimen for said subject, so as to reduce the risk of developing HCMV active infection in the subject.

2. The method of claim 1, wherein the method is characterized by one or more of the following items:
   (a) the subject is human;
   (b) the body fluid sample is selected from blood, serum, plasma, urine and saliva;
   (c) the active infection is a primary infection by HCMV in a subject that has not been infected by HCMV, or, a re-infection by HCMV or activation of latent HCMV in a subject that has been infected by HCMV;
   (d) the level of the antibody against the HCMV protein in the body fluid sample is determined by immunologic assay;
   (e) the level refers to an antibody titer, and the reference value refers to a predetermined antibody titer; or the level is an antibody absolute quantity and the reference value refers to a predetermined antibody absolute quantity; and
   (f) the method further comprises: before the step (1), providing a body fluid sample from the subject.

3. The method according to claim 1, wherein in the step (1), the level refers to an antibody titer, and the antibody titer of the antibody against pp150 and/or pp28 in the body fluid sample is determined by ELISA; and
the reference value is an antibody titer in a range of 40-320.

4. The method of claim 3, wherein the reference value is 40, and if the antibody titer of the antibody against pp150 is below or equal to 40, the subject is determined to have a relative risk of 11.2 for developing HCMV active infection, with 95% CI of 8.7-14.6; and/or, the subject is determined to have a probability of 55.37% for developing HCMV active infection; or,
   the reference value is 80, and if the antibody titer of the antibody against pp150 is below or equal to 80, the subject is determined to have a relative risk of 10.6 for developing HCMV active infection, with 95% CI of 7.7-14.6, and/or, the subject is determined to have a probability of 36.98% for developing HCMV active infection; or,
   the reference value is 160, and if the antibody titer of the antibody against pp150 is below or equal to 160, the subject is determined to have a relative risk of 14.8 for developing HCMV active infection, with 95% CI of 9.0-24.6; and/or, the subject is determined to have a probability of 23.66% for developing HCMV active infection.

5. The method of claim 3, wherein pp150 and/or an antigenic fragment thereof is used to determine the antibody titer of the antibody against pp150 in the body fluid sample by ELISA; and/or, pp28 and/or an antigenic fragment thereof is used to determine the antibody titer of the antibody against pp28 in the body fluid sample by ELISA.

6. The method of claim 5, wherein pp150 has an amino acid sequence set forth in SEQ ID NO: 1; and/or, the antigenic fragment of pp150 has an amino acid sequence set forth in SEQ ID NO: 2; and/or pp28 has an amino acid sequence set forth in SEQ ID NO: 3.

7. The method according to claim 1, wherein, in the step (1), the level is an antibody absolute quantity, and the absolute quantity of the antibody against pp150 and/or pp28 in the body fluid sample is determined; and the reference value is an antibody absolute quantity in a range of 0.8-6.4 IU/ml.

8. The method of claim 7, wherein the reference value is 0.8 IU/ml, and if the absolute quantity of the antibody against pp150 is below or equal to 0.8 IU/ml, the subject is determined to have a relative risk of 11.6 for developing HCMV active infection, with 95% CI of 7.8-17.2; and/or, the subject is determined to have a probability of 60.0% for developing HCMV active infection; or, the reference value is 1.6 IU/ml, and if the absolute quantity of the antibody against pp150 is below or equal to 1.6 IU/ml, the subject is determined to have a relative risk of 15.2 for developing HCMV active infection, with 95% CI of 9.5-24.3; and/or, the subject is determined to have a probability of 50.0% for developing HCMV active infection; or, the reference value is 3.2 IU/ml, and if the absolute quantity of the antibody against pp150 is below or equal to 3.2 IU/ml, the subject is determined to have a relative risk of 19.0 for developing HCMV active infection, with 95% CI of 9.6-37.7, and/or, the subject is determined to have a probability of 31.3% for developing HCMV active infection.

9. A kit for assessing whether a subject is at risk of developing human cytomegalovirus (HCMV) active infection comprising, a reagent capable of determining the level of an antibody against a HCMV protein, and instructions of using the reagent to determine the level of an antibody against a HCMV protein in a body fluid sample from the subject so as to assess whether the subject is at risk of developing human cytomegalovirus (HCMV) active infection, wherein the HCMV protein is pp150 or pp28 and wherein the antibody is an IgG antibody; and a non-natural antibody against HCMV.

10. The kit of claim 9, wherein the reagent is capable of determining the level of an antibody against a HCMV protein by immunologic assay.

11. The kit of claim 10, wherein the reagent is selected from: the HCMV protein or an antigenic fragment thereof, a fusion protein comprising the HCMV protein or an antigenic fragment thereof, and any combination thereof.

12. The kit of claim 10, wherein the HCMV protein is pp150, and the reagent is pp150 and/or an antigenic fragment thereof; or, the HCMV protein is pp28, and the reagent is pp28 and/or an antigenic fragment thereof; or, the HCMV protein is pp150 and pp28, and the reagent comprises: pp150 and/or an antigenic fragment thereof as a first component, and pp28 and/or an antigenic fragment thereof as a second component.

13. The kit of claim 12, wherein pp150 has an amino acid sequence set forth in SEQ ID NO: 1; and/or, the antigenic fragment of pp150 has an amino acid sequence set forth in SEQ ID NO: 2; and/or, pp28 has an amino acid sequence set forth in SEQ ID NO: 3.

14. The kit of claim 9, wherein the kit further comprises: (i) a device for collecting or storing the body fluid sample from the subject; and/or (ii) an additional reagent necessary for the assay.

15. The kit of claim 14, wherein the additional reagent necessary for the assay is selected from a buffer, a diluent, a blocking solution, a labelled anti-antibody, a standard sample and any combination thereof.

* * * * *